(12) United States Patent
Herrmann et al.

(10) Patent No.: US 7,781,439 B2
(45) Date of Patent: *Aug. 24, 2010

(54) PYRAZOLOPYRIMIDINES

(75) Inventors: Stefan Herrmann, Langenfeld (DE); Olaf Gebauer, Leverkusen (DE); Herbert Gayer, Monheim (DE); Stefan Hillebrand, Neuss (DE); Ulrich Heinemann, Leichlingen (DE); Oliver Guth, Leverkusen (DE); Kerstin Ilg, Köln (DE); Thomas Seitz, Langenfeld (DE); Ronald Ebbert, Nürnberg (DE); Ulrike Wachendorff-Neumann, Neuwied (DE); Peter Dahmen, Neuss (DE); Karl-Heinz Kuck, Langenfeld (DE); Horst-Peter Antonicek, Bergisch Gladbach (DE)

(73) Assignee: Bayer CropScience AG, Monheim (DE)

( * ) Notice: Subject to any disclaimer, the term of this patent is extended or adjusted under 35 U.S.C. 154(b) by 7 days.

This patent is subject to a terminal disclaimer.

(21) Appl. No.: 11/816,253

(22) PCT Filed: Feb. 7, 2006

(86) PCT No.: PCT/EP2006/001064

§ 371 (c)(1),
(2), (4) Date: May 16, 2008

(87) PCT Pub. No.: WO2006/087120

PCT Pub. Date: Aug. 24, 2006

(65) Prior Publication Data

US 2008/0287463 A1 Nov. 20, 2008

(30) Foreign Application Priority Data

Feb. 17, 2005 (DE) .................. 10 2005 007 534

(51) Int. Cl.
*A01N 43/90* (2006.01)
*A61K 31/519* (2006.01)
*C07D 487/00* (2006.01)

(52) U.S. Cl. .................. 514/259.3; 544/281
(58) Field of Classification Search .......... None
See application file for complete search history.

(56) References Cited

U.S. PATENT DOCUMENTS

| 2,444,605 | A | * | 7/1948 | Heimbach et al. ........... 430/615 |
| 3,515,715 | A | | 6/1970 | Straley et al. |
| 3,634,391 | A | | 1/1972 | Fisher et al. |
| 4,838,925 | A | | 6/1989 | Tseng |
| 6,156,925 | A | | 12/2000 | Meyer et al. |
| 2007/0037828 | A1 | | 2/2007 | Gebauer et al. |
| 2007/0244111 | A1 | | 10/2007 | Gebauer et al. |
| 2007/0259893 | A1 | | 11/2007 | Gebauer et al. |
| 2008/0021045 | A1 | | 1/2008 | Gebauer et al. |

FOREIGN PATENT DOCUMENTS

| DE | 3825043 A1 | 2/1990 |
| EP | 1 002 788 B1 | 3/2004 |
| WO | WO 02/48151 A1 | 6/2002 |
| WO | WO 03/009687 A1 | 2/2003 |
| WO | WO 03/092392 * | 11/2003 |
| WO | WO 2004/000844 A1 | 12/2003 |
| WO | WO 2004/005876 A1 | 1/2004 |
| WO | WO 2004/006913 A1 | 1/2004 |
| WO | WO 2004/076458 A1 | 9/2004 |
| WO | WO 2004/106341 A1 | 12/2004 |
| WO | WO 2005/000851 A1 | 1/2005 |
| WO | WO 2005/056556 A1 | 6/2005 |
| WO | WO 2005/056557 A1 | 6/2005 |
| WO | WO 2005/056558 A1 | 6/2005 |
| WO | WO 2005/082907 A2 | 9/2005 |

OTHER PUBLICATIONS

Borisy, et. al., Proceedings of the National Academy of Sciences of the United States of America, 100(13) 7977-7982.*
Huppatz, J.L., "Systemic Fungicides. The Synthesis of Pyrazolo[1,5-a]pyrimidine Analogues of Carboxin," *Aust. J. Chem.* 38:221-230, Commonwealth Scientific And Industrial Research Organization (1985).
International Search Report for International Application No. PCT/EP2006/001064, European Patent Office, Netherlands, mailed on Oct. 2, 2006.

* cited by examiner

*Primary Examiner*—James O Wilson
*Assistant Examiner*—Jeffrey H Murray
(74) *Attorney, Agent, or Firm*—Sterne, Kessler, Goldstein & Fox P.L.L.C.

(57) ABSTRACT

Pyrazolopyrimidines of the formula

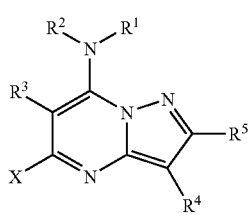

(I)

in which
$R^1$, $R^2$, $R^3$, $R^4$, $R^5$ and X are as defined in the description, processes for preparing these compounds and their use for controlling unwanted microorganisms.

9 Claims, No Drawings

PYRAZOLOPYRIMIDINES

This application is a National Stage of International Application No. PCT/EP2006/001064, filed Feb. 7, 2006, which claims the benefit of German Patent Application No. 10 2005 007534.7, filed Feb. 17, 2005. The entirety of each of these applications is incorporated by reference herein.

The invention relates to pyrazolopyrimidines, to a process for their preparation and to their use for controlling unwanted microorganisms.

It is already known that certain pyrazolopyrimidines have fungicidal properties (see, for example, WO-A 02/048 151, WO-A 04/000 844, WO-A 04/106 341 or WO-A 05/082 907).

However, since the ecological and economical demands made on modern fungicides are increasing constantly, for example with respect to activity spectrum, toxicity, selectivity, application rate, formation of residues and favourable manufacture, and there can furthermore be problems, for example, with resistance, there is a constant need to develop novel fungicides which, at least in some areas, have advantages over those of the prior art.

This invention now provides novel pyrazolopyrimidines of the formula (I)

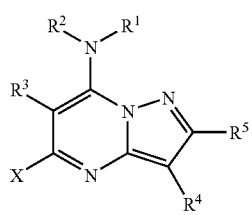

in which the symbols are as defined below:
$R^1$ represents hydrogen, optionally substituted alkyl, optionally substituted alkenyl, optionally substituted alkynyl, optionally substituted cycloalkyl or optionally substituted heterocyclyl, hydroxyl, optionally substituted alkoxy, amino, optionally substituted alkylamino or optionally substituted dialkylamino;
$R^2$ represents hydrogen or alkyl;
or
$R^1$ and $R^2$ together with the nitrogen atom to which they are attached represent an optionally substituted heterocyclic ring;
$R^3$ represents optionally substituted aryl, optionally substituted heterocyclyl, optionally substituted alkyl, optionally substituted alkenyl, optionally substituted alkynyl, optionally substituted cycloalkyl, optionally substituted cycloalkenyl, optionally substituted aralkyl, halogen, an optionally substituted amino group, optionally substituted ($C_1$-$C_8$)-alkoxy, optionally substituted ($C_1$-$C_8$)-alkylthio, optionally substituted ($C_6$-$C_{10}$)-aryloxy, optionally substituted ($C_6$-$C_{10}$)-arylthio, optionally substituted heterocyclyloxy, optionally substituted ($C_6$-$C_{10}$)-aryl-($C_1$-$C_4$)-alkoxy, optionally substituted ($C_6$-$C_{10}$)-aryl-($C_1$-$C_4$)-alkylthio, optionally substituted heterocyclyl-($C_1$-$C_4$)-alkoxy, optionally substituted heterocyclyl-($C_1$-$C_4$)-alkylthio, $C(S)OR^8$, $C(O)SR^8$ or $C(S)SR^8$;
$R^4$ represents $CONR^6R^7$;
$R^5$ represents H, halogen, optionally halogen-substituted alkyl or optionally halogen-substituted cycloalkyl, O—($C_1$-$C_4$)-alkyl or $S(O)_{0-2}$($C_1$-$C_4$)-alkyl;
X represents halogen, cyano, hydroxyl, optionally substituted alkyl, ($C_1$-$C_3$)-haloalkyl, optionally substituted alkoxy, optionally substituted phenyl, optionally substituted alkylthio, optionally substituted alkylsulphinyl or optionally substituted alkylsulphonyl;
$R^6$ represents H, a cation, for example an optionally alkyl- or arylalkyl-substituted ammonium ion, optionally substituted alkyl, optionally substituted alkenyl, optionally substituted alkynyl, optionally substituted cycloalkyl and optionally substituted cycloalkenyl, optionally substituted aryl and optionally substituted arylalkyl;
$R^7$ represents $COR^8$, $S(O)_{1-2}R^8$, cyano, $COOR^8$, $CON(R^8)_2$, where the radicals $R^8$ may be identical or different, saturated, partially or fully unsaturated or aromatic, optionally substituted 5- or 6-membered heterocyclyl which optionally contains 1 or up to three further heteroatoms selected from N, S and/or O atoms, where oxygen atoms may not be adjacent to one another;
$R^8$ independently of the other radicals represents H, optionally substituted alkyl, haloalkyl, optionally substituted alkenyl, optionally substituted alkynyl, optionally substituted cycloalkyl, optionally substituted cycloalkenyl, optionally substituted aryl or optionally substituted aralkyl; or two radicals $R^8$ form a cycle having 3 to 6 carbon atoms which is saturated or partially unsaturated and, if appropriate, contains 1 or 2 further N, S or O atoms, where oxygen atoms may not be adjacent to one another;
or
$R^6$ and $R^8$ together with the N—CO or N—S(O)$_{1-2}$ group to which they are attached form a 4- to 8-membered cycle which may contain one or more heteroatoms from the group consisting of sulphur, oxygen and nitrogen, where oxygen atoms may not be adjacent to one another;

and agrochemically active salts thereof.

Pyrazolopyrimidines of the formula (I) are highly suitable for controlling unwanted microorganisms. Especially, they have strong fungicidal activity and can be used both in crop protection and in the protection of materials.

The compounds of the formula (I) can be present both in pure form and as mixtures of different possible isomeric forms, in particular of stereoisomers, such as E and Z, threo and erythro and also optical isomers, such as R and S isomers or atropisomers, and, if appropriate, also of tautomers. The invention encompasses both the pure isomers and their mixtures.

Depending on the nature of the substituents defined above, the compounds of the formula (I) have acidic or basic properties and are capable of forming salts, if appropriate also inner salts. If the compounds of the formula (I) carry hydroxyl groups, carboxyl groups or other groups which induce acidic properties, these compounds can be reacted with bases to form salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having ($C_1$-$C_4$)-alkyl radicals, mono-, di- and trialkanolamines of ($C_1$-$C_4$)-alkanols, choline and chlorocholine. If the compounds of the formula (I) carry amino groups, alkylamino groups or other groups which induce basic properties, these compounds can be reacted with acids to give salts. Suitable acids are, for example, mineral acids, such as hydrochloric acid, sulphuric acid and phosphoric acid, organic acids, such as acetic acid or oxalic acid, and acidic salts, such as $NaHSO_4$ and $KHSO_4$. The salts obtainable in this manner also have fungicidal properties.

The formula (I) provides a general definition of the pyrazolopyrimidines according to the invention.

Preference is given to compounds of the formula (I) in which $R^6$ has one of the following meanings:

a$^1$: H, a$^2$: cation, a$^3$: optionally substituted alkyl, a$^4$: optionally substituted alkenyl, a$^5$: optionally substituted alkynyl, a$^6$: optionally substituted cycloalkyl, a$^7$: optionally substituted cycloalkenyl, a$^8$: optionally substituted aryl or a$^9$: optionally substituted arylalkyl.

Preference is also given to compounds of the formula (I) in which $R^7$ has one of the following meanings:

a$^{1'}$: COR$^8$, a$^{2'}$: SO$_{1-2}$R$^8$, a$^{3'}$: cyano, a$^{4'}$: COOR$^8$, a$^{5'}$: CON(R$^8$)$_2$, where the radicals R$^8$ can be identical or different, or a$^{6'}$: saturated, partially unsaturated or aromatic, optionally substituted 5- or 6-membered heterocyclyl.

Preference is also given to compounds of the formula (I) in which $R^6$=H or a cation and $R^7$ has one of the following meanings:

a$^{1'}$: COR$^8$, a$^{2'}$: SO$_{1-2}$R$^8$, a$^{3'}$: cyano, a$^{4'}$: COOR$^8$, a$^{5'}$: CON(R$^8$)$_2$, where the radicals R$^8$ can be identical or different, or a$^{6'}$: saturated, partially unsaturated or aromatic, optionally substituted 5- or 6-membered heterocyclyl.

Preference is also given to compounds of the formula (I) in which $R^6$ has one of the following meanings:

a$^{1''}$: a$^1$, a$^2$, a$^3$, a$^4$, a$^5$, a$^6$, a$^7$, a$^8$, a$^{2''}$: a$^1$, a$^2$, a$^3$, a$^4$, a$^5$, a$^6$, a$^7$, a$^9$, a$^{3''}$: a$^1$, a$^2$, a$^3$, a$^4$, a$^5$, a$^6$, a$^8$, a$^9$, a$^{4''}$: a$^1$, a$^2$, a$^3$, a$^4$, a$^5$, a$^7$, a$^8$, a$^9$, a$^{5''}$: a$^1$, a$^2$, a$^3$, a$^4$, a$^6$, a$^7$, a$^8$, a$^9$, a$^{6''}$: a$^1$, a$^2$, a$^3$, a$^5$, a$^6$, a$^7$, a$^8$, a$^9$, a$^{7''}$: a$^1$, a$^2$, a$^4$, a$^5$, a$^6$, a$^7$, a$^8$, a$^9$, a$^{8''}$: a$^1$, a$^3$, a$^4$, a$^5$, a$^6$, a$^7$, a$^8$, a$^9$, a$^{9''}$: a$^2$, a$^3$, a$^4$, a$^5$, a$^6$, a$^7$, a$^8$, a$^9$.

Preference is also given to compounds of the formula (I) in which $R^7$ has one of the following meanings:

a$^{1'''}$: a$^{1'}$, a$^{2'}$, a$^{3'}$, a$^{4'}$, a$^{5'}$, a$^{2'''}$: a$^{1'}$, a$^{2'}$, a$^{3'}$, a$^{4'}$, a$^{6'}$, a$^{3'''}$: a$^{1'}$, a$^{2'}$, a$^{3'}$, a$^{5'}$, a$^{6'}$, a$^{4'''}$: a$^{1'}$, a$^{2'}$, a$^{4'}$, a$^{5'}$, a$^{6'}$, a$^{5'''}$: a$^{1'}$, a$^{3'}$, a$^{4'}$, a$^{5'}$, a$^{6'}$, a$^{6'''}$: a$^{2'}$, a$^{3'}$, a$^{4'}$, a$^{5'}$, a$^{6'}$.

Preference is furthermore given to compounds of the formula (I) in which b$^1$) R$^3$ represents optionally substituted aryl, or b$^2$) R$^3$ represents optionally substituted heterocyclyl, or b$^3$) R$^3$ represents optionally substituted alkyl, or b$^4$) R$^3$ represents optionally substituted alkenyl, or b$^5$) R$^3$ represents optionally substituted alkynyl, or b$^6$) R$^3$ represents optionally substituted cycloalkyl, or b$^7$) R$^3$ represents optionally substituted aralkyl, or b$^8$) R$^3$ represents an optionally substituted amino group, or b$^9$) R$^3$ represents optionally substituted (C$_1$-C$_8$)-alkylthio, or b$^{10}$) R$^3$ represents optionally substituted (C$_1$-C$_8$)-alkoxy.

Preference is also given to compounds of the formula (I) in which R$^3$ has one of the following meanings:

c$^1$: b$^1$, b$^2$, b$^3$, b$^4$, b$^5$, b$^6$, b$^7$, b$^8$, b$^9$ c$^2$: b$^1$, b$^2$, b$^3$, b$^4$, b$^5$, b$^6$, b$^7$, b$^8$, b$^{10}$ c$^3$: b$^1$, b$^2$, b$^3$, b$^4$, b$^5$, b$^6$, b$^7$, b$^9$, b$^{10}$ c$^4$: b$^1$, b$^2$, b$^3$, b$^4$, b$^5$, b$^6$, b$^8$, b$^9$, b$^{10}$ c$^5$: b$^1$, b$^2$, b$^3$, b$^4$, b$^5$, b$^7$, b$^8$, b$^9$, b$^{10}$ c$^6$: b$^1$, b$^2$, b$^3$, b$^4$, b$^6$, b$^7$, b$^8$, b$^9$, b$^{10}$ c$^7$: b$^1$, b$^2$, b$^3$, b$^5$, b$^6$, b$^7$, b$^8$, b$^9$, b$^{10}$ c$^8$: b$^1$, b$^2$, b$^4$, b$^5$, b$^6$, b$^7$, b$^8$, b$^9$, b$^{10}$ c$^9$: b$^1$, b$^3$, b$^4$, b$^5$, b$^6$, b$^7$, b$^8$, b$^9$, b$^{10}$ c$^{10}$: b$^2$, b$^3$, b$^4$, b$^5$, b$^6$, b$^7$, b$^8$, b$^9$, b$^{10}$

Preference is furthermore given to those compounds of the formula (I) in which one or more symbols have one of the preferred meanings given below, i.e.

R$^1$ represents hydrogen, alkyl having 1 to 10 carbon atoms which is unsubstituted or mono- to pentasubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, mono- or dialkylamino having in each case 1 to 4 carbon atoms, or R$^1$ represents alkenyl having 2 to 10 carbon atoms which is unsubstituted or mono- to trisubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, mono- or dialkylamino having in each case 1 to 4 carbon atoms, or R$^1$ represents alkynyl having 2 to 10 carbon atoms which is unsubstituted or mono- to trisubstituted by identical or different substituents from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, mono- or dialkylamino having in each case 1 to 4 carbon atoms, or R$^1$ represents cycloalkyl having 3 to 10 carbon atoms which is unsubstituted or mono- to trisubstituted by identical or different substituents from the group consisting of halogen and alkyl having 1 to 4 carbon atoms, or $R^1$ represents saturated or unsaturated heterocyclyl having 3 to 10 ring members and 1 to 3 heteroatoms, such as nitrogen, oxygen and/or sulphur, where the heterocyclyl is unsubstituted or mono- or polysubstituted by halogen, alkyl having 1 to 4 carbon atoms, cyano, nitro, cycloalkyl having 3 to 6 carbon atoms, hydroxyl, alkoxy having 1 to 4 carbon atoms and/or mercapto;

$R^2$ represents hydrogen or alkyl having 1 to 6 carbon atoms;

$R^1$ and $R^2$ together with the nitrogen atom to which they are attached represent a saturated or unsaturated heterocyclic ring having 3 to 8 ring members, where the heterocycle optionally contains a further nitrogen, oxygen or sulphur atom as ring member and where the heterocycle may be unsubstituted or up to trisubstituted by fluorine, chlorine, bromine, alkyl having 1 to 4 carbon atoms, haloalkyl having 1 to 4 carbon atoms and 1 to 9 fluorine and/or chlorine atoms, hydroxyl, alkoxy having 1 to 4 carbon atoms, haloalkoxy having 1 to 4 carbon atoms and 1 to 9 fluorine and/or chlorine atoms, mercapto, thioalkyl having 1 to 4 carbon atoms and/or haloalkylthio having 1 to 4 carbon atoms and 1 to 9 fluorine and/or chlorine atoms;

$R^3$ represents $C_1$-$C_{10}$-alkyl, $C_2$-$C_{10}$-alkenyl, $C_2$-$C_{10}$-alkynyl, $C_3$-$C_8$-cycloalkyl, phenyl-$C_1$-$C_1$-alkyl, where $R^3$ is unsubstituted or partially or fully halogenated and/or optionally carries one to three radicals from the group $R^x$, or $C_1$-$C_{10}$-haloalkyl which optionally carries one to three radicals from the group $R^x$, and $R^x$ represents cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy, or $R^3$ represents phenyl which may be mono- to tetrasubstituted by identical or different substituents from the group consisting of halogen, cyano, nitro, amino, hydroxyl, formyl, carboxyl, carboxyalkyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched haloalkyl, haloalkoxy, haloalkylthio, haloalkylsulphinyl or haloalkylsulphonyl having in each case 1 to 6 carbon atoms and 1 to 13 identical or different halogen atoms;

in each case straight-chain or branched haloalkenyl or haloalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylsulphonyloxy, hydroxyiminoalkyl or alkoximinoalkyl having in each case 1 to 6 carbon atoms in the individual alkyl moieties;

cycloalkyl having 3 to 8 carbon atoms;

2,3-attached 1,3-propanediyl, 1,4-butanediyl, methylenedioxy (—O—$CH_2$—O—) or 1,2-ethylenedioxy (—O—$CH_2$—$CH_2$—O—), where these radicals may be mono- or polysubstituted by identical or different substituents from the group consisting of halogen, alkyl having 1 to 4 carbon atoms and haloalkyl having 1 to 4 carbon atoms and 1 to 9 identical or different halogen atoms;

or $R^3$ represents saturated or fully or partially unsaturated or aromatic heterocyclyl having 3 to 8 ring members and 1 to 3 heteroatoms from the group consisting of nitrogen, oxygen and sulphur, where the heterocyclyl may be mono- or disubstituted by halogen, alkyl having 1 to 4 carbon atoms, alkoxy having 1 to 4 carbon atoms, alkylthio having 1 to 4 carbon atoms, haloalkoxy having 1 to 4 carbon atoms, haloalkylthio having 1 to 4 carbon atoms, hydroxyl, mercapto, cyano, nitro and/or cycloalkyl having 3 to 6 carbon atoms and/or carboxyalkyl;

or $R^3$ represents $C_1$-$C_8$-alkylamino, $C_2$-$C_8$-alkenylamino, $C_2$-$C_8$-alkynylamino, di-$C_1$-$C_8$-alkylamino, di-$C_2$-$C_8$-alkenylamino, di-$C_2$-$C_8$-alkynylamino, $C_2$-$C_8$-alkenyl-($C_2$-$C_8$)-alkynylamino, $C_2$-$C_6$-alkynyl-($C_1$-$C_8$)-alkylamino, $C_2$-$C_8$-alkenyl-($C_1$-$C_8$)-alkylamino, $C_6$-$C_{10}$-arylamino, $C_6$-$C_{10}$-aryl-($C_1$-$C_8$)-alkylamino, $C_6$-$C_{10}$-aryl-($C_1$-$C_4$)-alkyl-($C_1$-$C_8$)-alkylamino, heterocyclyl-($C_1$-$C_8$)-alkylamino or heterocyclyl-($C_1$-$C_4$)-alkyl-($C_1$-$C_8$)-alkylamino;

$R^4$ represents $CONR^6R^7$;

$R^5$ represents H, halogen, ($C_1$-$C_4$)-alkyl which is unsubstituted or substituted by one or more halogen atoms, cyclopropyl which is unsubstituted or substituted by one or more halogen atoms; $SCH_3$, $SOCH_3$, $SO_2CH_3$ or $OCH_3$;

X represents H, fluorine, chlorine, bromine, CN, hydroxyl, alkoxy having 1 to 4 carbon atoms, alkylthio having 1 to 4 carbon atoms or ($C_1$-$C_7$)-alkyl or ($C_1$-$C_3$)-haloalkyl;

$R^6$ represents H, an alkali metal or alkaline earth metal, copper, $NH_4$, mono-($C_1$-$C_{10}$)-alkylammonium, di-($C_1$-$C_{10}$)-alkylammonium, tri-($C_1$-$C_{10}$)-alkylammonium, tetra-($C_1$-$C_{10}$)-alkylammonium, where the alkyl radicals of the ammonium ions may be substituted by aryl or hydroxyl, cholinium, $C_1$-$C_{10}$-alkyl, $C_2$-$C_{10}$-alkenyl, $C_2$-$C_{10}$-alkynyl, $C_3$-$C_8$-cycloalkyl, $C_3$-$C_8$-cycloalkenyl, aryl, phenyl-$C_1$-$C_{10}$-alkyl, where $R^6$ is unsubstituted or partially or fully halogenated and/or optionally carries one to three radicals from the group Rx, or $C_1$-$C_{10}$-haloalkyl which optionally carries one to three radicals from the group $R^x$, and $R^x$ represents cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy and/or $CONR^6R^7$, $CONR^7OR^7$, $COOR^8$, carboxy-($C_1$-$C_4$)-alkyl;

$R^7$ represents $COR^8$, $S(O)_{1-2}R^8$, cyano, $COOR^8$, $CON(R^8)_2$, where the radicals $R^8$ may be identical or different, or

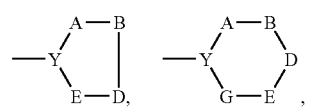

A, B, D, E, G are identical or different and are $CR^9$, $CR^9R^9$, N, $NR^9$, O or S, with the proviso that at least one symbol represents N, O or S and that the oxygen atoms are not adjacent to one another;

Y represents C, CR⁹ or N;

R⁸ independently of the other radicals represents H, $C_1$-$C_{10}$-alkyl, $C_2$-$C_{10}$-alkenyl, $C_2$-$C_{10}$-alkynyl, $C_3$-$C_8$-cycloalkyl, $C_3$-$C_8$-cycloalkenyl, aryl, phenyl-$C_1$-$C_{10}$-alkyl, where R⁸ is unsubstituted or partially or fully halogenated and/or optionally carries one to three radicals from the group R$^x$, or $C_1$-$C_{10}$-haloalkyl which optionally carries one to three radicals from the group R$^x$, and Rx represents cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy; or two radicals R⁸ form a cycle having 3 to 6 carbon atoms which is saturated or partially unsaturated and optionally contains 1 or 2 further N, S or O atoms, where the oxygen atoms may not be adjacent to one another;

or

R⁶ and R⁸ together with the N—CO or N—S(O)$_{1-2}$ group to which they are attached form a 4- to 8-membered cycle which may contain one or more heteroatoms from the group consisting of sulphur, oxygen and nitrogen, where oxygen atoms may not be adjacent to one another;

R⁹ represents R⁷, H, halogen, NR⁷$_2$, OH, SR⁷ or OR⁷.

Particular preference is given to those pyrazolopyrimidines of the formula (I) in which one or more of the symbols have one of the particularly preferred meanings listed below, i.e.

R¹ represents hydrogen or a radical of the formula

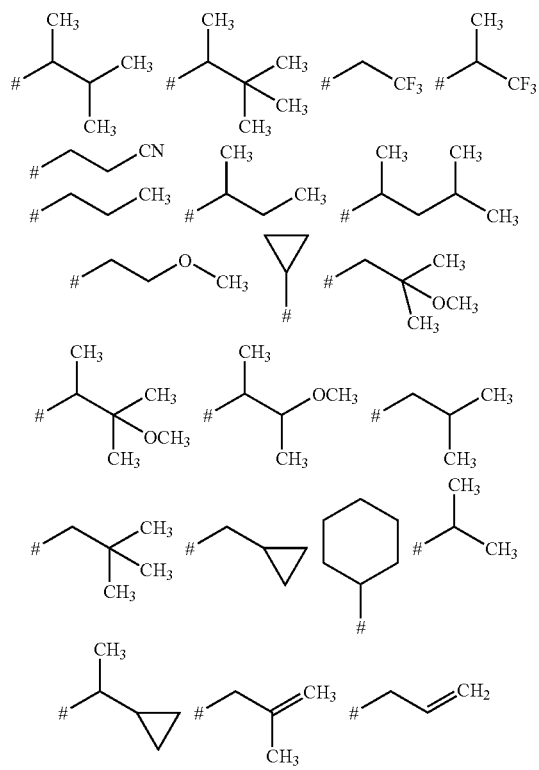

-continued

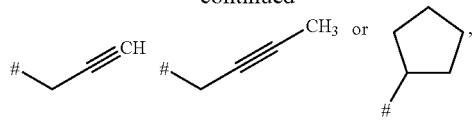

where # denotes the point of attachment (here, these radicals may be present both in optically pure form and in isomer mixtures);

R² represents hydrogen, methyl, ethyl, propyl, or

R¹ and R² together with the nitrogen atom to which they are attached represent pyrrolidinyl, piperidinyl, morpholinyl, thiomorpholinyl, piperazinyl, 3,6-dihydro-1(2H)-pyridinyl or tetrahydro-1(2H)-pyridazinyl, where these radicals are unsubstituted or substituted by 1 to 3 fluorine atoms, 1 to 3 methyl groups and/or trifluoromethyl, or R¹ and R² together with the nitrogen atom to which they are attached represent a radical of the formula

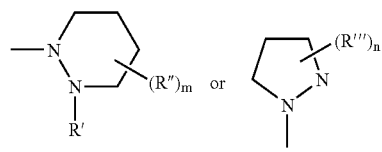

in which

R' represents hydrogen or methyl,

R" represents methyl, ethyl, fluorine, chlorine or trifluoromethyl, m represents the number 0, 1, 2 or 3, where R" represents identical or different radicals if m represents 2 or 3, R'" represents methyl, ethyl, fluorine, chlorine or trifluoromethyl and n represents the number 0, 1, 2 or 3, where R'" represents identical or different radicals if n represents 2 or 3, R³ represents ($C_1$-$C_8$)-alkyl, ($C_2$-$C_6$)-alkenyl, ($C_2$-$C_6$)-alkynyl, ($C_3$-$C_8$)-cycloalkyl, where R³ is unsubstituted or substituted by one or more fluorine or chlorine atoms, benzyl or R³ represents phenyl which may be mono- to trisubstituted by identical or different substituents from the group consisting of fluorine, chlorine, bromine, cyano, nitro, formyl, methyl, ethyl, n- or i-propyl, n-, i-, s- or t-butyl, vinyl, ethynyl, allyl, propargyl, methoxy, ethoxy, n- or i-propoxy, methylthio, ethylthio, n- or i-propylthio, methylsulphinyl, ethylsulphinyl, methylsulphonyl, ethylsulphonyl, allyloxy, propargyloxy, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, trichloroethynyloxy, trifluoroethynyloxy, chloroallyloxy, iodopropargyloxy, methylamino, ethylamino, n- or i-propylamino, dimethylamino, diethylamino, acetyl, propionyl, acetyloxy, methoxycarbonyl, ethoxycarbonyl, hydroximinomethyl, hydroximinoethyl, methoximinomethyl, ethoximinomethyl, methoximinoethyl, ethoximinoethyl, cyclopropyl, cyclobutyl, cyclopentyl or cyclohexyl, or by 2,3-attached 1,3-propanediyl, 1,4-butanediyl, methylenedioxy (—O—CH$_2$—O—) or 1,2-ethylenedioxy (—O—CH$_2$—CH$_2$—O—), where these radicals may be mono- or polysubstituted by identical or different substituents from the group consisting of fluorine, chlorine, methyl, ethyl, n-propyl, i-propyl, trifluoromethyl, carboxyl and carboxymethyl, R$^3$ represents pyridyl which is attached in the 2- or 4-position and may be mono- to tetrasubstituted by identical or different substituents from the group consisting of fluorine, chlorine, bromine, cyano, hydroxyl, mercapto, nitro, methyl, ethyl, methoxy, methylthio, hydroximinomethyl, hydroximinoethyl, methoximinomethyl, methoximinoethyl, trifluoromethyl, carboxyl and carboxymethyl or R$^3$ represents pyrimidyl which is attached in the 2- or 4-position and may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or R$^3$ represents thienyl which is attached in the 2- or 3-position and may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or R$^3$ represents C$_1$-C$_8$-alkylamino or di-C$_1$-C$_8$-alkylamino, or R$^3$ represents thiazolyl which is attached in the 2-, 4- or 5-position and may be mono- or disubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or R$^3$ represents N-piperidinyl, N-tetrazolyl, N-pyrazolyl, N-imidazolyl, N-1,2,4-triazolyl, N-pyrrolyl or N-morpholinyl which are in each case unsubstituted or mono- or—if possible—polysubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl and trifluoromethyl, R$^4$ represents CONR$^6$R$^7$;

R$^5$ represents H, Cl, F, CH$_3$, —CH(CH$_3$)$_2$ or cyclopropyl; a X represents H, F, Cl, CN, C$_1$-C$_4$-alkyl which is unsubstituted or substituted by one or more fluorine or chlorine atoms; and R$^6$ represents H, Na, K, ½Ca, ½Mg, Cu, NH$_4$, NH(CH$_3$)$_3$, N(CH$_3$)$_4$, HN(C$_2$H$_5$)$_3$, N(C$_2$H$_5$)$_4$, H$_2$N(iC$_3$H$_7$)$_2$, H$_3$NCH$_2$Ph, (H$_3$C)$_3$NCH$_2$Ph, cholinium, (C$_1$-C$_8$)-alkyl, (C$_3$-C$_6$)-alkenyl, (C$_1$-C$_8$)-cycloalkenyl, (C$_1$-C$_8$)-cycloalkyl, phenyl, benzyl;

R$^7$ represents COR$^8$, S(O)$_{1-2}$R$^8$, cyano, COOR$^8$, CON(R$^8$)$_2$, where the radicals R$^8$ may be identical or different, pyrrolyl, imidazolyl, pyrazolyl, 1,3,4-triazolyl, thiazolyl, isothiazolyl, 1,3,4-oxadiazolyl, 1,3,4-thiadiazolyl, oxazolyl, isoxazolyl, tetrazolyl, oxadiazinyl, 4H-[1,2,4]-oxadiazin-3-yl, dioxazinyl, 5,6-dihydro-[1,4,2]-dioxazin-3-yl, pyridyl, pyrimidinyl, pyrazinyl, pyridazinyl, where the heterocyclic radicals are optionally substituted by one or more radicals from the group consisting of C$_1$-C$_4$-alkyl, C$_1$-C$_4$-alkoxy and halogen;

R$^8$ independently of the other radicals represents H, (C$_1$-C$_8$)-alkyl, (C$_1$-C$_8$)-haloalkyl, (C$_2$-C$_6$)-alkenyl, propargyl, (C$_3$-C$_8$)-cycloalkyl, benzyl; or two radicals R$^8$ form a cycle having 3 to 6 carbon atoms which is saturated or partially unsaturated and optionally contains 1 or 2 further N, S or O atoms, where oxygen atoms may not be adjacent to one another;

or

R$^6$ and R$^8$ together with the N—CO or N—S(O)$_{1-2}$ group to which they are attached form a 4- to 8-membered cycle which may contain one or more heteroatoms from the group consisting of sulphur, oxygen and nitrogen, where oxygen atoms may not be adjacent to one another.

Very particular preference is given to compounds of the formula (I) in which one or more of the symbols have one of the very particularly preferred meanings listed below, i.e.

R$^1$ and R$^2$ have the particularly preferred meanings listed above;

R$^3$ represents (C$_1$-C$_6$)-alkyl, (C$_2$-C$_6$)-alkenyl, (C$_2$-C$_6$)-alkynyl, (C$_3$-C$_8$)-cycloalkyl, where R$^3$ is unsubstituted or substituted by one or more fluorine or chlorine atoms and/or alkyl, or R$^3$ represents 2,4-, 2,5- or 2,6-disubstituted phenyl, or 2-substituted phenyl or represents 2,4,6- or 2,4,5-trisubstituted phenyl having substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, carboxyl and carboxymethyl or R$^3$ represents pyridyl which is attached in the 2- or 4-position and may be mono- to tetrasubstituted by identical or different substituents from the group consisting of fluorine, chlorine, bromine, cyano, hydroxyl, mercapto, methyl, ethyl, methoxy, methylthio, hydroximinomethyl, hydroximinoethyl, methoximinomethyl, methoximinoethyl, trifluoromethyl, and carboxymethyl or R$^3$ represents pyrimidyl which is attached in the 4-position and may be mono- to trisubstituted by identical or different substituents from the group consisting of fluorine, chlorine, bromine, cyano, hydroxyl, mercapto, methyl, ethyl, methoxy, methylthio, hydroximinomethyl, hydroximinoethyl, methoximinomethyl, methoximinoethyl, trifluoromethyl, and carboxymethyl or R$^3$ represents thienyl which is attached in the 2- or 3-position and may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or R$^4$ represents CONR$^6$R$^7$;

R$^5$ represents H, —CH$_3$, —CH(CH$_3$)$_2$, Cl or cyclopropyl; and X represents fluorine, chlorine, (C$_1$-C$_7$)-alkyl or (C$_1$-C$_3$)-haloalkyl;

R$^6$ represents H, Na, K, NH$_4$, HN(Et)$_2$, H$_2$N(iPr)$_2$, H$_3$NCH$_2$Ph, (H$_3$C)$_3$NCH$_2$Ph, benzyl, (C$_3$-C$_8$)-cycloalkyl, propargyl, (C$_3$-C$_6$)-alkenyl, (C$_1$-C$_8$)-alkyl, fully or partially substituted by F and/or Cl and/or carboxy-(C$_1$-C$_4$)-alkyl, CONR$^6$R$^7$, CONR$^7$OR$^7$, COOR$^8$;

R$^7$ represents COR$^8$, S(O)$_{1-2}$R$^8$, cyano, COOR$^8$, CON(R$^8$)$_2$, where the radicals R$^8$ may be identical or different, 1H-pyrrolyl, 1H-imidazolyl, 1H-pyrazolyl, isoxazolyl, oxazolyl, 1,3,4-oxadiazolyl, 1,3,4-thiadiazolyl, thiazolyl, isothiazolyl, 1H-1,3,4-triazolyl, tetrazolyl, oxadiazinyl, 4H-[1,2,4]-oxadiazin-3-yl, dioxazinyl, 5,6-dihydro-[1,4,2]-dioxazin-3-yl, pyridyl, where the heterocyclic radicals are optionally substituted by one or more radicals from the group consisting of C$_1$-C$_4$-alkyl and halogen;

R⁸ independently of the other radicals represents H, methyl, ethyl, propyl, i-propyl, butyl, i-butyl, sec-butyl, t-butyl, pentyl, hexyl, $(C_1-C_3)$-haloalkyl, $(C_2-C_6)$-alkenyl, propargyl, $(C_3-C_6)$-cycloalkyl, benzyl;

or

R⁶ and R⁸ together with the N—CO or N—S(O)$_{1-2}$ group to which they are attached form a 4- to 8-membered cycle which may contain one or more heteroatoms from the group consisting of sulphur, oxygen and nitrogen, where oxygen atoms may not be adjacent to one another.

Very particular preference is furthermore given to compounds of the formula (I) in which one or more of the symbols have one of the very particularly preferred meanings listed below, i.e.

R¹ and R² have the particularly preferred meanings given above;

R³ represents 2,4-, 2,5- or 2,6-disubstituted phenyl, or 2-substituted phenyl or represents 2,4,6- or 2,4,5-trisubstituted phenyl having substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, carboxyl and carboxymethyl or R³ represents thienyl which is attached in the 2- or 3-position and may be mono- to trisubstituted by identical or different substituents from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or R⁴ represents CONR⁶R⁷;

X represents fluorine, chlorine, methyl or trifluoromethyl;

R⁵ represents H, —CH₃;

R⁶ represents H, Na, K, NH₄, HN(Et)₂, H₂N(iPr)₂, H₃NCH₂Ph, (H₃C)₃NCH₂Ph, benzyl, $(C_3-C_8)$-cycloalkyl, propargyl, $(C_3-C_6)$-alkenyl, $(C_1-C_8)$-alkyl, fully or partially substituted by F and/or Cl and/or carboxy-$(C_1-C_4)$-alkyl, CONR⁶R⁷, CONR⁷OR⁷, COOR⁸;

R⁷ represents COR⁸, S(O)R⁸, COOR⁸, 1H-pyrrolyl, 1H-imidazolyl, 1H-pyrazolyl, isoxazolyl, oxazolyl, 1,3,4-oxadiazolyl, 1,3,4-thiadiazolyl, thiazolyl, isothiazolyl, 1H-1,3,4-triazolyl, tetrazolyl, oxadiazinyl, 4H-[1,2,4]-oxadiazin-3-yl, dioxazinyl, 5,6-dihydro-[1,4,2]-dioxazin-3-yl, pyridyl, where the heterocyclic radicals are optionally substituted by one or more radicals from the group consisting of $C_1-C_4$-alkyl and halogen;

R⁸ independently of the other radicals represents H, methyl, ethyl, propyl, i-propyl, butyl, i-butyl, sec-butyl, t-butyl, pentyl, hexyl, $(C_1-C_3)$-haloalkyl, $(C_2-C_6)$-alkenyl, propargyl, $(C_3-C_6)$-cycloalkyl, benzyl;

or

R⁶ and R⁸ together with the N—CO or N—S(O)$_{1-2}$ group to which they are attached form a 4- to 8-membered cycle which may contain one or more heteroatoms from the group consisting of sulphur, oxygen and nitrogen, where oxygen atoms may not be adjacent to one another.

The radical definitions mentioned above may be combined with one another as desired. Moreover, individual definitions may not apply.

Compounds of the formula (I) in which R⁴ represents CONR⁶R⁷ and X represents Cl (formula Ia in Scheme 1) can be prepared, for example, as shown in Scheme 1 starting with 3-aminopyrazole-4-carboxylic esters (II) which are known from the literature (see, for example, U.S. Pat. No. 3,515,715 and U.S. Pat. No. 3,634,391) and malonic esters (IIa) where R¹¹=$C_1$-$C_8$-alkyl or aryl:

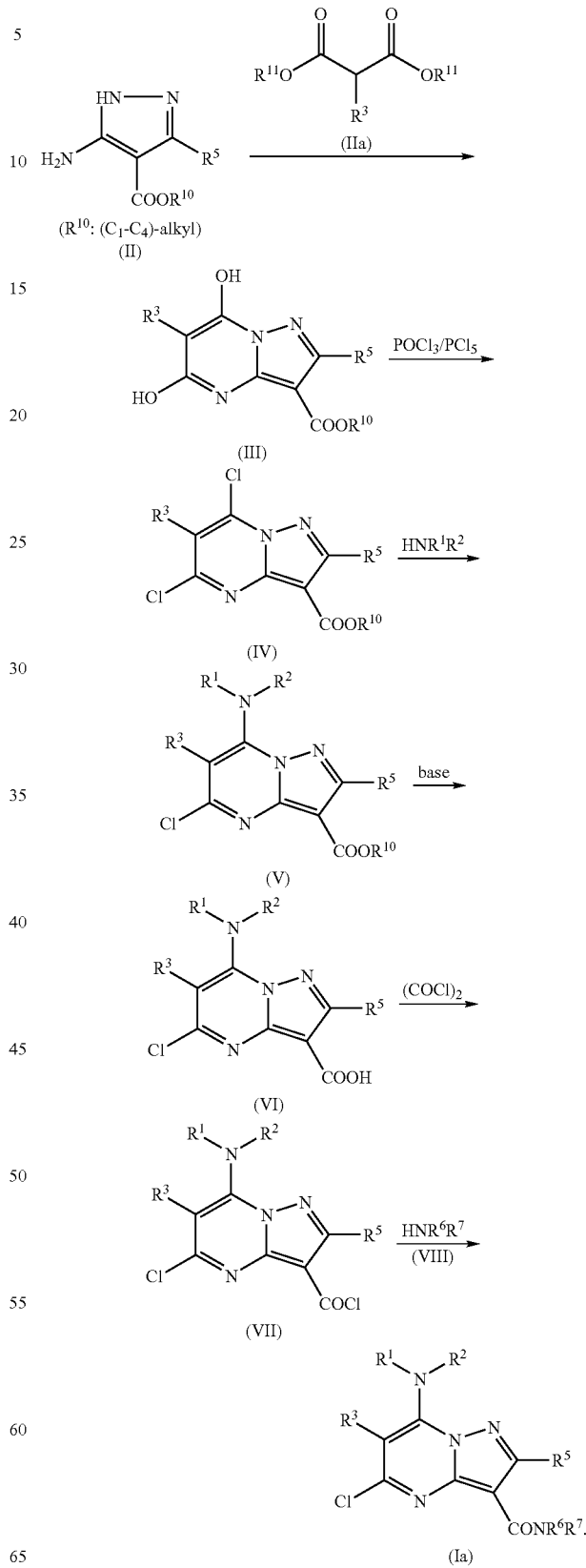

Scheme 1: Process I

The malonic esters (IIa) are known from the literature or can be prepared by processes known from the literature (for example WO 04/006913, WO 04/005876, ($R^3$=heterocyclyl), U.S. Pat. No. 6,156,925 ($R^3$=substituted phenyl), WO-A 03/009687 ($R^3$=substituted alkyl), Chem. Ber. 1956, 89, 996 ($R^3$=substituted cycloalkyl)).

Malonic esters of the formula (IIa) where $R^3$=(2-chloro- or -methyl)thiophen-3-yl (compounds of the formula II b in Scheme 1a) can also be prepared according to Scheme 1a below:

Scheme 1a: Process II

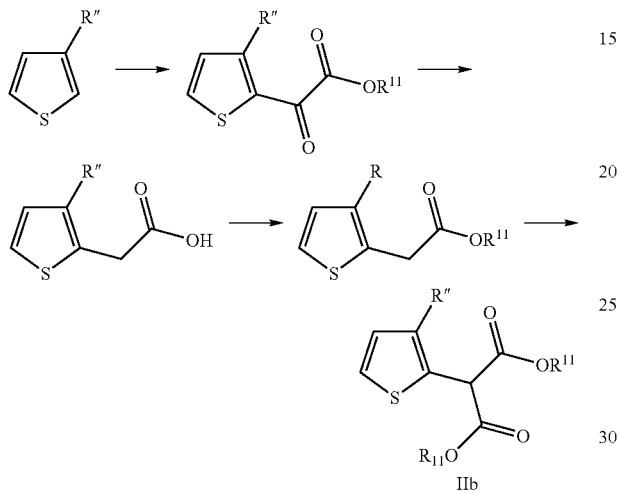

R″ = Me
R″ = Cl
$R^{11}$ = $C_1$-$C_4$-alkyl

Analogously to the last two steps of the synthesis sequence, dimethyl 2-(2-chlorothiophen-3-yl)malonate can also be prepared from (2-chlorothiophen-3-yl)acetic acid.

The step-wise conversion of the starting materials (II) into the amine (V) can be carried out, for example, analogously to the processes given in WO 04/000 844 and in WO 05/082 907. The intermediates II, IV, V, VI and VII and their conversion into one another according to Scheme 1 are already known from WO 05/082 907.

The compounds VIII (amines, amides, sulphonamides, carbamates, ureas and amino-substituted heterocycles) used for further conversion of the acid chlorides (VII) are known. They are commercially available or can be prepared by known processes which are familiar to the person skilled in the art, as described, for example, in Houben-Weyl, Methoden der Organischen Chemie [Methods of Organic Chemistry] or else Adv. Heterocycl. Chem. 1998, 72, 79-116 (and the literature cited therein).

Novel and thus also part of the subject-matter of the present invention is the reaction of the acid chlorides VII with the compounds of the formula VIII to give compounds of the formula Ia.

Alternatively to the process given in Scheme 1, compounds of the formula I in which $R^4$ represents $CONR^6R^7$, $R^7$ represents $COR^8$, $S(O)_{1-2}R^8$ and Het and X represents Cl (compounds of the formula Ia in Scheme 2) can be synthesized by reacting the amides of the formula IX with halogen compounds of the formula X, for example. The amides of the formula XI obtained in this manner are then reacted either with halogen compounds XII or with compounds XIII to give the end products Ia.

Scheme 2: Process III

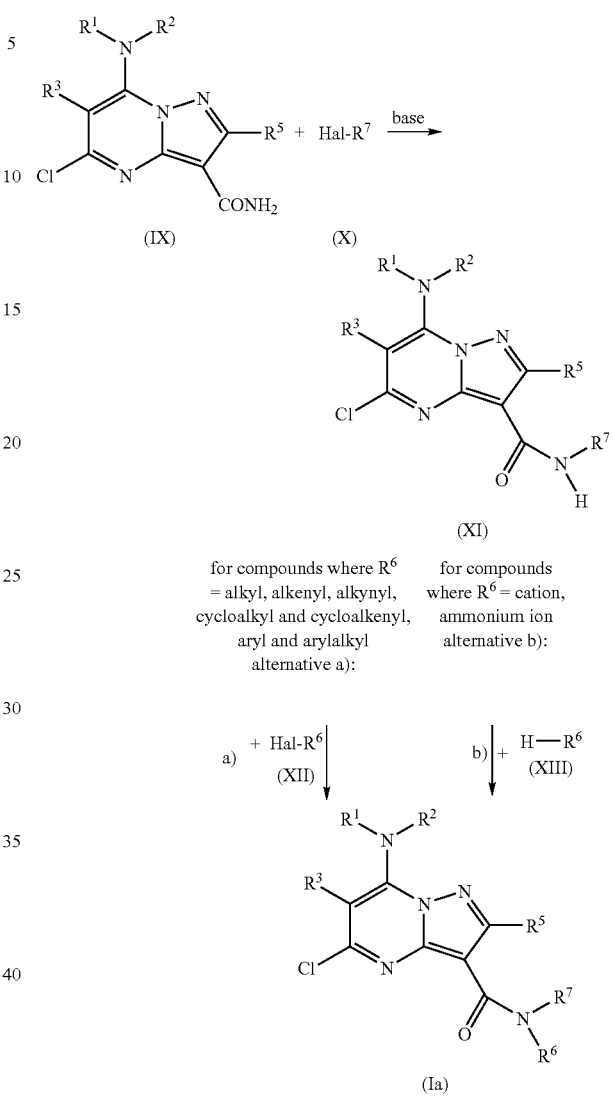

for compounds where $R^6$ = alkyl, alkenyl, alkynyl, cycloalkyl and cycloalkenyl, aryl and arylalkyl alternative a):

for compounds where $R^6$ = cation, ammonium ion alternative b):

The amides of the formula IX in which $R^3$ represents optionally substituted phenyl and a process for their preparation are known from WO 05/0056556. Amides of the formula IX in which $R^3$ represents optionally substituted heterocyclyl can be prepared by reacting the 3-cyanopyrazolopyrimidines known from WO 05/000851 analogously to the process given in WO 05/0056556 to give the corresponding amides of the formula IX. Amides of the formula IX in which $R^3$ represents optionally substituted alkyl, optionally substituted alkenyl, optionally substituted cycloalkyl or optionally substituted cycloalkenyl can be prepared by reacting the 3-cyanopyrazolopyrimidines known from WO 05/056557 analogously to the process given in WO 05/0056556 to give the corresponding amides of the formula IX. The halogen compounds of the formula X (for example acid chlorides, chloroformic half-esters, sulphonyl chlorides, heterocyclically substituted carbonyl chlorides) required for the further reactions are known. They are commercially available or can be prepared by processes which are familiar to the person skilled in the art, as described, for example, in HOUBEN WEYL, Methoden der Organischen Chemie. The halogen compounds of the formula XII (for example alkyl halides, alkenyl halides, alkynyl halides, cycloalkyl halides, cycloalkenyl halides, aryl halides, aralkyl halides) required for the further reactions are likewise known. They are commercially available or can be prepared by processes which are familiar to the person skilled in the art, as described, for example, in HOUBEN WEYL, Methoden der Organischen Chemie. The compounds of the formula XIII (for example metal hydrides, metal hydroxides, amines, where metal represents, for example, alkali metals, alkaline earth metals) required for the further reactions are likewise known. They are commercially available or can be prepared by processes familiar to the person skilled in the art, as described, for example, in HOUBEN WEYL, Methoden der Organischen Chemie.

Novel and thus likewise part of the subject-matter of the present invention is the step-wise conversion of the amides IX with the halogen compounds of the formula X into compounds of the formula XI and the further reaction either with halogen compounds of the formula XII or compounds of the formula XIII to compounds of the formula Ia.

Compounds of the formula (I) in which X represents a cyano group (compounds of the formula Ib in Scheme 3) can be prepared, for example, as shown in Scheme 3 starting with the intermediates (V).

Scheme 3: Process IV

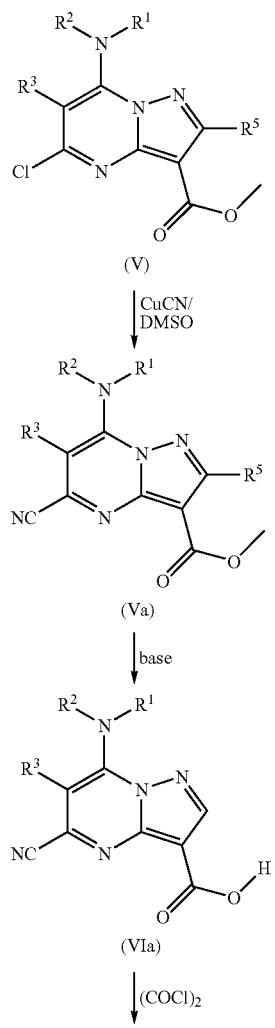

-continued

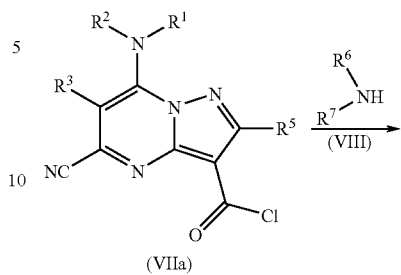

(VIIa)

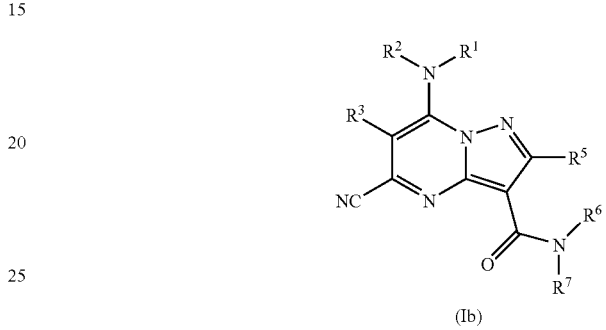

(Ib)

The reaction of compounds of the formula V with cyanide to give compounds of the formula Va is carried out under standard conditions known from the literature (for example: J. Heterocycl. Chem. 1993, 30(4), 993-5). Novel and thus likewise part of the subject-matter of the present invention is the reaction of the acid chlorides VIIa with compounds of the formula VIII to give compounds of the formula Ib.

Compounds of the formula (I) in which X represents an optionally substituted alkyl or phenyl radical (compounds of the formula Ic in Scheme 4) can be prepared as shown in Scheme 4 starting with the esters (II) which are known from the literature (see, for example, U.S. Pat. No. 3,515,715 and U.S. Pat. No. 3,634,391), by reaction with β-ketoesters of the formula XIV which are likewise known from the literature or can be prepared by methods known from the literature (see, for example, EP-A 1 002 788):

Scheme 4: Process V

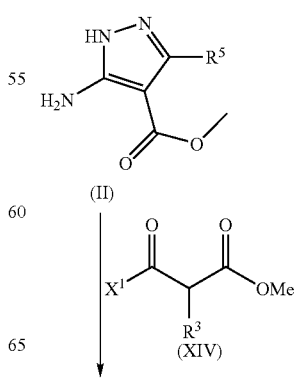

-continued

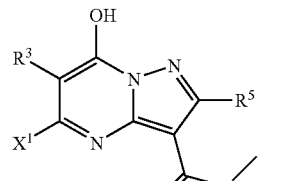
(XV)

↓ POCl₃/PCl₅

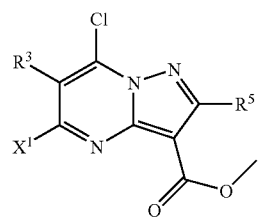
(XVI)

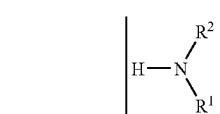

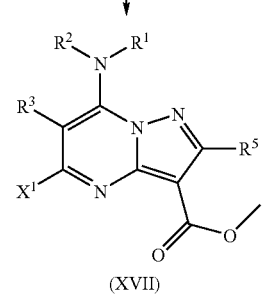
(XVII)

↓ NaOH

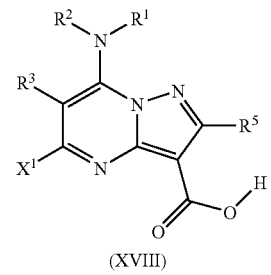
(XVIII)

↓ (COCl)₂

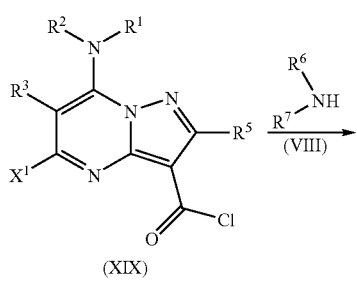
(XIX)

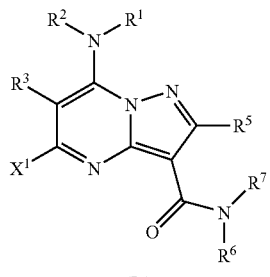
(Ic)

$X^1$ = optionally substituted alkyl, optionally substituted phenyl,

Novel and thus likewise part of the subject-matter of the present invention is the reaction of the acid chlorides XIX with compounds of the formula VIII to give compounds of the formula Ic.

The synthesis of compounds of the formula (I) in which X represents a mercapto, sulphinyl or sulphonyl group (compounds of the formula Id in Scheme 5) is shown in Scheme 5 in an exemplary manner for compounds where $X=S(O)_{0-2}-CH_3$. Here, the cyanoalkenes can be prepared analogously to Gompper et al., Chem. Ber. 1962, 95, 2861-70 or Chauhan et al., Tetrahedron 1976, 32, 1779-87.

Scheme 5: Process VI

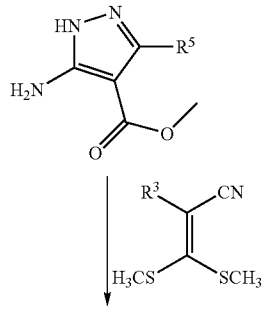

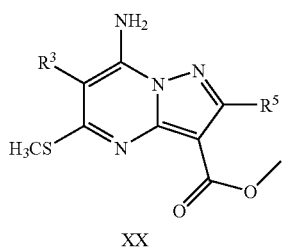
XX

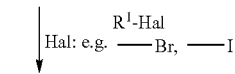

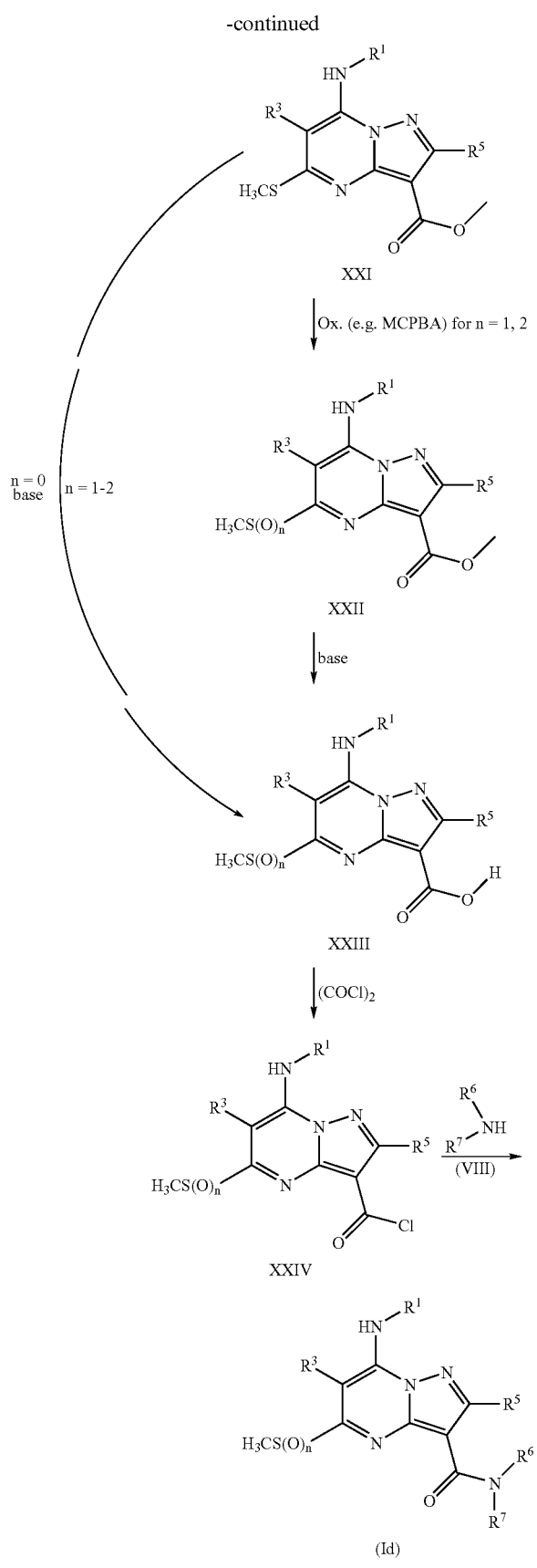

Novel and thus likewise part of the subject-matter of the present invention is the reaction of the acid chlorides XXIV with compounds of the formula VIII to give compounds of the formula Id.

The synthesis of compounds of the formula (I) in which X represents a hydroxyl or an alkoxy group (compounds of the formula Ie in Scheme 6) is shown in Scheme 6 in an exemplary manner for compounds where X=OH and $OCH_3$.

Scheme 6: Process VII

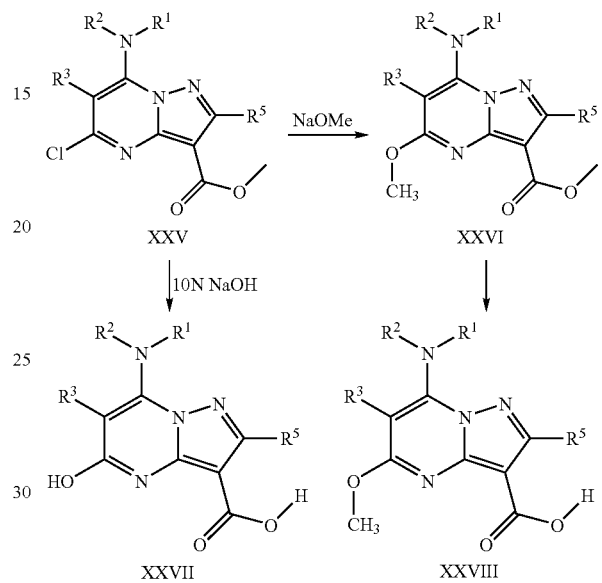

Compounds of the formula V (in which R=Me) (=compounds of the formula XXV, Scheme VII) can be reacted with methoxide (see, for example, Tetrahedron 1996, 52(5), 1735-46) to give methoxy compounds of the formula XXVI. According to methods known from the literature, these compounds are converted into the corresponding carboxylic acids XXVII. Analogously to Schemes 1/2, these are converted further via the corresponding carbonyl chlorides into the corresponding amides.

The processes according to the invention for preparing the compounds of the formula (I) are preferably carried out using one or more reaction auxiliaries.

Suitable reaction auxiliaries are, if appropriate, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethyl-benzylamine, pyridine, 2-methyl-, 3-methyl-, 4-methyl-, 2,4- dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]octane (DABCO), 1,5-diazabicyclo[4.3.0]non-5-ene (DBN), or 1,8-diazabicyclo[5.4.0]undec-7-ene (DBU).

The processes according to the invention are preferably carried out using one or more diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone or methyl isobutyl ketone, esters, such as methyl acetate or ethyl acetate, nitriles, such as, for example, acetonitrile or propionitrile, amides, such as, for example, dimethylformamide, dimethylacetamide and N-methylpyrrolidone, and also dimethyl sulphoxide, tetramethylene sulphone and hexamethylphosphoric triamide.

The reaction temperatures in the processes according to the invention can be varied within a relatively wide range. In general, the processes are carried out at temperatures between 0° C. and 250° C., preferably at temperatures between 10° C. and 185° C.

The processes according to the invention are generally carried out under atmospheric pressure. However, it is also possible to operate under elevated or reduced pressure.

For carrying out the processes according to the invention, the starting materials required in each case are generally employed in approximately equimolar amounts. However, it is also possible to use a relatively large excess of one of the components employed in each case. Work-up in the processes according to the invention is in each case carried out by customary methods (cf. the Preparation Examples).

The compounds according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;* diseases caused by powdery mildew pathogens, such as, for example

*Blumeria* species such as, for example, *Blumeria graminis;*

*Podosphaera* species such as, for example, *Podosphaera leucotricha;*

*Sphaerotheca* species such as, for example, *Sphaerotheca fuliginea;*

*Uncinula* species such as, for example, *Uncinula necator;* diseases caused by rust pathogens such as, for example,

*Gymnosporangium* species such as, for example, *Gymnosporangium sabinae*

*Hemileia* species such as, for example, *Hemileia vastatrix;*

*Phakopsora* species such as, for example, *Phakopsora pachyrhizi* and *Phakopsora meibomiae;*

*Puccinia* species such as, for example, *Puccinia recondita;*

*Uromyces* species such as, for example, *Uromyces appendiculatus;* diseases caused by pathogens from the Oomycetene group such as, for example,

*Bremia* species such as, for example, *Bremia lactucae;*

*Peronospora* species such as, for example, *Peronospora pisi* or *P. brassicae;*

*Phytophthora* species such as, for example, *Phytophthora infestans;*

*Plasmopara* species such as, for example, *Plasmopara viticola;*

*Pseudoperonospora* species such as, for example, *Pseudoperonospora humuli* or *Pseudoperonospora cubensis;*

*Pythium* species such as, for example, *Pythium ultimum;* leaf spot diseases and leaf wilts caused by, for example,

*Alternaria* species such as, for example, *Alternaria solani;*

*Cercospora* species such as, for example, *Cercospora beticola;*

*Cladiosporum* species such as, for example, *Cladiosporium cucumerinum;*

*Cochliobolus* species such as, for example, *Cochliobolus sativus*

(conidial form: *Drechslera*, syn: *Helminthosporium*);

*Colletotrichum* species such as, for example, *Colletotrichum lindemuthanium;*

*Cycloconium* species such as, for example, *Cycloconium oleaginum;*

*Diaporthe* species such as, for example, *Diaporthe citri;*

*Elsinoe* species such as, for example, *Elsinoe fawcettii;*

*Gloeosporium* species such as, for example, *Gloeosporium laeticolor;*

*Glomerella* species such as, for example, *Glomerella cingulata;*

*Guignardia* species such as, for example, *Guignardia bidwelli;*

*Leptosphaeria* species such as, for example, *Leptosphaeria maculans;*

*Magnaporthe* species such as, for example, *Magnaporthe grisea;*

*Mycosphaerella* species such as, for example, *Mycosphaerelle graminicola;*

*Phaeosphaeria* species such as, for example, *Phaeosphaeria nodorum;*

*Pyrenophora* species such as, for example, *Pyrenophora teres*;

*Ramularia* species such as, for example, *Ramularia collo-cygni*;

*Rhynchosporium* species such as, for example, *Rhynchosporium secalis*;

*Septoria* species such as, for example, *Septoria apii*;

*Typhula* species such as, for example, *Typhula incamata*;

*Venturia* species such as, for example, *Venturia inaequalis*;

root and stem diseases caused by, for example,

*Corticium* species such as, for example, *Corticium graminearum*;

*Fusarium* species such as, for example, *Fusarium oxysporum*;

*Gaeumannomyces* species such as, for example, *Gaeumannomyces graminis*;

*Rhizoctonia* species such as, for example, *Rhizoctonia solani*;

*Tapesia* species such as, for example, *Tapesia acuformis*;

*Thielaviopsis* species such as, for example, *Thielaviopsis basicola*;

ear and panicle diseases (including maize cobs), caused by, for example,

*Alternaria* species such as, for example, *Alternaria* spp.;

*Aspergillus* species such as, for example, *Aspergillus flavus*;

*Cladosporium* species such as, for example, *Cladosporium* spp.;

*Claviceps* species such as, for example, *Claviceps purpurea*;

*Fusarium* species such as, for example, *Fusarium culmorum*;

*Gibberella* species such as, for example, *Gibberella zeae*;

*Monographella* species such as, for example, *Monographella nivalis*;

diseases caused by smuts such as, for example,

*Sphacelotheca* species such as, for example, *Sphacelotheca reiliana*;

*Tilletia* species such as, for example, *Tilletia caries*;

*Urocystis* species such as, for example, *Urocystis occulta*;

*Ustilago* species such as, for example, *Ustilago nuda*;

fruit rots caused by, for example,

*Aspergillus* species such as, for example, *Aspergillus flavus*;

*Botrytis* species such as, for example, *Botrytis cinerea*;

*Penicillium* species such as, for example, *Penicillium expansum*;

*Sclerotinia* species such as, for example, *Sclerotinia sclerotiorum*;

*Verticilium* species such as, for example, *Verticilium alboatrum*;

seed- and soil-borne rot and wilts, and seedling diseases, caused by, for example,

*Fusarium* species such as, for example, *Fusarium culmorum*;

*Phytophthora* species such as, for example, *Phytophthora cactorum*;

*Pythium* species such as, for example, *Pythium ultimum*;

*Rhizoctonia* species such as, for example, *Rhizoctonia solani*;

*Sclerotium* species such as, for example, *Sclerotium rolfsii*;

cankers, galls and witches' broom disease, caused by, for example,

*Nectria* species such as, for example, *Nectria galligena*;

wilts caused by, for example,

*Monilinia* species such as, for example, *Monilinia laxa*;

deformations of leaves, flowers and fruits, caused by, for example,

*Taphrina* species such as, for example, *Taphrina deformans*;

degenerative diseases of woody species, caused by, for example,

*Esca* species such as, for example, *Phaemoniella clamydospora*;

diseases of inflorescences and seeds, caused by, for example,

*Botrytis* species such as, for example, *Botrytis cinerea*;

diseases of the plant tubers, caused by, for example,

*Rhizoctonia* species such as, for example, *Rhizoctonia solani*.

The following diseases of soybeans can preferably be controlled:

Fungal diseases on leaves, stems, pods and seeds caused by, for example, alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*);

fungal diseases on roots and the stem base caused by, for example, black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also show a strong invigorating action in plants. Accordingly, they are suitable for mobilizing the internal defences of the plant against attack by unwanted microorganisms.

In the present context, plant-invigorating (resistance-inducing) compounds are to be understood as meaning substances which are capable of stimulating the defence system of plants such that, when the treated plants are subsequently inoculated with unwanted microorganisms, they display substantial resistance to these microorganisms.

In the present case, unwanted microorganisms are to be understood as meaning phytopathogenic fungi and bacteria. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be employed with particularly good results for controlling cereal diseases, such as, for example, against *Erysiphe* species, and of diseases in viticulture and in the cultivation of fruit and vegetables, such as, for example, against *Botrytis, Venturia, Sphaerotheca* and *Podosphaera* species.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

*Alternaria*, such as *Alternaria tenuis*,

*Aspergillus*, such as *Aspergillus niger*,

*Chaetomium*, such as *Chaetomium globosum*,

*Coniophora*, such as *Coniophora puetana*,

*Lentinus*, such as *Lentinus tigrinus*,

*Penicillium*, such as *Penicillium glaucum*,

*Polyporus*, such as *Polyporus versicolor*,

*Aureobasidium*, such as *Aureobasidium pullulans*,

*Sclerophoma*, such as *Sclerophoma pityophila*,

*Trichoderma*, such as *Trichoderma viride*,

*Escherichia*, such as *Escherichia coli*,

*Pseudomonas*, such as *Pseudomonas aeruginosa*, and

*Staphylococcus*, such as *Staphylococcus aureus*.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, pumice, marble, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:

1. Nucleic Acid Synthesis Inhibitors
   benalaxyl, benalaxyl-M, bupirimate, chiralaxyl, clozylacon, dimethirimol, ethirimol, furalaxyl, hymexazol, metalaxyl-M, ofurace, oxadixyl, oxolinic acid 2. Mitosis and Cell Division Inhibitors
   benomyl, carbendazim, diethofencarb, fuberidazole, pencycuron, thiabendazole, thiophanate-methyl, zoxamide 3. Inhibitors of the Respiratory Chain
   3.1 Complex I
   diflumetorim
   3.2 Complex II
   boscalid, carboxin, fenfuram, flutolanil, furametpyr, mepronil, oxycarboxin, penthiopyrad, thifluzamide
   3.3 Complex III
   azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin 3.4 Decouplers
   dinocap, fluazinam
   3.5 ATP production inhibitors
   fentin acetate, fentin chloride, fentin hydroxide, silthiofam 4. Amino Acid and Protein Biosynthesis Inhibitors
   andoprim, blasticidin-S, cyprodinil, kasugamycin, kasugamycin hydrochloride hydrate, mepanipyrim, pyrimethanil 5. Signal Transduction Inhibitors
   fenpiclonil, fludioxonil, quinoxyfen 6. Lipid and Membrane Synthesis Inhibitors
   chlozolinate, iprodione, procymidone, vinclozolin
   pyrazophos, edifenphos, iprobenfos (IBP), isoprothiolane
   tolclofos-methyl, biphenyl
   iodocarb, propamocarb, propamocarb hydrochloride 7. Inhibitors of Ergosterol Biosynthesis
   fenhexamid,
   azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidol, nuarimol, pyrifenox, triforine, pefurazoate, prochloraz, triflumizole, viniconazole,
   aldimorph, dodemorph, dodemorph acetate, fenpropimorph, tridemorph, fenpropidin, spiroxamine,
   naftifine, pyributicarb, terbinafine 8. Cell Wall Synthesis Inhibitors
   benthiavalicarb, bialaphos, dimethomorph, flumorph, iprovalicarb, polyoxins, polyoxorim, validamycin A 9. Melanin Biosynthesis Inhibitors
   capropamid, diclocymet, fenoxanil, phthalide, pyroquilon, tricyclazole 10. Resistance Inductors
    acibenzolar-S-methyl, probenazole, tiadinil 11. Compounds with Multisite Activity
    captafol, captan, chlorothalonil, copper salts, such as: copper hydroxide, copper naphthenate, copper oxychloride, copper sulphate, copper oxide, oxine copper and Bordeaux mixture, dichlofluanid, dithianon, dodine, dodine free base, ferbam, fluorofolpet, folpet, fosetyl-Al, guazatine, guazatine acetate, iminoctadine, iminoctadine albesilate, iminoctadine triacetate, mancopper, mancozeb, maneb, metiram, metiram zinc, propineb, sulphur and sulphur preparations comprising calcium polysulphide, thiram, tolylfluanid, zineb, ziram 12. Unknown
    amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fluopicolide, fluoroimide, hexachlorobenzene, 8-hydroxyquinoline sulphate, irumamycin, methasulfocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamid, zarilamid and 2,3,5,6-tetrachloro-4-(methylsulphonyl)pyridine, N-(4-chloro-2-nitrophenyl)-N-ethyl-4-methylbenzenesulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethyl-isoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl-[(4-methoxyphenyl)imino]methyl]thio]methyl]-α-(methoxymethylene)benzyl acetate, 4-chloro-α-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulphonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl]ethylidene]amino]oxy]methyl]-α-(methoxyimino)-N-methyl-α-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

1. Acetylcholinesterase (AChE) Inhibitors 1.1 carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)

1.2 organophosphates (for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-s-methyl, demeton-s-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemetonmethyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium Channel Modulators/Blockers of Voltage-Gated Sodium Channels 2.1 pyrethroids (for example acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cyclopothrin, cyfluthrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralomethrin, trans-fluthrin, ZXI 8901, pyrethrins (pyrethrum))

2.2 oxadiazines (for example indoxacarb)

3. Acetylcholine Receptor Agonists/Antagonists 3.1 chloronicotinyls/neonicotinoids (for example acetamiprid, clothianidin, dinotefuran, imidacloprid, nitenpyram, nithiazine, thiacloprid, thiamethoxam)

3.2 nicotine, bensultap, cartap

4. Acetylcholine Receptor Modulators 4.1 spinosyns (for example spinosad)

5. Antagonists of GABA-Gated Chloride Channels 5.1 cyclodiene organochlorines (for example camphechlor, chlordane, endosulfan, gamma-HCH, HCH, heptachlor, lindane, methoxychlor)

5.2 fiproles (for example acetoprole, ethiprole, fipronil, vaniliprole)

6. Chloride Channel Activators 6.1 mectins (for example abamectin, avermectin, emamectin, emamectin-benzoate, ivermectin, milbemectin, milbemycin)

7. Juvenile Hormone Mimetics (for example diofenolan, epofenonane, fenoxycarb, hydroprene, kinoprene, methoprene, pyriproxifen, triprene)

8. Ecdyson Agonists/Disruptors 8.1 diacylhydrazines (for example chromafenozide, halofenozide, methoxyfenozide, tebufenozide)

9. Chitin biosynthesis inhibitors 9.1 benzoylureas (for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron)

9.2 buprofezin
9.3 cyromazine

10. Inhibitors of Oxidative Phosphorylation, ATP Disruptors
    10.1 diafenthiuron
    10.2 organotins (for example azocyclotin, cyhexatin, fenbutatin-oxide)

11. Decouplers of Oxidative Phosphorylation Acting by Interrupting the H-Proton Gradient
    11.1 pyrroles (for example chlorfenapyr)
    11.2 dinitrophenols (for example binapacryl, dinobuton, dinocap, DNOC)

12. Site-I Electron Transport Inhibitors
    12.1 METIs (for example fenazaquin, fenpyroximate, pyrimidifen, pyridaben, tebufenpyrad, tolfenpyrad)
    12.2 hydramethylnone
    12.3 dicofol 13. Site-II Electron Transport Inhibitors
    13.1 rotenone 14. Site-III Electron Transport Inhibitors
    14.1 acequinocyl, fluacrypyrim 15. Microbial Disruptors of the Insect Gut Membrane
    *Bacillus thuringiensis* Strains 16. Inhibitors of Fat Synthesis
    16.1 tetronic acids (for example spirodiclofen, spiromesifen)
    16.2 tetramic acids [for example 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS Reg. No.: 203313-25-1)]

17. Carboxamides
    (for example flonicamid)

18. Octopaminergic Agonists
    (for example amitraz)

19. Inhibitors of Magnesium-Stimulated ATPase
    (for example propargite)

20. Phthalamides
    (for example $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide (CAS Reg. No.: 272451-65-7), flubendiamide)

21. Nereistoxin Analogues
    (for example thiocyclam hydrogen oxalate, thiosultap-sodium)

22. Biologicals, Hormones or Pheromones
    (for example azadirachtin, *Bacillus* spec., *Beauveria* spec., Codlemone, *Metarrhizium* spec., *Paecilomyces* spec., Thuringiensin, *Verticillium* spec.)

23. Active Compounds with Unknown or Unspecific Mechanisms of Action
    23.1 fumigants (for example aluminium phosphide, methyl bromide, sulphuryl fluoride)
    23.2 selective antifeedants (for example cryolite, flonicamid, pymetrozine)
    23.3 mite growth inhibitors (for example clofentezine, etoxazole, hexythiazox)
    23.4 amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo-isomer (CAS Reg. No. 185984-60-5) (cf. WO 96/37494, WO 98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5 000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are particularly emphasized are increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The compounds of the formula (I) according to the invention are furthermore suitable for suppressing the growth of tumour cells in humans and mammals. This is based on an interaction of the compounds according to the invention with tubulin and microtubuli and by promoting microtubuli polymerization.

Microtubuli play a key role in the regulation of the structure, the metabolism and the division of cells. Within the cells, tubulin is polymerized in the microtubuli which form mitotic spindles. The microtubuli are depolymerized once the purpose of the mitotic spindles has been accomplished. Active compounds which disrupt polymerization or depolymerization of the microtubuli in neoplastic cells, thus inhibiting the proliferation of these cells, belong to the most effective chemotherapeutic anticancer agents currently available. The best-known examples of these are the discodermolides and epothilones (Nicolaou et al., Angew. Chem. 1998, 110, 2120-2153) and also paclitaxel (Taxol).

For this purpose, it is possible to administer an effective amount of one or more compounds of the formula (I) or pharmaceutically acceptable salts thereof.

Compounds of the formula (I) can be used for treating a large number of types of cancer and other proliferation diseases. Examples of such disorders are:

carcinomas, including carcinomas of the bladder, breast, colon, kidneys, liver, lungs, ovaries, pancreas, stomach, cervix, thyroid and skin, including squamous carcinomas;

haematopoetic tumours of the lymphoid cell line, including leukaemias, acute lymphocytic leukaemias, acute lymphoblastic leukaemias, B-cell lymphomas, T-cell lymphomas, Hodgkin lymphomas, non-Hodgkin lymphomas, hairy cell lymphomas and Burketts lymphomas;

haematopoetic tumours of the myeloid cell line, including acute and chronic myelogenic leukaemias and promyelocytic leukaemias;

tumours of mesenchymal origin, including fibrosarcomas and rhabdomyosarcomas;

tumours of the central and peripheral nervous system, including astrocytomas, neuroblastomas, gliomas and schwannomas;

tumours of mesenchymal origin, including fibrosarcomas, rhabdomyosarcomas and osteosarcomas; and other tumours, including melanomas, seminomas, teratocarcinomas, neuroblastomas, gliomas, Xenoderma pigmentosum, keratoactanthomas and follicular thyroid carcinomas.

The effective amount of a compound of the formula I can be determined by a person of average skill in the art and includes exemplary dosage amounts for a human of about 0.05 to 200 mg/kg/day which can be administered in a single dose or in the form of individual separate doses, such as 1 to 4 times per day. Preferably, the compounds are administered in a dosage of less than 100 mg/kg/day, in a single dose or in 2 to 4 separate doses. It is evident that the specific dose and the dosage frequency for a certain patient can be varied and depend on a large number of factors, including the effectiveness of the particular compound used, the metabolic stability and the duration of action of this compound, the species, the age, the body weight, the general state of health, the sex and the diet of the patient, the mode and the time of administration, the elimination rate, the medicament combination and the severity of the particular disorder.

Thus, the present invention provides a medicament for humans which comprises at least one compound of the formula (I) and which allows the treatment of cancer and other proliferation diseases, in an amount effective in this context, and a pharmaceutically acceptable carrier or a pharmaceutically acceptable diluent. The compositions according to the invention may comprise other therapeutic agents as described below and can be formulated using, for example, customary solid or liquid carriers or diluents, such as pharmaceutical additives of a type suitable for the desired administration (for example excipients, binders, preservatives, stabilizers, flavours, etc.), using techniques which are well known in the field of pharmaceutical formulation or required by standard pharmaceutical practice.

The compounds of the formula I can be administered by any suitable means, for example orally, such as in the form of tablets, capsules, granules or powder, sublingually, buccally, parenterally, such as by subcutaneous, intravenous, intramuscular or intrasternal injection or infusion techniques (for example as sterile, injectable, aqueous or non-aqueous solutions or suspensions), nasally, such as by means of an inhalation spray; topically, such as in the form of a cream or ointment, or rectally, such as in the form of suppositories, in dosage unit formulations comprising non-toxic pharmaceutically acceptable carriers or diluents. The compounds of the formula I can be administered, for example, in a form suitable for immediate release or delayed release. Immediate release or delayed release can be achieved by using suitable medicaments comprising the compounds of the formula I or, in particular in the case of a delayed release, by using devices such as subcutaneous implants or osmotic pumps. The compounds of the formula I can also be administered in liposomal form. The active substance can be used, for example, in a composition such as a tablet, a capsule, a solution or suspension comprising about 5 to about 500 mg per unit dose of a compound or a mixture of compounds of the formula or in a topical form (0.01 to 5% by weight of the compound of the formula I, one to five treatments per day). It can be mixed in a customary manner with a physiologically acceptable carrier, excipient, binder, preservative, stabilizer, flavour, etc., or with a topical carrier. The compounds of the formula I can also be formulated in compositions, such as sterile solutions or suspensions, for parenteral administration. About 0.1 to 500 mg of a compound of the formula I can be mixed with a physiologically acceptable carrier, excipient, binder, preservative, stabilizer, etc., in a unit dosage form, as required by standard pharmaceutical practice. The amount of active substance in these compositions or preparations is preferably such that a suitable dosage in the stated range is obtained.

Exemplary compositions for oral administration include suspensions which may comprise, for example, microcrystalline cellulose to increase the bulk, alginic acid or sodium alginate as suspending agent, methylcellulose as viscosity-increasing agent, and sweeteners or flavours such as those known in the art, and tablets with immediate release which may, for example, comprise microcrystalline cellulose, dicalcium phosphate, starch, magnesium stearate and/or lactose and/or other excipients, binders, extenders, peptizers, diluents and glidants, such as those known in the art. Formed tablets, pressed tablets or freeze-dried tablets are exemplary forms which may be used. Exemplary compositions include those which formulate the compounds of the formula I with rapidly soluble solvents, such as mannitol, lactose, sucrose and/or cyclodextrins. Such formulations may also comprise excipients of high molecular weight, such as celluloses (Avicel) or polyethylene glycols (PEG). Such formulations may also contain an excipient to support adhesion to the mucosa, such as hydroxypropylcellulose (HPC), hydroxypropylmethylcellulose (HPMC), sodium carboxymethylcellulose (SCMC), maleic anhydride copolymers (for example Gantrez) and agents for controlling the release, such as polyacrylate copolymer (for example Carbopol 934). Lubricants, glidants, flavours, colorants and stabilizers may also be added, to facilitate preparation and use.

Exemplary compositions for nasal aerosol and inhalation administration include solutions in physiological saline comprising, for example, benzyl alcohol and other suitable preservatives, absorption enhancers to increase the bioavailability and/or other solubilizers and dispersants, such as those known in the art.

Exemplary compositions for parenteral administration include injectable solutions or suspensions which may comprise, for example, suitable non-toxic parenterally acceptable diluents or solvents, such as Cremophor, mannitol, 1,3-butanediol, water, Ringer solution, an isotonic sodium chloride solution or other dispersants; or wetting agents and suspension agents, including synthetic mono- or diglycerides, and fatty acids, including oleic acids.

Exemplary compositions for rectal administration include suppositories which may contain, for example, a suitable non-irritating excipient, such as cocoa butter, synthetic glyceride esters or polyethylene glycols, which are solid at normal temperature but liquefy and/or dissolve in the rectal cavity, releasing the medicament.

Exemplary compositions for topical administration include a topical carrier, such as Plastibase (mineral oil gelated with polyethylene). The compounds of the formula I can be administered topically to treat the plaques associated with psoriasis, for example, and can be formulated as such as a cream or ointment.

The compounds of the formula I can be administered either on their own or in combination with other anticancer and cytotoxic agents and treatments suitable for managing cancer or other proliferation disorders. Particularly useful are anticancer and cytotoxic medicament combinations in which the second chosen medicament acts in a different manner or during a different phase of the cell cycle, for example the S phase, than the present compounds of the formula I which are active during the G2-M phase. Examples of classes of anticancer and cytotoxic agents include alkylating agents, such as nitrogen mustard, alkylsulphonates, nitrosoureas, ethyleneimines and triazenes; antimetabolites, such as folate antagonists, purine analogues and pyrimidine analogues; antibiotics, such as anthracyclines, bleomycins, mitomycin, dactinomycin and plicamycin; enzymes, such as L-aspartase; farnesyl protein transferase inhibitors; hormonal agents, such as glucocorticoids, oestrogens/anti-oestrogens, androgens/antiandrogens, progestins and luteinizing hormone-releasing hormone antagonists, octreotide acetate; microtubulus-destroying agents, such as ectein-ascidins or their analogues and derivatives; microtubulus-stabilizing agents, such as paclitaxel (Taxol), docetaxel (Taxotere) and epothilones A-F or their analogues or derivatives; plant-derived products, such as vinca alkaloids, epipodophyllotoxins, taxanes; and topoisomerase inhibitors; prenyl protein transferase inhibitors; and various agents, such as hydroxyurea, procarbazine, mitotane, hexamethylmelamine, platinum coordination complexes, such as cisplatin and carboplatin; and other agents used as anticancer and cytotoxic agents, such as agents which modify the biological reaction, growth factors, immunomodulators and monoclonal antibodies. The compounds of the formula I can also be used in combination with radiotherapy.

Representative examples of these classes of anticancer and cytotoxic agents include mechlorethamine hydrochloride, cyclophosphamid, chlorambucil, melphalan, ifosfamid, busulfan, carmustine, lomustine, semustine, streptozocin, thiotepa, dacarbazin, methotrexate, thioguanine, mercaptopurine, fludarabine, pentastatin, cladribin, cytarabine, fluorouracil, doxorubicin hydrochloride, daunorubicin, idarubicin, bleomycin sulphate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethasone, gemcitabine hydrochloride, altretamine and topoteca and all analogues or derivatives thereof.

Preferred members of these classes include paclitaxel, cisplatin, carboplatin, doxorubicin, caminomycin, daunorubicin, aminopterin, methotrexate, methopterin, mitomycin C, ecteinascidin 743, porfiromycin, 5-fluorouracil, mercaptopurine, gemcitabine, cytosine arabinoside, podophyllotoxin or podophyllotoxin derivatives, such as etoposide, etoposide phosphate or teniposide, melphalan, vinblastine, vincristine, leurosidine, vindesine and leurosine.

The combinations of the present invention can also be formulated or administered together with other therapeutic agents selected by virtue of their particular usefulness in the administration of therapies associated with the disorders listed above. The compounds of the formula I can be formulated, for example, with agents such as antiemetics and H1 and H2 antihistamines, to prevent nausea, hypersensitivity and stomach irritations.

When used in combination with the compounds of the formula I, the therapeutic agents listed above can be administered in the amounts stated in the Physicians' Desk Reference (PDR) or otherwise determined by a person of average skill.

Novel and thus likewise part of the subject-matter of the present invention is the use of compounds of the formula I as medicaments.

Furthermore novel and thus likewise part of the subject-matter of the present invention is the use of compounds of the formula I for preparing medicaments, in particular medicaments against cancer.

The preparation and the use of the active compounds according to the invention is illustrated by the examples below.

EXAMPLES

Example I

N-[5-Chloro-6-(2,4-dichlorophenyl)-7-isopropylaminopyrazolo[1,5-a]pyrimidine-3-carbonyl]methanesulphonamide 0.95 g of oxalyl chloride and a drop of dimethylformamide were added to a solution of 1 g of 5-chloro-6-(2,4-dichlorophenyl)-7-isopropylaminopyrazolo[1,5-a]pyrimidine-3-carboxylic acid in 20 ml of dichloromethane, and the mixture was stirred until the evolution of gas had ceased. The mixture was then concentrated and taken up again in dichloroethane (5 ml). A solution of 126 mg of methanesulphonamide in 1 ml of pyridine was added dropwise to the resulting solution. After further stirring at room temperature, during which the reaction was monitored by TLC, the reaction was quenched with 1N hydrochloric acid, the mixture was concentrated and the residue was purified chromatographically using n-hexane/ethyl acetate 5:1→3:1. This gave 0.029 g of N-[5-chloro-6-(2,4-dichlorophenyl)-7-isopropylaminopyrazolo[1,5-a]pyrimidine-3-carbonyl]methanesulphonamide (5% of theory).

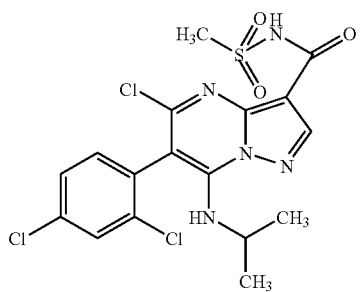

logP*: 3.96

The compounds of the formula (I-a) listed in Table 1 below are or were also obtained analogously to the methods described above.

TABLE 1

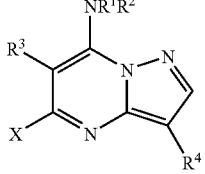

| Ex. No. | R¹ or —R¹⁺R²— | R² | R3 | X | R4 | log p |
|---|---|---|---|---|---|---|
| 1 | CH(CH₃)—C(CH₃)₃ | H | 2-chloro-6-fluorophenyl | Cl | CONHCONHCH₃ | |
| 2 | CH(CH₃)—C(CH₃)₃ | H | 2-chloro-6-fluorophenyl | Cl | CONHSO₂CF₃ | |
| 3 | (R) CH(CH₃)—C(CH₃)₃ | H | 2-chloro-6-fluorophenyl | Cl | CONHSO₂CH₃ | 4.19* |
| 4 | CH(CH₃)—C(CH₃)₃ | H | 2-chloro-6-fluorophenyl | Cl | CONHSO₂CH₂CH₃ | |
| 5 | CH(CH₃)—C(CH₃)₃ | H | 2-chloro-6-fluorophenyl | Cl | (isoxazol-3-ylamino)carbonyl | |
| 6 | CH(CH₃)—C(CH₃)₃ | H | 2-chloro-6-fluorophenyl | Cl | [(4-methyl-4H-1,2,4-triazol-3-yl)amino]carbonyl | |
| 7 | CH(CH₃)—C(CH₃)₃ | H | 2,4,6-trifluorophenyl | Cl | CONHCONHCH₃ | |
| 8 | CH(CH₃)—C(CH₃)₃ | H | 2,4,6-trifluorophenyl | Cl | CONHSO₂CF₃ | |
| 9 | (R) CH(CH₃)—C(CH₃)₃ | H | 2,4,6-trifluorophenyl | Cl | CONHSO₂CH₃ | 4.16 |
| 10 | CH(CH₃)—C(CH₃)₃ | H | 2,4,6-trifluorophenyl | Cl | CONHSO₂CH₂CH₃ | |
| 11 | CH(CH₃)—C(CH₃)₃ | H | 2,4,6-trifluorophenyl | Cl | (isoxazol-3-ylamino)carbonyl | |
| 12 | CH(CH₃)—C(CH₃)₃ | H | 2,4,6-trifluorophenyl | Cl | [(4-methyl-4H-1,2,4-triazol-3-yl)amino]carbonyl | |
| 13 | CH(CH₃)—C(CH₃)₃ | H | 2-chloro-4-fluorophenyl | Cl | CONHCONHCH₃ | |
| 14 | (R) CH(CH₃)—C(CH₃)₃ | H | 2-chloro-4-fluorophenyl | Cl | CONHSO₂CF₃ | 3.77 |
| 15 | (R) CH(CH₃)—C(CH₃)₃ | H | 2-chloro-4-fluorophenyl | Cl | CONHSO₂CH₃ | 4.44 |
| 16 | CH(CH₃)—C(CH₃)₃ | H | 2-chloro-4-fluorophenyl | Cl | CONHSO₂CH₂CH₃ | |
| 17 | CH(CH₃)—C(CH₃)₃ | H | 2-chloro-4-fluorophenyl | Cl | (isoxazol-3-ylamino)carbonyl | |
| 18 | CH(CH₃)—C(CH₃)₃ | H | 2-chloro-4-fluorophenyl | Cl | [(4-methyl-4H-1,2,4-triazol-3-yl)amino]carbonyl | |
| 19 | CH(CH₃)—C(CH₃)₃ | H | 2-chlorophenyl | Cl | CONHCONHCH₃ | |
| 20 | CH(CH₃)—C(CH₃)₃ | H | 2-chlorophenyl | Cl | CONHSO₂CF₃ | |
| 21 | (R) CH(CH₃)—C(CH₃)₃ | H | 2-chlorophenyl | Cl | CONHSO₂CH₃ | 4.36* |
| 22 | CH(CH₃)—C(CH₃)₃ | H | 2-chlorophenyl | Cl | CONHSO₂CH₂CH₃ | |
| 23 | CH(CH₃)—C(CH₃)₃ | H | 2-chlorophenyl | Cl | (isoxazol-3-ylamino)carbonyl | |
| 24 | CH(CH₃)—C(CH₃)₃ | H | 2-chlorophenyl | Cl | [(4-methyl-4H-1,2,4-triazol-3-yl)amino]carbonyl | |
| 25 | CH(CH₃)—C(CH₃)₃ | H | 5-Cl-pyrimidin-4-yl | Cl | CONHCONHCH₃ | |
| 26 | CH(CH₃)—C(CH₃)₃ | H | 5-Cl-pyrimidin-4-yl | Cl | CONHSO₂CF₃ | |
| 27 | CH(CH₃)—C(CH₃)₃ | H | 5-Cl-pyrimidin-4-yl | Cl | CONHSO₂CH₃ | |
| 28 | CH(CH₃)—C(CH₃)₃ | H | 5-Cl-pyrimidin-4-yl | Cl | CONHSO₂CH₂CH₃ | |
| 29 | CH(CH₃)—C(CH₃)₃ | H | 5-Cl-pyrimidin-4-yl | Cl | (isoxazol-3-ylamino)carbonyl | |
| 30 | CH(CH₃)—C(CH₃)₃ | H | 5-Cl-pyrimidin-4-yl | Cl | [(4-methyl-4H-1,2,4-triazol-3-yl)amino]carbonyl | |
| 31 | CH(CH₃)—C(CH₃)₃ | H | 2-chloro-4,6-difluorophenyl | Cl | CONHCONHCH₃ | |
| 32 | CH(CH₃)—C(CH₃)₃ | H | 2-chloro-4,6-difluorophenyl | Cl | CONHSO₂CF₃ | |
| 33 | (R) CH(CH₃)—C(CH₃)₃ | H | 2-chloro-4,6-difluorophenyl | Cl | CONHSO₂CH₃ | 4.38 |
| 34 | CH(CH₃)—C(CH₃)₃ | H | 2-chloro-4,6-difluorophenyl | Cl | CONHSO₂CH₂CH₃ | |
| 35 | CH(CH₃)—C(CH₃)₃ | H | 2-chloro-4,6-difluorophenyl | Cl | (isoxazol-3-ylamino)carbonyl | |
| 36 | CH(CH₃)—C(CH₃)₃ | H | 2-chloro-4,6-difluorophenyl | Cl | [(4-methyl-4H-1,2,4-triazol-3-yl)amino]carbonyl | |
| 37 | CH(CH₃)—C(CH₃)₃ | H | 2,4-dichlorophenyl | Cl | CONHCONHCH₃ | |
| 38 | (R) CH(CH₃)—C(CH₃)₃ | H | 2,4-dichlorophenyl | Cl | CONHSO₂CF₃ | 3.93 |
| 39 | (R) CH(CH₃)—C(CH₃)₃ | H | 2,4-dichlorophenyl | Cl | CONHSO₂CH₃ | 4.89* |
| 40 | CH(CH₃)—C(CH₃)₃ | H | 2,4-dichlorophenyl | Cl | CONHSO₂CH₂CH₃ | |
| 41 | CH(CH₃)—C(CH₃)₃ | H | 2,4-dichlorophenyl | Cl | (isoxazol-3-ylamino)carbonyl | |
| 42 | CH(CH₃)—C(CH₃)₃ | H | 2,4-dichlorophenyl | Cl | [(4-methyl-4H-1,2,4-triazol-3-yl)amino]carbonyl | |
| 43 | CH(CH₃)—C(CH₃)₃ | H | 4-chloro-2,6-difluorophenyl | Cl | CONHCONHCH₃ | |
| 44 | CH(CH₃)—C(CH₃)₃ | H | 4-chloro-2,6-difluorophenyl | Cl | CONHSO₂CF₃ | |
| 45 | (R) CH(CH₃)—C(CH₃)₃ | H | 4-chloro-2,6-difluorophenyl | Cl | CONHSO₂CH₃ | 4.55* |
| 46 | CH(CH₃)—C(CH₃)₃ | H | 4-chloro-2,6-difluorophenyl | Cl | CONHSO₂CH₂CH₃ | |
| 47 | CH(CH₃)—C(CH₃)₃ | H | 4-chloro-2,6-difluorophenyl | Cl | (isoxazol-3-ylamino)carbonyl | |

TABLE 1-continued

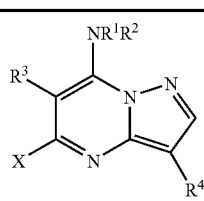

| Ex. No. | R¹ or —R¹⁺R²— | R² | R3 | X | R4 | log p |
|---|---|---|---|---|---|---|
| 48 | CH(CH₃)—C(CH₃)₃ | H | 4-chloro-2,6-difluorophenyl | Cl | [(4-methyl-4H-1,2,4-triazol-3-yl)amino]carbonyl | |
| 49 | CH(CH₃)—C(CH₃)₃ | H | 2,6-difluoro-4-methylphenyl | Cl | CONHCONHCH₃ | |
| 50 | CH(CH₃)—C(CH₃)₃ | H | 2,6-difluoro-4-methylphenyl | Cl | CONHSO₂CF₃ | |
| 51 | (R) CH(CH₃)—C(CH₃)₃ | H | 2,6-difluoro-4-methylphenyl | Cl | CONHSO₂CH₃ | 4.38** |
| 52 | CH(CH₃)—C(CH₃)₃ | H | 2,6-difluoro-4-methylphenyl | Cl | CONHSO₂CH₂CH₃ | |
| 53 | CH(CH₃)—C(CH₃)₃ | H | 2,6-difluoro-4-methylphenyl | Cl | (isoxazol-3-ylamino)carbonyl | |
| 54 | CH(CH₃)—C(CH₃)₃ | H | 2,6-difluoro-4-methylphenyl | Cl | [(4-methyl-4H-1,2,4-triazol-3-yl)amino]carbonyl | |
| 55 | CH(CH₃)—C(CH₃)₃ | H | 2-chloro-5-fluorophenyl | Cl | CONHCONHCH₃ | |
| 56 | CH(CH₃)—C(CH₃)₃ | H | 2-chloro-5-fluorophenyl | Cl | CONHSO₂CF₃ | |
| 57 | CH(CH₃)—C(CH₃)₃ | H | 2-chloro-5-fluorophenyl | Cl | CONHSO₂CH₃ | |
| 58 | CH(CH₃)—C(CH₃)₃ | H | 2-chloro-5-fluorophenyl | Cl | CONHSO₂CH₂CH₃ | |
| 59 | CH(CH₃)—C(CH₃)₃ | H | 2-chloro-5-fluorophenyl | Cl | (isoxazol-3-ylamino)carbonyl | |
| 60 | CH(CH₃)—C(CH₃)₃ | H | 2-chloro-5-fluorophenyl | Cl | [(4-methyl-4H-1,2,4-triazol-3-yl)amino]carbonyl | |
| 61 | CH(CH₃)—C(CH₃)₃ | H | 3-chloro-2-thienyl | Cl | CONHCONHCH₃ | |
| 62 | CH(CH₃)—C(CH₃)₃ | H | 3-chloro-2-thienyl | Cl | CONHSO₂CF₃ | |
| 63 | CH(CH₃)—C(CH₃)₃ | H | 3-chloro-2-thienyl | Cl | CONHSO₂CH₃ | |
| 64 | CH(CH₃)—C(CH₃)₃ | H | 3-chloro-2-thienyl | Cl | CONHSO₂CH₂CH₃ | |
| 65 | CH(CH₃)—C(CH₃)₃ | H | 3-chloro-2-thienyl | Cl | (isoxazol-3-ylamino)carbonyl | |
| 66 | CH(CH₃)—C(CH₃)₃ | H | 3-chloro-2-thienyl | Cl | [(4-methyl-4H-1,2,4-triazol-3-yl)amino]carbonyl | |
| 67 | CH(CH₃)—C(CH₃)₃ | H | phenyl | Cl | CONHCONHCH₃ | |
| 68 | CH(CH₃)—C(CH₃)₃ | H | phenyl | Cl | CONHSO₂CF₃ | |
| 69 | CH(CH₃)—C(CH₃)₃ | H | phenyl | Cl | CONHSO₂CH₃ | |
| 70 | CH(CH₃)—C(CH₃)₃ | H | phenyl | Cl | CONHSO₂CH₂CH₃ | |
| 71 | CH(CH₃)—C(CH₃)₃ | H | phenyl | Cl | (isoxazol-3-ylamino)carbonyl | 4.88** |
| 72 | CH(CH₃)—C(CH₃)₃ | H | phenyl | Cl | [(4-methyl-4H-1,2,4-triazol-3-yl)amino]carbonyl | |
| 73 | CH(CH₃)—C(CH₃)₃ | H | cyclopentyl | Cl | CONHCONHCH₃ | |
| 74 | CH(CH₃)—C(CH₃)₃ | H | cyclopentyl | Cl | CONHSO₂CF₃ | |
| 75 | CH(CH₃)—C(CH₃)₃ | H | cyclopentyl | Cl | CONHSO₂CH₃ | |
| 76 | CH(CH₃)—C(CH₃)₃ | H | cyclopentyl | Cl | CONHSO₂CH₂CH₃ | |
| 77 | CH(CH₃)—C(CH₃)₃ | H | cyclopentyl | Cl | (isoxazol-3-ylamino)carbonyl | |
| 78 | CH(CH₃)—C(CH₃)₃ | H | cyclopentyl | Cl | [(4-methyl-4H-1,2,4-triazol-3-yl)amino]carbonyl | |
| 79 | CH(CH₃)—C(CH₃)₃ | H | sec-butyl | Cl | CONHCONHCH₃ | |
| 80 | CH(CH₃)—C(CH₃)₃ | H | sec-butyl | Cl | CONHSO₂CF₃ | |
| 81 | CH(CH₃)—C(CH₃)₃ | H | sec-butyl | Cl | CONHSO₂CH₃ | |
| 82 | CH(CH₃)—C(CH₃)₃ | H | sec-butyl | Cl | CONHSO₂CH₂CH₃ | |
| 83 | CH(CH₃)—C(CH₃)₃ | H | sec-butyl | Cl | (isoxazol-3-ylamino)carbonyl | |
| 84 | CH(CH₃)—C(CH₃)₃ | H | sec-butyl | Cl | [(4-methyl-4H-1,2,4-triazol-3-yl)amino]carbonyl | |
| 85 | CH(CH₃)(CF₃) | H | 2-chloro-6-fluorophenyl | Cl | CONHCONHCH₃ | |
| 86 | CH(CH₃)(CF₃) | H | 2-chloro-6-fluorophenyl | Cl | CONHSO₂CF₃ | |
| 87 | CH(CH₃)(CF₃) | H | 2-chloro-6-fluorophenyl | Cl | CONHSO₂CH₃ | |
| 88 | CH(CH₃)(CF₃) | H | 2-chloro-6-fluorophenyl | Cl | CONHSO₂CH₂CH₃ | |
| 89 | CH(CH₃)(CF₃) | H | 2-chloro-6-fluorophenyl | Cl | (isoxazol-3-ylamino)carbonyl | |
| 90 | CH(CH₃)(CF₃) | H | 2-chloro-6-fluorophenyl | Cl | [(4-methyl-4H-1,2,4-triazol-3-yl)amino]carbonyl | |
| 91 | CH(CH₃)(CF₃) | H | 2,4,6-trifluorophenyl | Cl | CONHCONHCH₃ | |
| 92 | CH(CH₃)(CF₃) | H | 2,4,6-trifluorophenyl | Cl | CONHSO₂CF₃ | |
| 93 | CH(CH₃)(CF₃) | H | 2,4,6-trifluorophenyl | Cl | CONHSO₂CH₃ | |
| 94 | CH(CH₃)(CF₃) | H | 2,4,6-trifluorophenyl | Cl | CONHSO₂CH₂CH₃ | |
| 95 | CH(CH₃)(CF₃) | H | 2,4,6-trifluorophenyl | Cl | (isoxazol-3-ylamino)carbonyl | |
| 96 | CH(CH₃)(CF₃) | H | 2,4,6-trifluorophenyl | Cl | [(4-methyl-4H-1,2,4-triazol-3-yl)amino]carbonyl | |
| 97 | CH(CH₃)(CF₃) | H | 2-chloro-4-fluorophenyl | Cl | CONHCONHCH₃ | |
| 98 | CH(CH₃)(CF₃) | H | 2-chloro-4-fluorophenyl | Cl | CONHSO₂CF₃ | |

TABLE 1-continued

Structure: 7-(NR¹R²)-6-R³-5-X-3-R⁴-pyrazolo[1,5-a]pyrimidine

| Ex. No. | R¹ or —R¹⁺R²— | R² | R3 | X | R4 | log p |
|---|---|---|---|---|---|---|
| 99 | CH(CH₃)(CF₃) | H | 2-chloro-4-fluorophenyl | Cl | CONHSO₂CH₃ | |
| 100 | CH(CH₃)(CF₃) | H | 2-chloro-4-fluorophenyl | Cl | CONHSO₂CH₂CH₃ | |
| 101 | CH(CH₃)(CF₃) | H | 2-chloro-4-fluorophenyl | Cl | (isoxazol-3-ylamino)carbonyl | |
| 102 | CH(CH₃)(CF₃) | H | 2-chloro-4-fluorophenyl | Cl | [(4-methyl-4H-1,2,4-triazol-3-yl)amino]carbonyl | |
| 103 | CH(CH₃)(CF₃) | H | 2-chlorophenyl | Cl | CONHCONHCH₃ | |
| 104 | CH(CH₃)(CF₃) | H | 2-chlorophenyl | Cl | CONHSO₂CF₃ | |
| 105 | CH(CH₃)(CF₃) | H | 2-chlorophenyl | Cl | CONHSO₂CH₃ | |
| 106 | CH(CH₃)(CF₃) | H | 2-chlorophenyl | Cl | CONHSO₂CH₂CH₃ | |
| 107 | CH(CH₃)(CF₃) | H | 2-chlorophenyl | Cl | (isoxazol-3-ylamino)carbonyl | |
| 108 | CH(CH₃)(CF₃) | H | 2-chlorophenyl | Cl | [(4-methyl-4H-1,2,4-triazol-3-yl)amino]carbonyl | |
| 109 | CH(CH₃)(CF₃) | H | 5-Cl-pyrimidin-4-yl | Cl | CONHCONHCH₃ | |
| 110 | CH(CH₃)(CF₃) | H | 5-Cl-pyrimidin-4-yl | Cl | CONHSO₂CF₃ | |
| 111 | CH(CH₃)(CF₃) | H | 5-Cl-pyrimidin-4-yl | Cl | CONHSO₂CH₃ | |
| 112 | CH(CH₃)(CF₃) | H | 5-Cl-pyrimidin-4-yl | Cl | CONHSO₂CH₂CH₃ | |
| 113 | CH(CH₃)(CF₃) | H | 5-Cl-pyrimidin-4-yl | Cl | (isoxazol-3-ylamino)carbonyl | |
| 114 | CH(CH₃)(CF₃) | H | 5-Cl-pyrimidin-4-yl | Cl | [(4-methyl-4H-1,2,4-triazol-3-yl)amino]carbonyl | |
| 115 | CH(CH₃)(CF₃) | H | 2-chloro-4,6-difluorophenyl | Cl | CONHCONHCH₃ | |
| 116 | CH(CH₃)(CF₃) | H | 2-chloro-4,6-difluorophenyl | Cl | CONHSO₂CF₃ | |
| 117 | (S) CH(CH₃)(CF₃) | H | 2-chloro-4,6-difluorophenyl | Cl | CONHSO₂CH₃ | 3.56* |
| 118 | CH(CH₃)(CF₃) | H | 2-chloro-4,6-difluorophenyl | Cl | CONHSO₂CH₂CH₃ | |
| 119 | CH(CH₃)(CF₃) | H | 2-chloro-4,6-difluorophenyl | Cl | (isoxazol-3-ylamino)carbonyl | |
| 120 | CH(CH₃)(CF₃) | H | 2-chloro-4,6-difluorophenyl | Cl | [(4-methyl-4H-1,2,4-triazol-3-yl)amino]carbonyl | |
| 121 | CH(CH₃)(CF₃) | H | 2,4-dichlorophenyl | Cl | CONHCONHCH₃ | |
| 122 | CH(CH₃)(CF₃) | H | 2,4-dichlorophenyl | Cl | CONHSO₂CF₃ | |
| 123 | (S) CH(CH₃)(CF₃) | H | 2,4-dichlorophenyl | Cl | CONHSO₂CH₃ | 3.99 |
| 124 | CH(CH₃)(CF₃) | H | 2,4-dichlorophenyl | Cl | CONHSO₂CH₂CH₃ | |
| 125 | CH(CH₃)(CF₃) | H | 2,4-dichlorophenyl | Cl | (isoxazol-3-ylamino)carbonyl | |
| 126 | CH(CH₃)(CF₃) | H | 2,4-dichlorophenyl | Cl | [(4-methyl-4H-1,2,4-triazol-3-yl)amino]carbonyl | |
| 127 | CH(CH₃)(CF₃) | H | 4-chloro-2,6-difluorophenyl | Cl | CONHCONHCH₃ | |
| 128 | CH(CH₃)(CF₃) | H | 4-chloro-2,6-difluorophenyl | Cl | CONHSO₂CF₃ | |
| 129 | CH(CH₃)(CF₃) | H | 4-chloro-2,6-difluorophenyl | Cl | CONHSO₂CH₃ | |
| 130 | CH(CH₃)(CF₃) | H | 4-chloro-2,6-difluorophenyl | Cl | CONHSO₂CH₂CH₃ | |
| 131 | CH(CH₃)(CF₃) | H | 4-chloro-2,6-difluorophenyl | Cl | (isoxazol-3-ylamino)carbonyl | |
| 132 | CH(CH₃)(CF₃) | H | 4-chloro-2,6-difluorophenyl | Cl | [(4-methyl-4H-1,2,4-triazol-3-yl)amino]carbonyl | |
| 133 | CH(CH₃)(CF₃) | H | 2,6-difluoro-4-methylphenyl | Cl | CONHCONHCH₃ | |
| 134 | CH(CH₃)(CF₃) | H | 2,6-difluoro-4-methylphenyl | Cl | CONHSO₂CF₃ | |
| 135 | CH(CH₃)(CF₃) | H | 2,6-difluoro-4-methylphenyl | Cl | CONHSO₂CH₃ | |
| 136 | CH(CH₃)(CF₃) | H | 2,6-difluoro-4-methylphenyl | Cl | CONHSO₂CH₂CH₃ | |
| 137 | CH(CH₃)(CF₃) | H | 2,6-difluoro-4-methylphenyl | Cl | (isoxazol-3-ylamino)carbonyl | |
| 138 | CH(CH₃)(CF₃) | H | 2,6-difluoro-4-methylphenyl | Cl | [(4-methyl-4H-1,2,4-triazol-3-yl)amino]carbonyl | |
| 139 | CH(CH₃)(CF₃) | H | 2-chloro-5-fluorophenyl | Cl | CONHCONHCH₃ | |
| 140 | CH(CH₃)(CF₃) | H | 2-chloro-5-fluorophenyl | Cl | CONHSO₂CF₃ | |
| 141 | CH(CH₃)(CF₃) | H | 2-chloro-5-fluorophenyl | Cl | CONHSO₂CH₃ | |

TABLE 1-continued

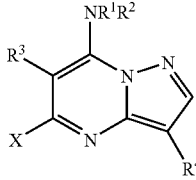

| Ex. No. | R1 or —R1+R2— | R2 | R3 | X | R4 | log p |
|---|---|---|---|---|---|---|
| 142 | CH(CH3)(CF3) | H | 2-chloro-5-fluorophenyl | Cl | CONHSO2CH2CH3 | |
| 143 | CH(CH3)(CF3) | H | 2-chloro-5-fluorophenyl | Cl | (isoxazol-3-ylamino)carbonyl | |
| 144 | CH(CH3)(CF3) | H | 2-chloro-5-fluorophenyl | Cl | [(4-methyl-4H-1,2,4-triazol-3-yl)amino]carbonyl | |
| 145 | CH(CH3)(CF3) | H | 3-chloro-2-thienyl | Cl | CONHCONHCH3 | |
| 146 | CH(CH3)(CF3) | H | 3-chloro-2-thienyl | Cl | CONHSO2CF3 | |
| 147 | CH(CH3)(CF3) | H | 3-chloro-2-thienyl | Cl | CONHSO2CH3 | |
| 148 | CH(CH3)(CF3) | H | 3-chloro-2-thienyl | Cl | CONHSO2CH2CH3 | |
| 149 | CH(CH3)(CF3) | H | 3-chloro-2-thienyl | Cl | (isoxazol-3-ylamino)carbonyl | |
| 150 | CH(CH3)(CF3) | H | 3-chloro-2-thienyl | Cl | [(4-methyl-4H-1,2,4-triazol-3-yl)amino]carbonyl | |
| 151 | CH(CH3)(CF3) | H | phenyl | Cl | CONHCONHCH3 | |
| 152 | CH(CH3)(CF3) | H | phenyl | Cl | CONHSO2CF3 | |
| 153 | CH(CH3)(CF3) | H | phenyl | Cl | CONHSO2CH3 | |
| 154 | CH(CH3)(CF3) | H | phenyl | Cl | CONHSO2CH2CH3 | |
| 155 | CH(CH3)(CF3) | H | phenyl | Cl | (isoxazol-3-ylamino)carbonyl | |
| 156 | CH(CH3)(CF3) | H | phenyl | Cl | [(4-methyl-4H-1,2,4-triazol-3-yl)amino]carbonyl | |
| 157 | CH(CH3)(CF3) | H | cyclopentyl | Cl | CONHCONHCH3 | |
| 158 | CH(CH3)(CF3) | H | cyclopentyl | Cl | CONHSO2CF3 | |
| 159 | CH(CH3)(CF3) | H | cyclopentyl | Cl | CONHSO2CH3 | |
| 160 | CH(CH3)(CF3) | H | cyclopentyl | Cl | CONHSO2CH2CH3 | |
| 161 | CH(CH3)(CF3) | H | cyclopentyl | Cl | (isoxazol-3-ylamino)carbonyl | |
| 162 | CH(CH3)(CF3) | H | cyclopentyl | Cl | [(4-methyl-4H-1,2,4-triazol-3-yl)amino]carbonyl | |
| 163 | CH(CH3)(CF3) | H | sec-butyl | Cl | CONHCONHCH3 | |
| 164 | CH(CH3)(CF3) | H | sec-butyl | Cl | CONHSO2CF3 | |
| 165 | CH(CH3)(CF3) | H | sec-butyl | Cl | CONHSO2CH3 | |
| 166 | CH(CH3)(CF3) | H | sec-butyl | Cl | CONHSO2CH2CH3 | |
| 167 | CH(CH3)(CF3) | H | sec-butyl | Cl | (isoxazol-3-ylamino)carbonyl | |
| 168 | CH(CH3)(CF3) | H | sec-butyl | Cl | [(4-methyl-4H-1,2,4-triazol-3-yl)amino]carbonyl | |
| 169 | CH(CH3)—CH(CH3)2 | H | 2-chloro-6-fluorophenyl | Cl | CONHCONHCH3 | |
| 170 | CH(CH3)—CH(CH3)2 | H | 2-chloro-6-fluorophenyl | Cl | CONHSO2CF3 | |
| 171 | (R) CH(CH3)—CH(CH3)2 | H | 2-chloro-6-fluorophenyl | Cl | CONHSO2CH3 | 3.9* |
| 172 | CH(CH3)—CH(CH3)2 | H | 2-chloro-6-fluorophenyl | Cl | CONHSO2CH2CH3 | |
| 173 | CH(CH3)—CH(CH3)2 | H | 2-chloro-6-fluorophenyl | Cl | (isoxazol-3-ylamino)carbonyl | |
| 174 | CH(CH3)—CH(CH3)2 | H | 2-chloro-6-fluorophenyl | Cl | [(4-methyl-4H-1,2,4-triazol-3-yl)amino]carbonyl | |
| 175 | CH(CH3)—CH(CH3)2 | H | 2,4,6-trifluorophenyl | Cl | CONHCONHCH3 | |
| 176 | CH(CH3)—CH(CH3)2 | H | 2,4,6-trifluorophenyl | Cl | CONHSO2CF3 | |
| 177 | (R) CH(CH3)—CH(CH3)2 | H | 2,4,6-trifluorophenyl | Cl | CONHSO2CH3 | 3.85* |
| 178 | CH(CH3)—CH(CH3)2 | H | 2,4,6-trifluorophenyl | Cl | CONHSO2CH2CH3 | |
| 179 | CH(CH3)—CH(CH3)2 | H | 2,4,6-trifluorophenyl | Cl | (isoxazol-3-ylamino)carbonyl | |
| 180 | CH(CH3)—CH(CH3)2 | H | 2,4,6-trifluorophenyl | Cl | [(4-methyl-4H-1,2,4-triazol-3-yl)amino]carbonyl | |
| 181 | CH(CH3)—CH(CH3)2 | H | 2-chloro-4-fluorophenyl | Cl | CONHCONHCH3 | |
| 182 | CH(CH3)—CH(CH3)2 | H | 2-chloro-4-fluorophenyl | Cl | CONHSO2CF3 | |
| 183 | (R) CH(CH3)—CH(CH3)2 | H | 2-chloro-4-fluorophenyl | Cl | CONHSO2CH3 | 4.18 |
| 184 | CH(CH3)—CH(CH3)2 | H | 2-chloro-4-fluorophenyl | Cl | CONHSO2CH2CH3 | |
| 185 | CH(CH3)—CH(CH3)2 | H | 2-chloro-4-fluorophenyl | Cl | (isoxazol-3-ylamino)carbonyl | |
| 186 | CH(CH3)—CH(CH3)2 | H | 2-chloro-4-fluorophenyl | Cl | [(4-methyl-4H-1,2,4-triazol-3-yl)amino]carbonyl | |
| 187 | CH(CH3)—CH(CH3)2 | H | 2-chlorophenyl | Cl | CONHCONHCH3 | |
| 188 | CH(CH3)—CH(CH3)2 | H | 2-chlorophenyl | Cl | CONHSO2CF3 | |
| 189 | (R) CH(CH3)—CH(CH3)2 | H | 2-chlorophenyl | Cl | CONHSO2CH3 | 4.01* |
| 190 | CH(CH3)—CH(CH3)2 | H | 2-chlorophenyl | Cl | CONHSO2CH2CH3 | |
| 191 | CH(CH3)—CH(CH3)2 | H | 2-chlorophenyl | Cl | (isoxazol-3-ylamino)carbonyl | |
| 192 | CH(CH3)—CH(CH3)2 | H | 2-chlorophenyl | Cl | [(4-methyl-4H-1,2,4-triazol-3-yl)amino]carbonyl | |
| 193 | CH(CH3)—CH(CH3)2 | H | 5-Cl-pyrimidin-4-yl | Cl | CONHCONHCH3 | |
| 194 | CH(CH3)—CH(CH3)2 | H | 5-Cl-pyrimidin-4-yl | Cl | CONHSO2CF3 | |
| 195 | CH(CH3)—CH(CH3)2 | H | 5-Cl-pyrimidin-4-yl | Cl | CONHSO2CH3 | |
| 196 | CH(CH3)—CH(CH3)2 | H | 5-Cl-pyrimidin-4-yl | Cl | CONHSO2CH2CH3 | |
| 197 | CH(CH3)—CH(CH3)2 | H | 5-Cl-pyrimidin-4-yl | Cl | (isoxazol-3-ylamino)carbonyl | |

TABLE 1-continued

Structure: pyrazolo[1,5-a]pyrimidine with NR¹R² at position 7, R³ at position 6, X at position 5, R⁴ at position 3.

| Ex. No. | R¹ or —R¹⁺R²— | R² | R3 | X | R4 | log p |
|---|---|---|---|---|---|---|
| 198 | CH(CH₃)—CH(CH₃)₂ | H | 5-Cl-pyrimidin-4-yl | Cl | [(4-methyl-4H-1,2,4-triazol-3-yl)amino]carbonyl | |
| 199 | CH(CH₃)—CH(CH₃)₂ | H | 2-chloro-4,6-difluorophenyl | Cl | CONHCONHCH₃ | |
| 200 | CH(CH₃)—CH(CH₃)₂ | H | 2-chloro-4,6-difluorophenyl | Cl | CONHSO₂CF₃ | |
| 201 | (R) CH(CH₃)—CH(CH₃)₂ | H | 2-chloro-4,6-difluorophenyl | Cl | CONHSO₂CH₃ | 4.05* |
| 202 | CH(CH₃)—CH(CH₃)₂ | H | 2-chloro-4,6-difluorophenyl | Cl | CONHSO₂CH₂CH₃ | |
| 203 | CH(CH₃)—CH(CH₃)₂ | H | 2-chloro-4,6-difluorophenyl | Cl | (isoxazol-3-ylamino)carbonyl | |
| 204 | CH(CH₃)—CH(CH₃)₂ | H | 2-chloro-4,6-difluorophenyl | Cl | [(4-methyl-4H-1,2,4-triazol-3-yl)amino]carbonyl | |
| 205 | CH(CH₃)—CH(CH₃)₂ | H | 2,4-dichlorophenyl | Cl | CONHCONHCH₃ | |
| 206 | (R) CH(CH₃)—CH(CH₃)₂ | H | 2,4-dichlorophenyl | Cl | CONHSO₂CF₃ | 3.87** |
| 207 | (R) CH(CH₃)—CH(CH₃)₂ | H | 2,4-dichlorophenyl | Cl | CONHSO₂CH₃ | 4.55* |
| 208 | (R) CH(CH₃)—CH(CH₃)₂ | H | 2,4-dichlorophenyl | Cl | CONHSO₂CH₂CH₃ | 4.88** |
| 209 | CH(CH₃)—CH(CH₃)₂ | H | 2,4-dichlorophenyl | Cl | (isoxazol-3-ylamino)carbonyl | |
| 210 | CH(CH₃)—CH(CH₃)₂ | H | 2,4-dichlorophenyl | Cl | [(4-methyl-4H-1,2,4-triazol-3-yl)amino]carbonyl | |
| 211 | CH(CH₃)—CH(CH₃)₂ | H | 4-chloro-2,6-difluorophenyl | Cl | CONHCONHCH₃ | |
| 212 | CH(CH₃)—CH(CH₃)₂ | H | 4-chloro-2,6-difluorophenyl | Cl | CONHSO₂CF₃ | |
| 213 | (R) CH(CH₃)—CH(CH₃)₂ | H | 4-chloro-2,6-difluorophenyl | Cl | CONHSO₂CH₃ | 4.24* |
| 214 | CH(CH₃)—CH(CH₃)₂ | H | 4-chloro-2,6-difluorophenyl | Cl | CONHSO₂CH₂CH₃ | |
| 215 | CH(CH₃)—CH(CH₃)₂ | H | 4-chloro-2,6-difluorophenyl | Cl | (isoxazol-3-ylamino)carbonyl | |
| 216 | CH(CH₃)—CH(CH₃)₂ | H | 4-chloro-2,6-difluorophenyl | Cl | [(4-methyl-4H-1,2,4-triazol-3-yl)amino]carbonyl | |
| 217 | CH(CH₃)—CH(CH₃)₂ | H | 2,6-difluoro-4-methylphenyl | Cl | CONHCONHCH₃ | |
| 218 | CH(CH₃)—CH(CH₃)₂ | H | 2,6-difluoro-4-methylphenyl | Cl | CONHSO₂CF₃ | |
| 219 | (R) CH(CH₃)—CH(CH₃)₂ | H | 2,6-difluoro-4-methylphenyl | Cl | CONHSO₂CH₃ | 4.08** |
| 220 | CH(CH₃)—CH(CH₃)₂ | H | 2,6-difluoro-4-methylphenyl | Cl | CONHSO₂CH₂CH₃ | |
| 221 | CH(CH₃)—CH(CH₃)₂ | H | 2,6-difluoro-4-methylphenyl | Cl | (isoxazol-3-ylamino)carbonyl | |
| 222 | CH(CH₃)—CH(CH₃)₂ | H | 2,6-difluoro-4-methylphenyl | Cl | [(4-methyl-4H-1,2,4-triazol-3-yl)amino]carbonyl | |
| 223 | CH(CH₃)—CH(CH₃)₂ | H | 2-chloro-5-fluorophenyl | Cl | CONHCONHCH₃ | |
| 224 | CH(CH₃)—CH(CH₃)₂ | H | 2-chloro-5-fluorophenyl | Cl | CONHSO₂CF₃ | |
| 225 | CH(CH₃)—CH(CH₃)₂ | H | 2-chloro-5-fluorophenyl | Cl | CONHSO₂CH₃ | |
| 226 | CH(CH₃)—CH(CH₃)₂ | H | 2-chloro-5-fluorophenyl | Cl | CONHSO₂CH₂CH₃ | |
| 227 | CH(CH₃)—CH(CH₃)₂ | H | 2-chloro-5-fluorophenyl | Cl | (isoxazol-3-ylamino)carbonyl | |
| 228 | CH(CH₃)—CH(CH₃)₂ | H | 2-chloro-5-fluorophenyl | Cl | [(4-methyl-4H-1,2,4-triazol-3-yl)amino]carbonyl | |
| 229 | CH(CH₃)—CH(CH₃)₂ | H | 3-chloro-2-thienyl | Cl | CONHCONHCH₃ | |
| 230 | CH(CH₃)—CH(CH₃)₂ | H | 3-chloro-2-thienyl | Cl | CONHSO₂CF₃ | |
| 231 | CH(CH₃)—CH(CH₃)₂ | H | 3-chloro-2-thienyl | Cl | CONHSO₂CH₃ | |
| 232 | CH(CH₃)—CH(CH₃)₂ | H | 3-chloro-2-thienyl | Cl | CONHSO₂CH₂CH₃ | |
| 233 | CH(CH₃)—CH(CH₃)₂ | H | 3-chloro-2-thienyl | Cl | (isoxazol-3-ylamino)carbonyl | |
| 234 | CH(CH₃)—CH(CH₃)₂ | H | 3-chloro-2-thienyl | Cl | [(4-methyl-4H-1,2,4-triazol-3-yl)amino]carbonyl | |
| 235 | CH(CH₃)—CH(CH₃)₂ | H | phenyl | Cl | CONHCONHCH₃ | |
| 236 | CH(CH₃)—CH(CH₃)₂ | H | phenyl | Cl | CONHSO₂CF₃ | |
| 237 | CH(CH₃)—CH(CH₃)₂ | H | phenyl | Cl | CONHSO₂CH₃ | |
| 238 | CH(CH₃)—CH(CH₃)₂ | H | phenyl | Cl | CONHSO₂CH₂CH₃ | |
| 239 | CH(CH₃)—CH(CH₃)₂ | H | phenyl | Cl | (isoxazol-3-ylamino)carbonyl | |

TABLE 1-continued

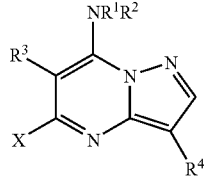

| Ex. No. | R¹ or —R¹⁺R²— | R² | R3 | X | R4 | log p |
|---|---|---|---|---|---|---|
| 240 | CH(CH₃)—CH(CH₃)₂ | H | phenyl | Cl | [(4-methyl-4H-1,2,4-triazol-3-yl)amino]carbonyl | |
| 241 | CH(CH₃)—CH(CH₃)₂ | H | cyclopentyl | Cl | CONHCONHCH₃ | |
| 242 | CH(CH₃)—CH(CH₃)₂ | H | cyclopentyl | Cl | CONHSO₂CF₃ | |
| 243 | CH(CH₃)—CH(CH₃)₂ | H | cyclopentyl | Cl | CONHSO₂CH₃ | |
| 244 | CH(CH₃)—CH(CH₃)₂ | H | cyclopentyl | Cf | CONHSO₂CH₂CH₃ | |
| 245 | CH(CH₃)—CH(CH₃)₂ | H | cyclopentyl | Cl | (isoxazol-3-ylamino)carbonyl | |
| 246 | CH(CH₃)—CH(CH₃)₂ | H | cyclopentyl | Cl | [(4-methyl-4H-1,2,4-triazol-3-yl)amino]carbonyl | |
| 247 | CH(CH₃)—CH(CH₃)₂ | H | sec-butyl | Cl | CONHCONHCH₃ | |
| 248 | CH(CH₃)—CH(CH₃)₂ | H | sec-butyl | Cl | CONHSO₂CF₃ | |
| 249 | CH(CH₃)—CH(CH₃)₂ | H | sec-butyl | Cl | CONHSO₂CH₃ | |
| 250 | CH(CH₃)—CH(CH₃)₂ | H | sec-butyl | Cl | CONHSO₂CH₂CH₃ | |
| 251 | CH(CH₃)—CH(CH₃)₂ | H | sec-butyl | Cl | (isoxazol-3-ylamino)carbonyl | |
| 252 | CH(CH₃)—CH(CH₃)₂ | H | sec-butyl | Cl | [(4-methyl-4H-1,2,4-triazol-3-yl)amino]carbonyl | |
| 253 | —CH₂—CH₂—CH(CH₃)—CH₂—CH₂— | | 2-chloro-6-fluorophenyl | Cl | CONHCONHCH₃ | |
| 254 | —CH₂—CH₂—CH(CH₃)—CH₂—CH₂— | | 2-chloro-6-fluorophenyl | Cl | CONHSO₂CF₃ | |
| 255 | —CH₂—CH₂—CH(CH₃)—CH₂—CH₂— | | 2-chloro-6-fluorophenyl | Cl | CONHSO₂CH₃ | 4.2* |
| 256 | —CH₂—CH₂—CH(CH₃)—CH₂—CH₂— | | 2-chloro-6-fluorophenyl | Cl | CONHSO₂CH₂CH₃ | |
| 257 | —CH₂—CH₂—CH(CH₃)—CH₂—CH₂— | | 2-chloro-6-fluorophenyl | Cl | (isoxazol-3-ylamino)carbonyl | |
| 258 | —CH₂—CH₂—CH(CH₃)—CH₂—CH₂— | | 2-chloro-6-fluorophenyl | Cl | [(4-methyl-4H-1,2,4-triazol-3-yl)amino]carbonyl | |
| 259 | —CH₂—CH₂—CH(CH₃)—CH₂—CH₂— | | 2,4,6-trifluorophenyl | Cl | CONHCONHCH₃ | |
| 260 | —CH₂—CH₂—CH(CH₃)—CH₂—CH₂— | | 2,4,6-trifluorophenyl | Cl | CONHSO₂CF₃ | |
| 261 | —CH₂—CH₂—CH(CH₃)—CH₂—CH₂— | | 2,4,6-trifluorophenyl | Cl | CONHSO₂CH₃ | 4.07* |
| 262 | —CH₂—CH₂—CH(CH₃)—CH₂—CH₂— | | 2,4,6-trifluorophenyl | Cl | CONHSO₂CH₂CH₃ | |
| 263 | —CH₂—CH₂—CH(CH₃)—CH₂—CH₂— | | 2,4,6-trifluorophenyl | Cl | (isoxazol-3-ylamino)carbonyl | |
| 264 | —CH₂—CH₂—CH(CH₃)—CH₂—CH₂— | | 2,4,6-trifluorophenyl | Cl | [(4-methyl-4H-1,2,4-triazol-3-yl)amino]carbonyl | |
| 265 | —CH₂—CH₂—CH(CH₃)—CH₂—CH₂— | | 2-chloro-4-fluorophenyl | Cl | CONHCONHCH₃ | |
| 266 | —CH₂—CH₂—CH(CH₃)—CH₂—CH₂— | | 2-chloro-4-fluorophenyl | Cl | CONHSO₂CF₃ | |
| 267 | —CH₂—CH₂—CH(CH₃)—CH₂—CH₂— | | 2-chloro-4-fluorophenyl | Cl | CONHSO₂CH₃ | |
| 268 | —CH₂—CH₂—CH(CH₃)—CH₂—CH₂— | | 2-chloro-4-fluorophenyl | Cl | CONHSO₂CH₂CH₃ | |
| 269 | —CH₂—CH₂—CH(CH₃)—CH₂—CH₂— | | 2-chloro-4-fluorophenyl | Cl | (isoxazol-3-ylamino)carbonyl | |
| 270 | —CH₂—CH₂—CH(CH₃)—CH₂—CH₂— | | 2-chloro-4-fluorophenyl | Cl | [(4-methyl-4H-1,2,4-triazol-3-yl)amino]carbonyl | |
| 271 | —CH₂—CH₂—CH(CH₃)—CH₂—CH₂— | | 2-chlorophenyl | Cl | CONHCONHCH₃ | |
| 272 | —CH₂—CH₂—CH(CH₃)—CH₂—CH₂— | | 2-chlorophenyl | Cl | CONHSO₂CF₃ | |
| 273 | —CH₂—CH₂—CH(CH₃)—CH₂—CH₂— | | 2-chlorophenyl | Cl | CONHSO₂CH₃ | |
| 274 | —CH₂—CH₂—CH(CH₃)—CH₂—CH₂— | | 2-chlorophenyl | Cl | CONHSO₂CH₂CH₃ | |
| 275 | —CH₂—CH₂—CH(CH₃)—CH₂—CH₂— | | 2-chlorophenyl | Cl | (isoxazol-3-ylamino)carbonyl | |
| 276 | —CH₂—CH₂—CH(CH₃)—CH₂—CH₂— | | 2-chlorophenyl | Cl | [(4-methyl-4H-1,2,4-triazol-3-yl)amino]carbonyl | |
| 277 | —CH₂—CH₂—CH(CH₃)—CH₂—CH₂— | | 5-Cl-pyrimidin-4-yl | Cl | CONHCONHCH₃ | |
| 278 | —CH₂—CH₂—CH(CH₃)—CH₂—CH₂— | | 5-Cl-pyrimidin-4-yl | Cl | CONHSO₂CF₃ | |
| 279 | —CH₂—CH₂—CH(CH₃)—CH₂—CH₂— | | 5-Cl-pyrimidin-4-yl | Cl | CONHSO₂CH₃ | |
| 280 | —CH₂—CH₂—CH(CH₃)—CH₂—CH₂— | | 5-Cl-pyrimidin-4-yl | Cl | CONHSO₂CH₂CH₃ | |
| 281 | —CH₂—CH₂—CH(CH₃)—CH₂—CH₂— | | 5-Cl-pyrimidin-4-yl | Cl | (isoxazol-3-ylamino)carbonyl | |
| 282 | —CH₂—CH₂—CH(CH₃)—CH₂—CH₂— | | 5-Cl-pyrimidin-4-yl | Cl | [(4-methyl-4H-1,2,4-triazol-3-yl)amino]carbonyl | |
| 283 | —CH₂—CH₂—CH(CH₃)—CH₂—CH₂— | | 2-chloro-4,6-difluorophenyl | Cl | CONHCONHCH₃ | |
| 284 | —CH₂—CH₂—CH(CH₃)—CH₂—CH₂— | | 2-chloro-4,6-difluorophenyl | Cl | CONHSO₂CF₃ | |
| 285 | —CH₂—CH₂—CH(CH₃)—CH₂—CH₂— | | 2-chloro-4,6-difluorophenyl | Cl | CONHSO₂CH₃ | 4.34* |
| 286 | —CH₂—CH₂—CH(CH₃)—CH₂—CH₂— | | 2-chloro-4,6-difluorophenyl | Cl | CONHSO₂CH₂CH₃ | |
| 287 | —CH₂—CH₂—CH(CH₃)—CH₂—CH₂— | | 2-chloro-4,6-difluorophenyl | Cl | (isoxazol-3-ylamino)carbonyl | |
| 288 | —CH₂—CH₂—CH(CH₃)—CH₂—CH₂— | | 2-chloro-4,6-difluorophenyl | Cl | [(4-methyl-4H-1,2,4-triazol-3-yl)amino]carbonyl | |
| 289 | —CH₂—CH₂—CH(CH₃)—CH₂—CH₂— | | 2,4-dichlorophenyl | Cl | CONHCONHCH₃ | |
| 290 | —CH₂—CH₂—CH(CH₃)—CH₂—CH₂— | | 2,4-dichlorophenyl | Cl | CONHSO₂CF₃ | |

TABLE 1-continued

| Ex. No. | R¹ or —R¹⁺R²— | R² | R3 | X | R4 | log p |
|---|---|---|---|---|---|---|
| 291 | —CH₂—CH₂—CH(CH₃)—CH₂—CH₂— | | 2,4-dichlorophenyl | Cl | CONHSO₂CH₃ | |
| 292 | —CH₂—CH₂—CH(CH₃)—CH₂—CH₂— | | 2,4-dichlorophenyl | Cl | CONHSO₂CH₂CH₃ | |
| 293 | —CH₂—CH₂—CH(CH₃)—CH₂—CH₂— | | 2,4-dichlorophenyl | Cl | (isoxazol-3-ylamino)carbonyl | |
| 294 | —CH₂—CH₂—CH(CH₃)—CH₂—CH₂— | | 2,4-dichlorophenyl | Cl | [(4-methyl-4H-1,2,4-triazol-3-yl)amino]carbonyl | |
| 295 | —CH₂—CH₂—CH(CH₃)—CH₂—CH₂— | | 4-chloro-2,6-difluorophenyl | Cl | CONHCONHCH₃ | |
| 296 | —CH₂—CH₂—CH(CH₃)—CH₂—CH₂— | | 4-chloro-2,6-difluorophenyl | Cl | CONHSO₂CF₃ | |
| 297 | —CH₂—CH₂—CH(CH₃)—CH₂—CH₂— | | 4-chloro-2,6-difluorophenyl | Cl | CONHSO₂CH₃ | |
| 298 | —CH₂—CH₂—CH(CH₃)—CH₂—CH₂— | | 4-chloro-2,6-difluorophenyl | Cl | CONHSO₂CH₂CH₃ | |
| 299 | —CH₂—CH₂—CH(CH₃)—CH₂—CH₂— | | 4-chloro-2,6-difluorophenyl | Cl | (isoxazol-3-ylamino)carbonyl | |
| 300 | —CH₂—CH₂—CH(CH₃)—CH₂—CH₂— | | 4-chloro-2,6-difluorophenyl | Cl | [(4-methyl-4H-1,2,4-triazol-3-yl)amino]carbonyl | |
| 301 | —CH₂—CH₂—CH(CH₃)—CH₂—CH₂— | | 2,6-difluoro-4-methylphenyl | Cl | CONHCONHCH₃ | |
| 302 | —CH₂—CH₂—CH(CH₃)—CH₂—CH₂— | | 2,6-difluoro-4-methylphenyl | Cl | CONHSO₂CF₃ | |
| 303 | —CH₂—CH₂—CH(CH₃)—CH₂—CH₂— | | 2,6-difluoro-4-methylphenyl | Cl | CONHSO₂CH₃ | |
| 304 | —CH₂—CH₂—CH(CH₃)—CH₂—CH₂— | | 2,6-difluoro-4-methylphenyl | Cl | CONHSO₂CH₂CH₃ | |
| 305 | —CH₂—CH₂—CH(CH₃)—CH₂—CH₂— | | 2,6-difluoro-4-methylphenyl | Cl | (isoxazol-3-ylamino)carbonyl | |
| 306 | —CH₂—CH₂—CH(CH₃)—CH₂—CH₂— | | 2,6-difluoro-4-methylphenyl | Cl | [(4-methyl-4H-1,2,4-triazol-3-yl)amino]carbonyl | |
| 307 | —CH₂—CH₂—CH(CH₃)—CH₂—CH₂— | | 2-chloro-5-fluorophenyl | Cl | CONHCONHCH₃ | |
| 308 | —CH₂—CH₂—CH(CH₃)—CH₂—CH₂— | | 2-chloro-5-fluorophenyl | Cl | CONHSO₂CF₃ | |
| 309 | —CH₂—CH₂—CH(CH₃)—CH₂—CH₂— | | 2-chloro-5-fluorophenyl | Cl | CONHSO₂CH₃ | |
| 310 | —CH₂—CH₂—CH(CH₃)—CH₂—CH₂— | | 2-chloro-5-fluorophenyl | Cl | CONHSO₂CH₂CH₃ | |
| 311 | —CH₂—CH₂—CH(CH₃)—CH₂—CH₂— | | 2-chloro-5-fluorophenyl | Cl | (isoxazol-3-ylamino)carbonyl | |
| 312 | —CH₂—CH₂—CH(CH₃)—CH₂—CH₂— | | 2-chloro-5-fluorophenyl | Cl | [(4-methyl-4H-1,2,4-triazol-3-yl)amino]carbonyl | |
| 313 | —CH₂—CH₂—CH(CH₃)—CH₂—CH₂— | | 3-chloro-2-thienyl | Cl | CONHCONHCH₃ | |
| 314 | —CH₂—CH₂—CH(CH₃)—CH₂—CH₂— | | 3-chloro-2-thienyl | Cl | CONHSO₂CF₃ | |
| 315 | —CH₂—CH₂—CH(CH₃)—CH₂—CH₂— | | 3-chloro-2-thienyl | Cl | CONHSO₂CH₃ | |
| 316 | —CH₂—CH₂—CH(CH₃)—CH₂—CH₂— | | 3-chloro-2-thienyl | Cl | CONHSO₂CH₂CH₃ | |
| 317 | —CH₂—CH₂—CH(CH₃)—CH₂—CH₂— | | 3-chloro-2-thienyl | Cl | (isoxazol-3-ylamino)carbonyl | |
| 318 | —CH₂—CH₂—CH(CH₃)—CH₂—CH₂— | | 3-chloro-2-thienyl | Cl | [(4-methyl-4H-1,2,4-triazol-3-yl)amino]carbonyl | |
| 319 | —CH₂—CH₂—CH(CH₃)—CH₂—CH₂— | | phenyl | Cl | CONHCONHCH₃ | |
| 320 | —CH₂—CH₂—CH(CH₃)—CH₂—CH₂— | | phenyl | Cl | CONHSO₂CF₃ | |
| 321 | —CH₂—CH₂—CH(CH₃)—CH₂—CH₂— | | phenyl | Cl | CONHSO₂CH₃ | |
| 322 | —CH₂—CH₂—CH(CH₃)—CH₂—CH₂— | | phenyl | Cl | CONHSO₂CH₂CH₃ | |
| 323 | —CH₂—CH₂—CH(CH₃)—CH₂—CH₂— | | phenyl | Cl | (isoxazol-3-ylamino)carbonyl | |
| 324 | —CH₂—CH₂—CH(CH₃)—CH₂—CH₂— | | phenyl | Cl | [(4-methyl-4H-1,2,4-triazol-3-yl)amino]carbonyl | |
| 325 | —CH₂—CH₂—CH(CH₃)—CH₂—CH₂— | | cyclopentyl | Cl | CONHCONHCH₃ | |
| 326 | —CH₂—CH₂—CH(CH₃)—CH₂—CH₂— | | cyclopentyl | Cl | CONHSO₂CF₃ | |
| 327 | —CH₂—CH₂—CH(CH₃)—CH₂—CH₂— | | cyclopentyl | Cl | CONHSO₂CH₃ | |
| 328 | —CH₂—CH₂—CH(CH₃)—CH₂—CH₂— | | cyclopentyl | Cl | CONHSO₂CH₂CH₃ | |
| 329 | —CH₂—CH₂—CH(CH₃)—CH₂—CH₂— | | cyclopentyl | Cl | (isoxazol-3-ylamino)carbonyl | |
| 330 | —CH₂—CH₂—CH(CH₃)—CH₂—CH₂— | | cyclopentyl | Cl | [(4-methyl-4H-1,2,4-triazol-3-yl)amino]carbonyl | |
| 331 | —CH₂—CH₂—CH(CH₃)—CH₂—CH₂— | | sec-butyl | Cl | CONHCONHCH₃ | |
| 332 | —CH₂—CH₂—CH(CH₃)—CH₂—CH₂— | | sec-butyl | Cl | CONHSO₂CF₃ | |
| 333 | —CH₂—CH₂—CH(CH₃)—CH₂—CH₂— | | sec-butyl | Cl | CONHSO₂CH₃ | |
| 334 | —CH₂—CH₂—CH(CH₃)—CH₂—CH₂— | | sec-butyl | Cl | CONHSO₂CH₂CH₃ | |
| 335 | —CH₂—CH₂—CH(CH₃)—CH₂—CH₂— | | sec-butyl | Cl | (isoxazol-3-ylamino)carbonyl | |
| 336 | —CH₂—CH₂—CH(CH₃)—CH₂—CH₂— | | sec-butyl | Cl | [(4-methyl-4H-1,2,4-triazol-3-yl)amino]carbonyl | |
| 337 | i-propyl | H | 2-chloro-6-fluorophenyl | Cl | CONHCONHCH₃ | |

TABLE 1-continued structure: 7-(NR¹R²)-6-R³-5-X-3-R⁴-pyrazolo[1,5-a]pyrimidine

| Ex. No. | R¹ | R² or —R¹+R²— | R3 | X | R4 | log p |
|---|---|---|---|---|---|---|
| 338 | i-propyl | H | 2-chloro-6-fluorophenyl | Cl | $CONHSO_2CF_3$ | |
| 339 | i-propyl | H | 2-chloro-6-fluorophenyl | Cl | $CONHSO_2CH_3$ | |
| 340 | i-propyl | H | 2-chloro-6-fluorophenyl | Cl | $CONHSO_2CH_2CH_3$ | |
| 341 | i-propyl | H | 2-chloro-6-fluorophenyl | Cl | (isoxazol-3-ylamino)carbonyl | |
| 342 | i-propyl | H | 2-chloro-6-fluorophenyl | Cl | [(4-methyl-4H-1,2,4-triazol-3-yl)amino]carbonyl | |
| 343 | i-propyl | H | 2,4,6-trifluorophenyl | Cl | $CONHCONHCH_3$ | |
| 344 | i-propyl | H | 2,4,6-trifluorophenyl | Cl | $CONHSO_2CF_3$ | |
| 345 | i-propyl | H | 2,4,6-trifluorophenyl | Cl | $CONHSO_2CH_3$ | 3.24* |
| 346 | i-propyl | H | 2,4,6-trifluorophenyl | Cl | $CONHSO_2CH_2CH_3$ | |
| 347 | i-propyl | H | 2,4,6-trifluorophenyl | Cl | (isoxazol-3-ylamino)carbonyl | |
| 348 | i-propyl | H | 2,4,6-trifluorophenyl | Cl | [(4-methyl-4H-1,2,4-triazol-3-yl)amino]carbonyl | |
| 349 | i-propyl | H | 2-chloro-4-fluorophenyl | Cl | $CONHCONHCH_3$ | |
| 350 | i-propyl | H | 2-chloro-4-fluorophenyl | Cl | $CONHSO_2CF_3$ | |
| 351 | i-propyl | H | 2-chloro-4-fluorophenyl | Cl | $CONHSO_2CH_3$ | 3.57* |
| 352 | i-propyl | H | 2-chloro-4-fluorophenyl | Cl | $CONHSO_2CH_2CH_3$ | |
| 353 | i-propyl | H | 2-chloro-4-fluorophenyl | Cl | (isoxazol-3-ylamino)carbonyl | |
| 354 | i-propyl | H | 2-chloro-4-fluorophenyl | Cl | [(4-methyl-4H-1,2,4-triazol-3-yl)amino]carbonyl | |
| 355 | i-propyl | H | 2-chlorophenyl | Cl | $CONHCONHCH_3$ | |
| 356 | i-propyl | H | 2-chlorophenyl | Cl | $CONHSO_2CF_3$ | |
| 357 | i-propyl | H | 2-chlorophenyl | Cl | $CONHSO_2CH_3$ | 3.44* |
| 358 | i-propyl | H | 2-chlorophenyl | Cl | $CONHSO_2CH_2CH_3$ | |
| 359 | i-propyl | H | 2-chlorophenyl | Cl | (isoxazol-3-ylamino)carbonyl | |
| 360 | i-propyl | H | 2-chlorophenyl | Cl | [(4-methyl-4H-1,2,4-triazol-3-yl)amino]carbonyl | |
| 361 | i-propyl | H | 5-Cl-pyrimidin-4-yl | Cl | $CONHCONHCH_3$ | |
| 362 | i-propyl | H | 5-Cl-pyrimidin-4-yl | Cl | $CONHSO_2CF_3$ | |
| 363 | i-propyl | H | 5-Cl-pyrimidin-4-yl | Cl | $CONHSO_2CH_3$ | |
| 364 | i-propyl | H | 5-Cl-pyrimidin-4-yl | Cl | $CONHSO_2CH_2CH_3$ | |
| 365 | i-propyl | H | 5-Cl-pyrimidin-4-yl | Cl | (isoxazol-3-ylamino)carbonyl | |
| 366 | i-propyl | H | 5-Cl-pyrimidin-4-yl | Cl | [(4-methyl-4H-1,2,4-triazol-3-yl)amino]carbonyl | |
| 367 | i-propyl | H | 2-chloro-4,6-difluorophenyl | Cl | $CONHCONHCH_3$ | |
| 368 | i-propyl | H | 2-chloro-4,6-difluorophenyl | Cl | $CONHSO_2CF_3$ | |
| 369 | i-propyl | H | 2-chloro-4,6-difluorophenyl | Cl | $CONHSO_2CH_3$ | |
| 370 | i-propyl | H | 2-chloro-4,6-difluorophenyl | Cl | $CONHSO_2CH_2CH_3$ | |
| 371 | i-propyl | H | 2-chloro-4,6-difluorophenyl | Cl | (isoxazol-3-ylamino)carbonyl | |
| 372 | i-propyl | H | 2-chloro-4,6-difluorophenyl | Cl | [(4-methyl-4H-1,2,4-triazol-3-yl)amino]carbonyl | |
| 373 | i-propyl | H | 2,4-dichlorophenyl | Cl | $CONHCONHCH_3$ | |
| 374 | i-propyl | H | 2,4-dichlorophenyl | Cl | $CONHSO_2CF_3$ | |
| 375 | i-propyl | H | 2,4-dichlorophenyl | Cl | $CONHSO_2CH_3$ | 3.91* |
| 376 | i-propyl | H | 2,4-dichlorophenyl | Cl | $CONHSO_2CH_2CH_3$ | |
| 377 | i-propyl | H | 2,4-dichlorophenyl | Cl | (isoxazol-3-ylamino)carbonyl | |
| 378 | i-propyl | H | 2,4-dichlorophenyl | Cl | [(4-methyl-4H-1,2,4-triazol-3-yl)amino]carbonyl | |
| 379 | i-propyl | H | 4-chloro-2,6-difluorophenyl | Cl | $CONHCONHCH_3$ | |
| 380 | i-propyl | H | 4-chloro-2,6-difluorophenyl | Cl | $CONHSO_2CF_3$ | |
| 381 | i-propyl | H | 4-chloro-2,6-difluorophenyl | Cl | $CONHSO_2CH_3$ | 3.68* |
| 382 | i-propyl | H | 4-chloro-2,6-difluorophenyl | Cl | $CONHSO_2CH_2CH_3$ | |
| 383 | i-propyl | H | 4-chloro-2,6-difluorophenyl | Cl | (isoxazol-3-ylamino)carbonyl | |
| 384 | i-propyl | H | 4-chloro-2,6-difluorophenyl | Cl | [(4-methyl-4H-1,2,4-triazol-3-yl)amino]carbonyl | |

TABLE 1-continued

Structure: pyrazolo[1,5-a]pyrimidine with substituents NR¹R² (position 7), R³ (position 6), X (position 5), R⁴ (position 3)

| Ex. No. | R¹ or —R¹⁺R²— | R² | R3 | X | R4 | log p |
|---|---|---|---|---|---|---|
| 385 | i-propyl | H | 2,6-difluoro-4-methylphenyl | Cl | CONHCONHCH$_3$ | |
| 386 | i-propyl | H | 2,6-difluoro-4-methylphenyl | Cl | CONHSO$_2$CF$_3$ | |
| 387 | i-propyl | H | 2,6-difluoro-4-methylphenyl | Cl | CONHSO$_2$CH$_3$ | |
| 388 | i-propyl | H | 2,6-difluoro-4-methylphenyl | Cl | CONHSO$_2$CH$_2$CH$_3$ | |
| 389 | i-propyl | H | 2,6-difluoro-4-methylphenyl | Cl | (isoxazol-3-ylamino)carbonyl | |
| 390 | i-propyl | H | 2,6-difluoro-4-methylphenyl | Cl | [(4-methyl-4H-1,2,4-triazol-3-yl)amino]carbonyl | |
| 391 | i-propyl | H | 2-chloro-5-fluorophenyl | Cl | CONHCONHCH$_3$ | |
| 392 | i-propyl | H | 2-chloro-5-fluorophenyl | Cl | CONHSO$_2$CF$_3$ | |
| 393 | i-propyl | H | 2-chloro-5-fluorophenyl | Cl | CONHSO$_2$CH$_3$ | |
| 394 | i-propyl | H | 2-chloro-5-fluorophenyl | Cl | CONHSO$_2$CH$_2$CH$_3$ | |
| 395 | i-propyl | H | 2-chloro-5-fluorophenyl | Cl | (isoxazol-3-ylamino)carbonyl | |
| 396 | i-propyl | H | 2-chloro-5-fluorophenyl | Cl | [(4-methyl-4H-1,2,4-triazol-3-yl)amino]carbonyl | |
| 397 | i-propyl | H | 3-chloro-2-thienyl | Cl | CONHCONHCH$_3$ | |
| 398 | i-propyl | H | 3-chloro-2-thienyl | Cl | CONHSO$_2$CF$_3$ | |
| 399 | i-propyl | H | 3-chloro-2-thienyl | Cl | CONHSO$_2$CH$_3$ | |
| 400 | i-propyl | H | 3-chloro-2-thienyl | Cl | CONHSO$_2$CH$_2$CH$_3$ | |
| 401 | i-propyl | H | 3-chloro-2-thienyl | Cl | (isoxazol-3-ylamino)carbonyl | |
| 402 | i-propyl | H | 3-chloro-2-thienyl | Cl | [(4-methyl-4H-1,2,4-triazol-3-yl)amino]carbonyl | |
| 403 | i-propyl | H | phenyl | Cl | CONHCONHCH$_3$ | |
| 404 | i-propyl | H | phenyl | Cl | CONHSO$_2$CF$_3$ | |
| 405 | i-propyl | H | phenyl | Cl | CONHSO$_2$CH$_3$ | |
| 406 | i-propyl | H | phenyl | Cl | CONHSO$_2$CH$_2$CH$_3$ | |
| 407 | i-propyl | H | phenyl | Cl | (isoxazol-3-ylamino)carbonyl | |
| 408 | i-propyl | H | phenyl | Cl | [(4-methyl-4H-1,2,4-triazol-3-yl)amino]carbonyl | |
| 409 | i-propyl | H | cyclopentyl | Cl | CONHCONHCH$_3$ | |
| 410 | i-propyl | H | cyclopentyl | Cl | CONHSO$_2$CF$_3$ | |
| 411 | i-propyl | H | cyclopentyl | Cl | CONHSO$_2$CH$_3$ | |
| 412 | i-propyl | H | cyclopentyl | Cl | CONHSO$_2$CH$_2$CH$_3$ | |
| 413 | i-propyl | H | cyclopentyl | Cl | (isoxazol-3-ylamino)carbonyl | |
| 414 | i-propyl | H | cyclopentyl | Cl | [(4-methyl-4H-1,2,4-triazol-3-yl)amino]carbonyl | |
| 415 | i-propyl | H | sec-butyl | Cl | CONHCONHCH$_3$ | |
| 416 | i-propyl | H | sec-butyl | Cl | CONHSO$_2$CF$_3$ | |
| 417 | i-propyl | H | sec-butyl | Cl | CONHSO$_2$CH$_3$ | |
| 418 | i-propyl | H | sec-butyl | Cl | CONHSO$_2$CH$_2$CH$_3$ | |
| 419 | i-propyl | H | sec-butyl | Cl | (isoxazol-3-ylamino)carbonyl | |
| 420 | i-propyl | H | sec-butyl | Cl | [(4-methyl-4H-1,2,4-triazol-3-yl)amino]carbonyl | |
| 421 | i-butyl | H | 2-chloro-6-fluorophenyl | Cl | CONHCONHCH$_3$ | |
| 422 | i-butyl | H | 2-chloro-6-fluorophenyl | Cl | CONHSO$_2$CF$_3$ | |
| 423 | i-butyl | H | 2-chloro-6-fluorophenyl | Cl | CONHSO$_2$CH$_3$ | |
| 424 | i-butyl | H | 2-chloro-6-fluorophenyl | Cl | CONHSO$_2$CH$_2$CH$_3$ | |
| 425 | i-butyl | H | 2-chloro-6-fluorophenyl | Cl | (isoxazol-3-ylamino)carbonyl | |
| 426 | i-butyl | H | 2-chloro-6-fluorophenyl | Cl | [(4-methyl-4H-1,2,4-triazol-3-yl)amino]carbonyl | |
| 427 | i-butyl | H | 2,4,6-trifluorophenyl | Cl | CONHCONHCH$_3$ | |
| 428 | i-butyl | H | 2,4,6-trifluorophenyl | Cl | CONHSO$_2$CF$_3$ | |
| 429 | i-butyl | H | 2,4,6-trifluorophenyl | Cl | CONHSO$_2$CH$_3$ | 3.59* |
| 430 | i-butyl | H | 2,4,6-trifluorophenyl | Cl | CONHSO$_2$CH$_2$CH$_3$ | |
| 431 | i-butyl | H | 2,4,6-trifluorophenyl | Cl | (isoxazol-3-ylamino)carbonyl | |
| 432 | i-butyl | H | 2,4,6-trifluorophenyl | Cl | [(4-methyl-4H-1,2,4-triazol-3-yl)amino]carbonyl | |
| 433 | i-butyl | H | 2-chloro-4-fluorophenyl | Cl | CONHCONHCH$_3$ | |
| 434 | i-butyl | H | 2-chloro-4-fluorophenyl | Cl | CONHSO$_2$CF$_3$ | |
| 435 | i-butyl | H | 2-chloro-4-fluorophenyl | Cl | CONHSO$_2$CH$_3$ | 3.82* |
| 436 | i-butyl | H | 2-chloro-4-fluorophenyl | Cl | CONHSO$_2$CH$_2$CH$_3$ | |

TABLE 1-continued

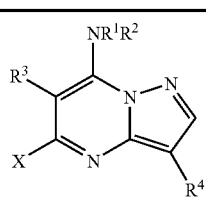

| Ex. No. | R1 or —R1+R2— | R2 | R3 | X | R4 | log p |
|---|---|---|---|---|---|---|
| 437 | i-butyl | H | 2-chloro-4-fluorophenyl | Cl | (isoxazol-3-ylamino)carbonyl | |
| 438 | i-butyl | H | 2-chloro-4-fluorophenyl | Cl | [(4-methyl-4H-1,2,4-triazol-3-yl)amino]carbonyl | |
| 439 | i-butyl | H | 2-chlorophenyl | Cl | CONHCONHCH$_3$ | |
| 440 | i-butyl | H | 2-chlorophenyl | Cl | CONHSO$_2$CF$_3$ | |
| 441 | i-butyl | H | 2-chlorophenyl | Cl | CONHSO$_2$CH$_3$ | 3.78* |
| 442 | i-butyl | H | 2-chlorophenyl | Cl | CONHSO$_2$CH$_2$CH$_3$ | |
| 443 | i-butyl | H | 2-chlorophenyl | Cl | (isoxazol-3-ylamino)carbonyl | |
| 444 | i-butyl | H | 2-chlorophenyl | Cl | [(4-methyl-4H-1,2,4-triazol-3-yl)amino]carbonyl | |
| 445 | i-butyl | H | 5-Cl-pyrimidin-4-yl | Cl | CONHCONHCH$_3$ | |
| 446 | i-butyl | H | 5-Cl-pyrimidin-4-yl | Cl | CONHSO$_2$CF$_3$ | |
| 447 | i-butyl | H | 5-Cl-pyrimidin-4-yl | Cl | CONHSO$_2$CH$_3$ | |
| 448 | i-butyl | H | 5-Cl-pyrimidin-4-yl | Cl | CONHSO$_2$CH$_2$CH$_3$ | |
| 449 | i-butyl | H | 5-Cl-pyrimidin-4-yl | Cl | (isoxazol-3-ylamino)carbonyl | |
| 450 | i-butyl | H | 5-Cl-pyrimidin-4-yl | Cl | [(4-methyl-4H-1,2,4-triazol-3-yl)amino]carbonyl | |
| 451 | i-butyl | H | 2-chloro-4,6-difluorophenyl | Cl | CONHCONHCH$_3$ | |
| 452 | i-butyl | H | 2-chloro-4,6-difluorophenyl | Cl | CONHSO$_2$CF$_3$ | |
| 453 | i-butyl | H | 2-chloro-4,6-difluorophenyl | Cl | CONHSO$_2$CH$_3$ | |
| 454 | i-butyl | H | 2-chloro-4,6-difluorophenyl | Cl | CONHSO$_2$CH$_2$CH$_3$ | |
| 455 | i-butyl | H | 2-chloro-4,6-difluorophenyl | Cl | (isoxazol-3-ylamino)carbonyl | |
| 456 | i-butyl | H | 2-chloro-4,6-difluorophenyl | Cl | [(4-methyl-4H-1,2,4-triazol-3-yl)amino]carbonyl | |
| 457 | i-butyl | H | 2,4-dichlorophenyl | Cl | CONHCONHCH$_3$ | |
| 458 | i-butyl | H | 2,4-dichlorophenyl | Cl | CONHSO$_2$CF$_3$ | |
| 459 | i-butyl | H | 2,4-dichlorophenyl | Cl | CONHSO$_2$CH$_3$ | 4.26* |
| 460 | i-butyl | H | 2,4-dichlorophenyl | Cl | CONHSO$_2$CH$_2$CH$_3$ | |
| 461 | i-butyl | H | 2,4-dichlorophenyl | Cl | (isoxazol-3-ylamino)carbonyl | |
| 462 | i-butyl | H | 2,4-dichlorophenyl | Cl | [(4-methyl-4H-1,2,4-triazol-3-yl)amino]carbonyl | |
| 463 | i-butyl | H | 4-chloro-2,6-difluorophenyl | Cl | CONHCONHCH$_3$ | |
| 464 | i-butyl | H | 4-chloro-2,6-difluorophenyl | Cl | CONHSO$_2$CF$_3$ | |
| 465 | i-butyl | H | 4-chloro-2,6-difluorophenyl | Cl | CONHSO$_2$CH$_3$ | 3.97* |
| 466 | i-butyl | H | 4-chloro-2,6-difluorophenyl | Cl | CONHSO$_2$CH$_2$CH$_3$ | |
| 467 | i-butyl | H | 4-chloro-2,6-difluorophenyl | Cl | (isoxazol-3-ylamino)carbonyl | |
| 468 | i-butyl | H | 4-chloro-2,6-difluorophenyl | Cl | [(4-methyl-4H-1,2,4-triazol-3-yl)amino]carbonyl | |
| 469 | i-butyl | H | 2,6-difluoro-4-methylphenyl | Cl | CONHCONHCH$_3$ | |
| 470 | i-butyl | H | 2,6-difluoro-4-methylphenyl | Cl | CONHSO$_2$CF$_3$ | |
| 471 | i-butyl | H | 2,6-difluoro-4-methylphenyl | Cl | CONHSO$_2$CH$_3$ | |
| 472 | i-butyl | H | 2,6-difluoro-4-methylphenyl | Cl | CONHSO$_2$CH$_2$CH$_3$ | |
| 473 | i-butyl | H | 2,6-difluoro-4-methylphenyl | Cl | (isoxazol-3-ylamino)carbonyl | |
| 474 | i-butyl | H | 2,6-difluoro-4-methylphenyl | Cl | [(4-methyl-4H-1,2,4-triazol-3-yl)amino]carbonyl | |
| 475 | i-butyl | H | 2-chloro-5-fluorophenyl | Cl | CONHCONHCH$_3$ | |
| 476 | i-butyl | H | 2-chloro-5-fluorophenyl | Cl | CONHSO$_2$CF$_3$ | |
| 477 | i-butyl | H | 2-chloro-5-fluorophenyl | Cl | CONHSO$_2$CH$_3$ | |
| 478 | i-butyl | H | 2-chloro-5-fluorophenyl | Cl | CONHSO$_2$CH$_2$CH$_3$ | |
| 479 | i-butyl | H | 2-chloro-5-fluorophenyl | Cl | (isoxazol-3-ylamino)carbonyl | |

TABLE 1-continued

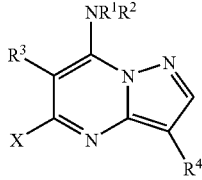

| Ex. No. | R¹ or —R¹⁺R²— | R² R3 | X | R4 | log p |
|---|---|---|---|---|---|
| 480 | i-butyl | H 2-chloro-5-fluorophenyl | Cl | [(4-methyl-4H-1,2,4-triazol-3-yl)amino]carbonyl | |
| 481 | i-butyl | H 3-chloro-2-thienyl | Cl | CONHCONHCH$_3$ | |
| 482 | i-butyl | H 3-chloro-2-thienyl | Cl | CONHSO$_2$CF$_3$ | |
| 483 | i-butyl | H 3-chloro-2-thienyl | Cl | CONHSO$_2$CH$_3$ | |
| 484 | i-butyl | H 3-chloro-2-thienyl | Cl | CONHSO$_2$CH$_2$CH$_3$ | |
| 485 | i-butyl | H 3-chloro-2-thienyl | Cl | (isoxazol-3-ylamino)carbonyl | |
| 486 | i-butyl | H 3-chloro-2-thienyl | Cl | [(4-methyl-4H-1,2,4-triazol-3-yl)amino]carbonyl | |
| 487 | i-butyl | H phenyl | Cl | CONHCONHCH$_3$ | |
| 488 | i-butyl | H phenyl | Cl | CONHSO$_2$CF$_3$ | |
| 489 | i-butyl | H phenyl | Cl | CONHSO$_2$CH$_3$ | |
| 490 | i-butyl | H phenyl | Cl | CONHSO$_2$CH$_2$CH$_3$ | |
| 491 | i-butyl | H phenyl | Cl | (isoxazol-3-ylamino)carbonyl | |
| 492 | i-butyl | H phenyl | Cl | [(4-methyl-4H-1,2,4-triazol-3-yl)amino]carbonyl | |
| 493 | i-butyl | H cyclopentyl | Cl | CONHCONHCH$_3$ | |
| 494 | i-butyl | H cyclopentyl | Cl | CONHSO$_2$CF$_3$ | |
| 495 | i-butyl | H cyclopentyl | Cl | CONHSO$_2$CH$_3$ | |
| 496 | i-butyl | H cyclopentyl | Cl | CONHSO$_2$CH$_2$CH$_3$ | |
| 497 | i-butyl | H cyclopentyl | Cl | (isoxazol-3-ylamino)carbonyl | |
| 498 | i-butyl | H cyclopentyl | Cl | [(4-methyl-4H-1,2,4-triazol-3-yl)amino]carbonyl | |
| 499 | i-butyl | H sec-butyl | Cl | CONHCONHCH$_3$ | |
| 500 | i-butyl | H sec-butyl | Cl | CONHSO$_2$CF$_3$ | |
| 501 | i-butyl | H sec-butyl | Cl | CONHSO$_2$CH$_3$ | |
| 502 | i-butyl | H sec-butyl | Cl | CONHSO$_2$CH$_2$CH$_3$ | |
| 503 | i-butyl | H sec-butyl | Cl | (isoxazol-3-ylamino)carbonyl | |
| 504 | i-butyl | H sec-butyl | Cl | [(4-methyl-4H-1,2,4-triazol-3-yl)amino]carbonyl | |
| 505 | CH$_2$—C(CH$_3$)$_3$ | H 2-chloro-6-fluorophenyl | Cl | CONHCONHCH$_3$ | |
| 506 | CH$_2$—C(CH$_3$)$_3$ | H 2-chloro-6-fluorophenyl | Cl | CONHSO$_2$CF$_3$ | |
| 507 | CH$_2$—C(CH$_3$)$_3$ | H 2-chloro-6-fluorophenyl | Cl | CONHSO$_2$CH$_3$ | 4.04* |
| 508 | CH$_2$—C(CH$_3$)$_3$ | H 2-chloro-6-fluorophenyl | Cl | CONHSO$_2$CH$_2$CH$_3$ | |
| 509 | CH$_2$—C(CH$_3$)$_3$ | H 2-chloro-6-fluorophenyl | Cl | (isoxazol-3-ylamino)carbonyl | |
| 510 | CH$_2$—C(CH$_3$)$_3$ | H 2-chloro-6-fluorophenyl | Cl | [(4-methyl-4H-1,2,4-triazol-3-yl)amino]carbonyl | |
| 511 | CH$_2$—C(CH$_3$)$_3$ | H 2,4,6-trifluorophenyl | Cl | CONHCONHCH$_3$ | |
| 512 | CH$_2$—C(CH$_3$)$_3$ | H 2,4,6-trifluorophenyl | Cl | CONHSO$_2$CF$_3$ | |
| 513 | CH$_2$—C(CH$_3$)$_3$ | H 2,4,6-trifluorophenyl | Cl | CONHSO$_2$CH$_3$ | 3.9* |
| 514 | CH$_2$—C(CH$_3$)$_3$ | H 2,4,6-trifluorophenyl | Cl | CONHSO$_2$CH$_2$CH$_3$ | |
| 515 | CH$_2$—C(CH$_3$)$_3$ | H 2,4,6-trifluorophenyl | Cl | (isoxazol-3-ylamino)carbonyl | |
| 516 | CH$_2$—C(CH$_3$)$_3$ | H 2,4,6-trifluorophenyl | Cl | [(4-methyl-4H-1,2,4-triazol-3-yl)amino]carbonyl | |
| 517 | CH$_2$—C(CH$_3$)$_3$ | H 2-chloro-4-fluorophenyl | Cl | CONHCONHCH$_3$ | |
| 518 | CH$_2$—C(CH$_3$)$_3$ | H 2-chloro-4-fluorophenyl | Cl | CONHSO$_2$CF$_3$ | |
| 519 | CH$_2$—C(CH$_3$)$_3$ | H 2-chloro-4-fluorophenyl | Cl | CONHSO$_2$CH$_3$ | 4.19* |
| 520 | CH$_2$—C(CH$_3$)$_3$ | H 2-chloro-4-fluorophenyl | Cl | CONHSO$_2$CH$_2$CH$_3$ | |
| 521 | CH$_2$—C(CH$_3$)$_3$ | H 2-chloro-4-fluorophenyl | Cl | (isoxazol-3-ylamino)carbonyl | |
| 522 | CH$_2$—C(CH$_3$)$_3$ | H 2-chloro-4-fluorophenyl | Cl | [(4-methyl-4H-1,2,4-triazol-3-yl)amino]carbonyl | |
| 523 | CH$_2$—C(CH$_3$)$_3$ | H 2-chlorophenyl | Cl | CONHCONHCH$_3$ | |
| 524 | CH$_2$—C(CH$_3$)$_3$ | H 2-chlorophenyl | Cl | CONHSO$_2$CF$_3$ | |
| 525 | CH$_2$—C(CH$_3$)$_3$ | H 2-chlorophenyl | Cl | CONHSO$_2$CH$_3$ | 4.17* |
| 526 | CH$_2$—C(CH$_3$)$_3$ | H 2-chlorophenyl | Cl | CONHSO$_2$CH$_2$CH$_3$ | |
| 527 | CH$_2$—C(CH$_3$)$_3$ | H 2-chlorophenyl | Cl | (isoxazol-3-ylamino)carbonyl | |
| 528 | CH$_2$—C(CH$_3$)$_3$ | H 2-chlorophenyl | Cl | [(4-methyl-4H-1,2,4-triazol-3-yl)amino]carbonyl | |
| 529 | CH$_2$—C(CH$_3$)$_3$ | H 5-Cl-pyrimidin-4-yl | Cl | CONHCONHCH$_3$ | |
| 530 | CH$_2$—C(CH$_3$)$_3$ | H 5-Cl-pyrimidin-4-yl | Cl | CONHSO$_2$CF$_3$ | |
| 531 | CH$_2$—C(CH$_3$)$_3$ | H 5-Cl-pyrimidin-4-yl | Cl | CONHSO$_2$CH$_3$ | |
| 532 | CH$_2$—C(CH$_3$)$_3$ | H 5-Cl-pyrimidin-4-yl | Cl | CONHSO$_2$CH$_2$CH$_3$ | |
| 533 | CH$_2$—C(CH$_3$)$_3$ | H 5-Cl-pyrimidin-4-yl | Cl | (isoxazol-3-ylamino)carbonyl | |
| 534 | CH$_2$—C(CH$_3$)$_3$ | H 5-Cl-pyrimidin-4-yl | Cl | [(4-methyl-4H-1,2,4-triazol-3-yl)amino]carbonyl | |

TABLE 1-continued

| Ex. No. | R¹ or —R¹⁺R²— | R² | R3 | X | R4 | log p |
|---|---|---|---|---|---|---|
| 535 | CH₂—C(CH₃)₃ | H | 2-chloro-4,6-difluorophenyl | Cl | CONHCONHCH₃ | |
| 536 | CH₂—C(CH₃)₃ | H | 2-chloro-4,6-difluorophenyl | Cl | CONHSO₂CF₃ | |
| 537 | CH₂—C(CH₃)₃ | H | 2-chloro-4,6-difluorophenyl | Cl | CONHSO₂CH₃ | |
| 538 | CH₂—C(CH₃)₃ | H | 2-chloro-4,6-difluorophenyl | Cl | CONHSO₂CH₂CH₃ | |
| 539 | CH₂—C(CH₃)₃ | H | 2-chloro-4,6-difluorophenyl | Cl | (isoxazol-3-ylamino)carbonyl | |
| 540 | CH₂—C(CH₃)₃ | H | 2-chloro-4,6-difluorophenyl | Cl | [(4-methyl-4H-1,2,4-triazol-3-yl)amino]carbonyl | |
| 541 | CH₂—C(CH₃)₃ | H | 2,4-dichlorophenyl | Cl | CONHCONHCH₃ | |
| 542 | CH₂—C(CH₃)₃ | H | 2,4-dichlorophenyl | Cl | CONHSO₂CF₃ | |
| 543 | CH₂—C(CH₃)₃ | H | 2,4-dichlorophenyl | Cl | CONHSO₂CH₃ | 4.63* |
| 544 | CH₂—C(CH₃)₃ | H | 2,4-dichlorophenyl | Cl | CONHSO₂CH₂CH₃ | |
| 545 | CH₂—C(CH₃)₃ | H | 2,4-dichlorophenyl | Cl | (isoxazol-3-ylamino)carbonyl | |
| 546 | CH₂—C(CH₃)₃ | H | 2,4-dichlorophenyl | Cl | [(4-methyl-4H-1,2,4-triazol-3-yl)amino]carbonyl | |
| 547 | CH₂—C(CH₃)₃ | H | 4-chloro-2,6-difluorophenyl | Cl | CONHCONHCH₃ | |
| 548 | CH₂—C(CH₃)₃ | H | 4-chloro-2,6-difluorophenyl | Cl | CONHSO₂CF₃ | |
| 549 | CH₂—C(CH₃)₃ | H | 4-chloro-2,6-difluorophenyl | Cl | CONHSO₂CH₃ | 4.31* |
| 550 | CH₂—C(CH₃)₃ | H | 4-chloro-2,6-difluorophenyl | Cl | CONHSO₂CH₂CH₃ | |
| 551 | CH₂—C(CH₃)₃ | H | 4-chloro-2,6-difluorophenyl | Cl | (isoxazol-3-ylamino)carbonyl | |
| 552 | CH₂—C(CH₃)₃ | H | 4-chloro-2,6-difluorophenyl | Cl | [(4-methyl-4H-1,2,4-triazol-3-yl)amino]carbonyl | |
| 553 | CH₂—C(CH₃)₃ | H | 2,6-difluoro-4-methylphenyl | Cl | CONHCONHCH₃ | |
| 554 | CH₂—C(CH₃)₃ | H | 2,6-difluoro-4-methylphenyl | Cl | CONHSO₂CF₃ | |
| 555 | CH₂—C(CH₃)₃ | H | 2,6-difluoro-4-methylphenyl | Cl | CONHSO₂CH₃ | |
| 556 | CH₂—C(CH₃)₃ | H | 2,6-difluoro-4-methylphenyl | Cl | CONHSO₂CH₂CH₃ | |
| 557 | CH₂—C(CH₃)₃ | H | 2,6-difluoro-4-methylphenyl | Cl | (isoxazol-3-ylamino)carbonyl | |
| 558 | CH₂—C(CH₃)₃ | H | 2,6-difluoro-4-methylphenyl | Cl | [(4-methyl-4H-1,2,4-triazol-3-yl)amino]carbonyl | |
| 559 | CH₂—C(CH₃)₃ | H | 2-chloro-5-fluorophenyl | Cl | CONHCONHCH₃ | |
| 560 | CH₂—C(CH₃)₃ | H | 2-chloro-5-fluorophenyl | Cl | CONHSO₂CF₃ | |
| 561 | CH₂—C(CH₃)₃ | H | 2-chloro-5-fluorophenyl | Cl | CONHSO₂CH₃ | |
| 562 | CH₂—C(CH₃)₃ | H | 2-chloro-5-fluorophenyl | Cl | CONHSO₂CH₂CH₃ | |
| 563 | CH₂—C(CH₃)₃ | H | 2-chloro-5-fluorophenyl | Cl | (isoxazol-3-ylamino)carbonyl | |
| 564 | CH₂—C(CH₃)₃ | H | 2-chloro-5-fluorophenyl | Cl | [(4-methyl-4H-1,2,4-triazol-3-yl)amino]carbonyl | |
| 565 | CH₂—C(CH₃)₃ | H | 3-chloro-2-thienyl | Cl | CONHCONHCH₃ | |
| 566 | CH₂—C(CH₃)₃ | H | 3-chloro-2-thienyl | Cl | CONHSO₂CF₃ | |
| 567 | CH₂—C(CH₃)₃ | H | 3-chloro-2-thienyl | Cl | CONHSO₂CH₃ | |
| 568 | CH₂—C(CH₃)₃ | H | 3-chloro-2-thienyl | Cl | CONHSO₂CH₂CH₃ | |
| 569 | CH₂—C(CH₃)₃ | H | 3-chloro-2-thienyl | Cl | (isoxazol-3-ylamino)carbonyl | |
| 570 | CH₂—C(CH₃)₃ | H | 3-chloro-2-thienyl | Cl | [(4-methyl-4H-1,2,4-triazol-3-yl)amino]carbonyl | |
| 571 | CH₂—C(CH₃)₃ | H | phenyl | Cl | CONHCONHCH₃ | |
| 572 | CH₂—C(CH₃)₃ | H | phenyl | Cl | CONHSO₂CF₃ | |
| 573 | CH₂—C(CH₃)₃ | H | phenyl | Cl | CONHSO₂CH₃ | |
| 574 | CH₂—C(CH₃)₃ | H | phenyl | Cl | CONHSO₂CH₂CH₃ | |
| 575 | CH₂—C(CH₃)₃ | H | phenyl | Cl | (isoxazol-3-ylamino)carbonyl | |
| 576 | CH₂—C(CH₃)₃ | H | phenyl | Cl | [(4-methyl-4H-1,2,4-triazol-3-yl)amino]carbonyl | |
| 577 | CH₂—C(CH₃)₃ | H | cyclopentyl | Cl | CONHCONHCH₃ | |

TABLE 1-continued

| Ex. No. | R¹ or —R¹⁺R²— | R² R3 | X | R4 | log p |
|---|---|---|---|---|---|
| 578 | CH₂—C(CH₃)₃ | H cyclopentyl | Cl | CONHSO₂CF₃ | |
| 579 | CH₂—C(CH₃)₃ | H cyclopentyl | Cl | CONHSO₂CH₃ | |
| 580 | CH₂—C(CH₃)₃ | H cyclopentyl | Cl | CONHSO₂CH₂CH₃ | |
| 581 | CH₂—C(CH₃)₃ | H cyclopentyl | Cl | (isoxazol-3-ylamino)carbonyl | |
| 582 | CH₂—C(CH₃)₃ | H cyclopentyl | Cl | [(4-methyl-4H-1,2,4-triazol-3-yl)amino]carbonyl | |
| 583 | CH₂—C(CH₃)₃ | H sec-butyl | Cl | CONHCONHCH₃ | |
| 584 | CH₂—C(CH₃)₃ | H sec-butyl | Cl | CONHSO₂CF₃ | |
| 585 | CH₂—C(CH₃)₃ | H sec-butyl | Cl | CONHSO₂CH₃ | |
| 586 | CH₂—C(CH₃)₃ | H sec-butyl | Cl | CONHSO₂CH₂CH₃ | |
| 587 | CH₂—C(CH₃)₃ | H sec-butyl | Cl | (isoxazol-3-ylamino)carbonyl | |
| 588 | CH₂—C(CH₃)₃ | H sec-butyl | Cl | [(4-methyl-4H-1,2,4-triazol-3-yl)amino]carbonyl | |
| 589 | —CH₂—CH₂—CH₂—CH(CH₃)— | 2-chloro-6-fluorophenyl | Cl | CONHCONHCH₃ | |
| 590 | —CH₂—CH₂—CH₂—CH(CH₃)— | 2-chloro-6-fluorophenyl | Cl | CONHSO₂CF₃ | |
| 591 | —CH₂—CH₂—CH₂—CH(CH₃)— | 2-chloro-6-fluorophenyl | Cl | CONHSO₂CH₃ | |
| 592 | —CH₂—CH₂—CH₂—CH(CH₃)— | 2-chloro-6-fluorophenyl | Cl | CONHSO₂CH₂CH₃ | |
| 593 | —CH₂—CH₂—CH₂—CH(CH₃)— | 2-chloro-6-fluorophenyl | Cl | (isoxazol-3-ylamino)carbonyl | |
| 594 | —CH₂—CH₂—CH₂—CH(CH₃)— | 2-chloro-6-fluorophenyl | Cl | [(4-methyl-4H-1,2,4-triazol-3-yl)amino]carbonyl | |
| 595 | —CH₂—CH₂—CH₂—CH(CH₃)— | 2,4,6-trifluorophenyl | Cl | CONHCONHCH₃ | |
| 596 | —CH₂—CH₂—CH₂—CH(CH₃)— | 2,4,6-trifluorophenyl | Cl | CONHSO₂CF₃ | |
| 597 | —CH₂—CH₂—CH₂—CH(CH₃)— | 2,4,6-trifluorophenyl | Cl | CONHSO₂CH₃ | |
| 598 | —CH₂—CH₂—CH₂—CH(CH₃)— | 2,4,6-trifluorophenyl | Cl | CONHSO₂CH₂CH₃ | |
| 599 | —CH₂—CH₂—CH₂—CH(CH₃)— | 2,4,6-trifluorophenyl | Cl | (isoxazol-3-ylamino)carbonyl | |
| 600 | —CH₂—CH₂—CH₂—CH(CH₃)— | 2,4,6-trifluorophenyl | Cl | [(4-methyl-4H-1,2,4-triazol-3-yl)amino]carbonyl | |
| 601 | —CH₂—CH₂—CH₂—CH(CH₃)— | 2-chloro-4-fluorophenyl | Cl | CONHCONHCH₃ | |
| 602 | —CH₂—CH₂—CH₂—CH(CH₃)— | 2-chloro-4-fluorophenyl | Cl | CONHSO₂CF₃ | |
| 603 | —CH₂—CH₂—CH₂—CH(CH₃)— | 2-chloro-4-fluorophenyl | Cl | CONHSO₂CH₃ | |
| 604 | —CH₂—CH₂—CH₂—CH(CH₃)— | 2-chloro-4-fluorophenyl | Cl | CONHSO₂CH₂CH₃ | |
| 605 | —CH₂—CH₂—CH₂—CH(CH₃)— | 2-chloro-4-fluorophenyl | Cl | (isoxazol-3-ylamino)carbonyl | |
| 606 | —CH₂—CH₂—CH₂—CH(CH₃)— | 2-chloro-4-fluorophenyl | Cl | [(4-methyl-4H-1,2,4-triazol-3-yl)amino]carbonyl | |
| 607 | —CH₂—CH₂—CH₂—CH(CH₃)— | 2-chlorophenyl | Cl | CONHCONHCH₃ | |
| 608 | —CH₂—CH₂—CH₂—CH(CH₃)— | 2-chlorophenyl | Cl | CONHSO₂CF₃ | |
| 609 | —CH₂—CH₂—CH₂—CH(CH₃)— | 2-chlorophenyl | Cl | CONHSO₂CH₃ | |
| 610 | —CH₂—CH₂—CH₂—CH(CH₃)— | 2-chlorophenyl | Cl | CONHSO₂CH₂CH₃ | |
| 611 | —CH₂—CH₂—CH₂—CH(CH₃)— | 2-chlorophenyl | Cl | (isoxazol-3-ylamino)carbonyl | |
| 612 | —CH₂—CH₂—CH₂—CH(CH₃)— | 2-chlorophenyl | Cl | [(4-methyl-4H-1,2,4-triazol-3-yl)amino]carbonyl | |
| 613 | —CH₂—CH₂—CH₂—CH(CH₃)— | 5-Cl-pyrimidin-4-yl | Cl | CONHCONHCH₃ | |
| 614 | —CH₂—CH₂—CH₂—CH(CH₃)— | 5-Cl-pyrimidin-4-yl | Cl | CONHSO₂CF₃ | |
| 615 | —CH₂—CH₂—CH₂—CH(CH₃)— | 5-Cl-pyrimidin-4-yl | Cl | CONHSO₂CH₃ | |
| 616 | —CH₂—CH₂—CH₂—CH(CH₃)— | 5-Cl-pyrimidin-4-yl | Cl | CONHSO₂CH₂CH₃ | |
| 617 | —CH₂—CH₂—CH₂—CH(CH₃)— | 5-Cl-pyrimidin-4-yl | Cl | (isoxazol-3-ylamino)carbonyl | |
| 618 | —CH₂—CH₂—CH₂—CH(CH₃)— | 5-Cl-pyrimidin-4-yl | Cl | [(4-methyl-4H-1,2,4-triazol-3-yl)amino]carbonyl | |
| 619 | —CH₂—CH₂—CH₂—CH(CH₃)— | 2-chloro-4,6-difluorophenyl | Cl | CONHCONHCH₃ | |
| 620 | —CH₂—CH₂—CH₂—CH(CH₃)— | 2-chloro-4,6-difluorophenyl | Cl | CONHSO₂CF₃ | |
| 621 | —CH₂—CH₂—CH₂—CH(CH₃)— | 2-chloro-4,6-difluorophenyl | Cl | CONHSO₂CH₃ | |
| 622 | —CH₂—CH₂—CH₂—CH(CH₃)— | 2-chloro-4,6-difluorophenyl | Cl | CONHSO₂CH₂CH₃ | |
| 623 | —CH₂—CH₂—CH₂—CH(CH₃)— | 2-chloro-4,6-difluorophenyl | Cl | (isoxazol-3-ylamino)carbonyl | |
| 624 | —CH₂—CH₂—CH₂—CH(CH₃)— | 2-chloro-4,6-difluorophenyl | Cl | [(4-methyl-4H-1,2,4-triazol-3-yl)amino]carbonyl | |
| 625 | —CH₂—CH₂—CH₂—CH(CH₃)— | 2,4-dichlorophenyl | Cl | CONHCONHCH₃ | |
| 626 | —CH₂—CH₂—CH₂—CH(CH₃)— | 2,4-dichlorophenyl | Cl | CONHSO₂CF₃ | |
| 627 | —CH₂—CH₂—CH₂—CH(CH₃)— | 2,4-dichlorophenyl | Cl | CONHSO₂CH₃ | |
| 628 | —CH₂—CH₂—CH₂—CH(CH₃)— | 2,4-dichlorophenyl | Cl | CONHSO₂CH₂CH₃ | |
| 629 | —CH₂—CH₂—CH₂—CH(CH₃)— | 2,4-dichlorophenyl | Cl | (isoxazol-3-ylamino)carbonyl | |

TABLE 1-continued

| Ex. No. | R¹ or —R¹⁺R²— | R² R3 | X | R4 | log p |
|---|---|---|---|---|---|
| 630 | —CH₂—CH₂—CH₂—CH(CH₃)— | 2,4-dichlorophenyl | Cl | [(4-methyl-4H-1,2,4-triazol-3-yl)amino]carbonyl | |
| 631 | —CH₂—CH₂—CH₂—CH(CH₃)— | 4-chloro-2,6-difluorophenyl | Cl | CONHCONHCH₃ | |
| 632 | —CH₂—CH₂—CH₂—CH(CH₃)— | 4-chloro-2,6-difluorophenyl | Cl | CONHSO₂CF₃ | |
| 633 | —CH₂—CH₂—CH₂—CH(CH₃)— | 4-chloro-2,6-difluorophenyl | Cl | CONHSO₂CH₃ | |
| 634 | —CH₂—CH₂—CH₂—CH(CH₃)— | 4-chloro-2,6-difluorophenyl | Cl | CONHSO₂CH₂CH₃ | |
| 635 | —CH₂—CH₂—CH₂—CH(CH₃)— | 4-chloro-2,6-difluorophenyl | Cl | (isoxazol-3-ylamino)carbonyl | |
| 636 | —CH₂—CH₂—CH₂—CH(CH₃)— | 4-chloro-2,6-difluorophenyl | Cl | [(4-methyl-4H-1,2,4-triazol-3-yl)amino]carbonyl | |
| 637 | —CH₂—CH₂—CH₂—CH(CH₃)— | 2,6-difluoro-4-methylphenyl | Cl | CONHCONHCH₃ | |
| 638 | —CH₂—CH₂—CH₂—CH(CH₃)— | 2,6-difluoro-4-methylphenyl | Cl | CONHSO₂CF₃ | |
| 639 | —CH₂—CH₂—CH₂—CH(CH₃)— | 2,6-difluoro-4-methylphenyl | Cl | CONHSO₂CH₃ | |
| 640 | —CH₂—CH₂—CH₂—CH(CH₃)— | 2,6-difluoro-4-methylphenyl | Cl | CONHSO₂CH₂CH₃ | |
| 641 | —CH₂—CH₂—CH₂—CH(CH₃)— | 2,6-difluoro-4-methylphenyl | Cl | (isoxazol-3-ylamino)carbonyl | |
| 642 | —CH₂—CH₂—CH₂—CH(CH₃)— | 2,6-difluoro-4-methylphenyl | Cl | [(4-methyl-4H-1,2,4-triazol-3-yl)amino]carbonyl | |
| 643 | —CH₂—CH₂—CH₂—CH(CH₃)— | 2-chloro-5-fluorophenyl | Cl | CONHCONHCH₃ | |
| 644 | —CH₂—CH₂—CH₂—CH(CH₃)— | 2-chloro-5-fluorophenyl | Cl | CONHSO₂CF₃ | |
| 645 | —CH₂—CH₂—CH₂—CH(CH₃)— | 2-chloro-5-fluorophenyl | Cl | CONHSO₂CH₃ | |
| 646 | —CH₂—CH₂—CH₂—CH(CH₃)— | 2-chloro-5-fluorophenyl | Cl | CONHSO₂CH₂CH₃ | |
| 647 | —CH₂—CH₂—CH₂—CH(CH₃)— | 2-chloro-5-fluorophenyl | Cl | (isoxazol-3-ylamino)carbonyl | |
| 648 | —CH₂—CH₂—CH₂—CH(CH₃)— | 2-chloro-5-fluorophenyl | Cl | [(4-methyl-4H-1,2,4-triazol-3-yl)amino]carbonyl | |
| 649 | —CH₂—CH₂—CH₂—CH(CH₃)— | 3-chloro-2-thienyl | Cl | CONHCONHCH₃ | |
| 650 | —CH₂—CH₂—CH₂—CH(CH₃)— | 3-chloro-2-thienyl | Cl | CONHSO₂CF₃ | |
| 651 | —CH₂—CH₂—CH₂—CH(CH₃)— | 3-chloro-2-thienyl | Cl | CONHSO₂CH₃ | |
| 652 | —CH₂—CH₂—CH₂—CH(CH₃)— | 3-chloro-2-thienyl | Cl | CONHSO₂CH₂CH₃ | |
| 653 | —CH₂—CH₂—CH₂—CH(CH₃)— | 3-chloro-2-thienyl | Cl | (isoxazol-3-ylamino)carbonyl | |
| 654 | —CH₂—CH₂—CH₂—CH(CH₃)— | 3-chloro-2-thienyl | Cl | [(4-methyl-4H-1,2,4-triazol-3-yl)amino]carbonyl | |
| 655 | —CH₂—CH₂—CH₂—CH(CH₃)— | phenyl | Cl | CONHCONHCH₃ | |
| 656 | —CH₂—CH₂—CH₂—CH(CH₃)— | phenyl | Cl | CONHSO₂CF₃ | |
| 657 | —CH₂—CH₂—CH₂—CH(CH₃)— | phenyl | Cl | CONHSO₂CH₃ | |
| 658 | —CH₂—CH₂—CH₂—CH(CH₃)— | phenyl | Cl | CONHSO₂CH₂CH₃ | |
| 659 | —CH₂—CH₂—CH₂—CH(CH₃)— | phenyl | Cl | (isoxazol-3-ylamino)carbonyl | |
| 660 | —CH₂—CH₂—CH₂—CH(CH₃)— | phenyl | Cl | [(4-methyl-4H-1,2,4-triazol-3-yl)amino]carbonyl | |
| 661 | —CH₂—CH₂—CH₂—CH(CH₃)— | cyclopentyl | Cl | CONHCONHCH₃ | |
| 662 | —CH₂—CH₂—CH₂—CH(CH₃)— | cyclopentyl | Cl | CONHSO₂CF₃ | |
| 663 | —CH₂—CH₂—CH₂—CH(CH₃)— | cyclopentyl | Cl | CONHSO₂CH₃ | |
| 664 | —CH₂—CH₂—CH₂—CH(CH₃)— | cyclopentyl | Cl | CONHSO₂CH₂CH₃ | |
| 665 | —CH₂—CH₂—CH₂—CH(CH₃)— | cyclopentyl | Cl | (isoxazol-3-ylamino)carbonyl | |
| 666 | —CH₂—CH₂—CH₂—CH(CH₃)— | cyclopentyl | Cl | [(4-methyl-4H-1,2,4-triazol-3-yl)amino]carbonyl | |
| 667 | —CH₂—CH₂—CH₂—CH(CH₃)— | sec-butyl | Cl | CONHCONHCH₃ | |
| 668 | —CH₂—CH₂—CH₂—CH(CH₃)— | sec-butyl | Cl | CONHSO₂CF₃ | |
| 669 | —CH₂—CH₂—CH₂—CH(CH₃)— | sec-butyl | Cl | CONHSO₂CH₃ | |
| 670 | —CH₂—CH₂—CH₂—CH(CH₃)— | sec-butyl | Cl | CONHSO₂CH₂CH₃ | |
| 671 | —CH₂—CH₂—CH₂—CH(CH₃)— | sec-butyl | Cl | (isoxazol-3-ylamino)carbonyl | |
| 672 | —CH₂—CH₂—CH₂—CH(CH₃)— | sec-butyl | Cl | [(4-methyl-4H-1,2,4-triazol-3-yl)amino]carbonyl | |
| 673 | —CH₂—CH₂—O—CH₂—CH₂— | 2-chloro-6-fluorophenyl | Cl | CONHCONHCH₃ | |
| 674 | —CH₂—CH₂—O—CH₂—CH₂— | 2-chloro-6-fluorophenyl | Cl | CONHSO₂CF₃ | |
| 675 | —CH₂—CH₂—O—CH₂—CH₂— | 2-chloro-6-fluorophenyl | Cl | CONHSO₂CH₃ | |
| 676 | —CH₂—CH₂—O—CH₂—CH₂— | 2-chloro-6-fluorophenyl | Cl | CONHSO₂CH₂CH₃ | |

TABLE 1-continued

| Ex. No. | R$^1$ or —R$^{1+}$R$^2$— | R$^2$ R3 | X | R4 | log p |
|---|---|---|---|---|---|
| 677 | —CH$_2$—CH$_2$—O—CH$_2$—CH$_2$— | 2-chloro-6-fluorophenyl | Cl | (isoxazol-3-ylamino)carbonyl | |
| 678 | —CH$_2$—CH$_2$—O—CH$_2$—CH$_2$— | 2-chloro-6-fluorophenyl | Cl | [(4-methyl-4H-1,2,4-triazol-3-yl)amino]carbonyl | |
| 679 | —CH$_2$—CH$_2$—O—CH$_2$—CH$_2$— | 2,4,6-trifluorophenyl | Cl | CONHCONHCH$_3$ | |
| 680 | —CH$_2$—CH$_2$—O—CH$_2$—CH$_2$— | 2,4,6-trifluorophenyl | Cl | CONHSO$_2$CF$_3$ | |
| 681 | —CH$_2$—CH$_2$—O—CH$_2$—CH$_2$— | 2,4,6-trifluorophenyl | Cl | CONHSO$_2$CH$_3$ | |
| 682 | —CH$_2$—CH$_2$—O—CH$_2$—CH$_2$— | 2,4,6-trifluorophenyl | Cl | CONHSO$_2$CH$_2$CH$_3$ | |
| 683 | —CH$_2$—CH$_2$—O—CH$_2$—CH$_2$— | 2,4,6-trifluorophenyl | Cl | (isoxazol-3-ylamino)carbonyl | |
| 684 | —CH$_2$—CH$_2$—O—CH$_2$—CH$_2$— | 2,4,6-trifluorophenyl | Cl | [(4-methyl-4H-1,2,4-triazol-3-yl)amino]carbonyl | |
| 685 | —CH$_2$—CH$_2$—O—CH$_2$—CH$_2$— | 2-chloro-4-fluorophenyl | Cl | CONHCONHCH$_3$ | |
| 686 | —CH$_2$—CH$_2$—O—CH$_2$—CH$_2$— | 2-chloro-4-fluorophenyl | Cl | CONHSO$_2$CF$_3$ | |
| 687 | —CH$_2$—CH$_2$—O—CH$_2$—CH$_2$— | 2-chloro-4-fluorophenyl | Cl | CONHSO$_2$CH$_3$ | |
| 688 | —CH$_2$—CH$_2$—O—CH$_2$—CH$_2$— | 2-chloro-4-fluorophenyl | Cl | CONHSO$_2$CH$_2$CH$_3$ | |
| 689 | —CH$_2$—CH$_2$—O—CH$_2$—CH$_2$— | 2-chloro-4-fluorophenyl | Cl | (isoxazol-3-ylamino)carbonyl | |
| 690 | —CH$_2$—CH$_2$—O—CH$_2$—CH$_2$— | 2-chloro-4-fluorophenyl | Cl | [(4-methyl-4H-1,2,4-triazol-3-yl)amino]carbonyl | |
| 691 | —CH$_2$—CH$_2$—O—CH$_2$—CH$_2$— | 2-chlorophenyl | Cl | CONHCONHCH$_3$ | |
| 692 | —CH$_2$—CH$_2$—O—CH$_2$—CH$_2$— | 2-chlorophenyl | Cl | CONHSO$_2$CF$_3$ | |
| 693 | —CH$_2$—CH$_2$—O—CH$_2$—CH$_2$— | 2-chlorophenyl | Cl | CONHSO$_2$CH$_3$ | |
| 694 | —CH$_2$—CH$_2$—O—CH$_2$—CH$_2$— | 2-chlorophenyl | Cl | CONHSO$_2$CH$_2$CH$_3$ | |
| 695 | —CH$_2$—CH$_2$—O—CH$_2$—CH$_2$— | 2-chlorophenyl | Cl | (isoxazol-3-ylamino)carbonyl | |
| 696 | —CH$_2$—CH$_2$—O—CH$_2$—CH$_2$— | 2-chlorophenyl | Cl | [(4-methyl-4H-1,2,4-triazol-3-yl)amino]carbonyl | |
| 697 | —CH$_2$—CH$_2$—O—CH$_2$—CH$_2$— | 5-Cl-pyrimidin-4-yl | Cl | CONHCONHCH$_3$ | |
| 698 | —CH$_2$—CH$_2$—O—CH$_2$—CH$_2$— | 5-Cl-pyrimidin-4-yl | Cl | CONHSO$_2$CF$_3$ | |
| 699 | —CH$_2$—CH$_2$—O—CH$_2$—CH$_2$— | 5-Cl-pyrimidin-4-yl | Cl | CONHSO$_2$CH$_3$ | |
| 700 | —CH$_2$—CH$_2$—O—CH$_2$—CH$_2$— | 5-Cl-pyrimidin-4-yl | Cl | CONHSO$_2$CH$_2$CH$_3$ | |
| 701 | —CH$_2$—CH$_2$—O—CH$_2$—CH$_2$— | 5-Cl-pyrimidin-4-yl | Cl | (isoxazol-3-ylamino)carbonyl | |
| 702 | —CH$_2$—CH$_2$—O—CH$_2$—CH$_2$— | 5-Cl-pyrimidin-4-yl | Cl | [(4-methyl-4H-1,2,4-triazol-3-yl)amino]carbonyl | |
| 703 | —CH$_2$—CH$_2$—O—CH$_2$—CH$_2$— | 2-chloro-4,6-difluorophenyl | Cl | CONHCONHCH$_3$ | |
| 704 | —CH$_2$—CH$_2$—O—CH$_2$—CH$_2$— | 2-chloro-4,6-difluorophenyl | Cl | CONHSO$_2$CF$_3$ | |
| 705 | —CH$_2$—CH$_2$—O—CH$_2$—CH$_2$— | 2-chloro-4,6-difluorophenyl | Cl | CONHSO$_2$CH$_3$ | |
| 706 | —CH$_2$—CH$_2$—O—CH$_2$—CH$_2$— | 2-chloro-4,6-difluorophenyl | Cl | CONHSO$_2$CH$_2$CH$_3$ | |
| 707 | —CH$_2$—CH$_2$—O—CH$_2$—CH$_2$— | 2-chloro-4,6-difluorophenyl | Cl | (isoxazol-3-ylamino)carbonyl | |
| 708 | —CH$_2$—CH$_2$—O—CH$_2$—CH$_2$— | 2-chloro-4,6-difluorophenyl | Cl | [(4-methyl-4H-1,2,4-triazol-3-yl)amino]carbonyl | |
| 709 | —CH$_2$—CH$_2$—O—CH$_2$—CH$_2$— | 2,4-dichlorophenyl | Cl | CONHCONHCH$_3$ | |
| 710 | —CH$_2$—CH$_2$—O—CH$_2$—CH$_2$— | 2,4-dichlorophenyl | Cl | CONHSO$_2$CF$_3$ | |
| 711 | —CH$_2$—CH$_2$—O—CH$_2$—CH$_2$— | 2,4-dichlorophenyl | Cl | CONHSO$_2$CH$_3$ | |
| 712 | —CH$_2$—CH$_2$—O—CH$_2$—CH$_2$— | 2,4-dichlorophenyl | Cl | CONHSO$_2$CH$_2$CH$_3$ | |
| 713 | —CH$_2$—CH$_2$—O—CH$_2$—CH$_2$— | 2,4-dichlorophenyl | Cl | (isoxazol-3-ylamino)carbonyl | |
| 714 | —CH$_2$—CH$_2$—O—CH$_2$—CH$_2$— | 2,4-dichlorophenyl | Cl | [(4-methyl-4H-1,2,4-triazol-3-yl)amino]carbonyl | |
| 715 | —CH$_2$—CH$_2$—O—CH$_2$—CH$_2$— | 4-chloro-2,6-difluorophenyl | Cl | CONHCONHCH$_3$ | |
| 716 | —CH$_2$—CH$_2$—O—CH$_2$—CH$_2$— | 4-chloro-2,6-difluorophenyl | Cl | CONHSO$_2$CF$_3$ | |
| 717 | —CH$_2$—CH$_2$—O—CH$_2$—CH$_2$— | 4-chloro-2,6-difluorophenyl | Cl | CONHSO$_2$CH$_3$ | |
| 718 | —CH$_2$—CH$_2$—O—CH$_2$—CH$_2$— | 4-chloro-2,6-difluorophenyl | Cl | CONHSO$_2$CH$_2$CH$_3$ | |
| 719 | —CH$_2$—CH$_2$—O—CH$_2$—CH$_2$— | 4-chloro-2,6-difluorophenyl | Cl | (isoxazol-3-ylamino)carbonyl | |
| 720 | —CH$_2$—CH$_2$—O—CH$_2$—CH$_2$— | 4-chloro-2,6-difluorophenyl | Cl | [(4-methyl-4H-1,2,4-triazol-3-yl)amino]carbonyl | |
| 721 | —CH$_2$—CH$_2$—O—CH$_2$—CH$_2$— | 2,6-difluoro-4-methylphenyl | Cl | CONHCONHCH$_3$ | |

TABLE 1-continued

| Ex. No. | R¹ or —R¹⁺R²— | R3 | X | R4 | log p |
|---|---|---|---|---|---|
| 722 | —CH₂—CH₂—O—CH₂—CH₂— | 2,6-difluoro-4-methylphenyl | Cl | CONHSO₂CF₃ | |
| 723 | —CH₂—CH₂—O—CH₂—CH₂— | 2,6-difluoro-4-methylphenyl | Cl | CONHSO₂CH₃ | |
| 724 | —CH₂—CH₂—O—CH₂—CH₂— | 2,6-difluoro-4-methylphenyl | Cl | CONHSO₂CH₂CH₃ | |
| 725 | —CH₂—CH₂—O—CH₂—CH₂— | 2,6-difluoro-4-methylphenyl | Cl | (isoxazol-3-ylamino)carbonyl | |
| 726 | —CH₂—CH₂—O—CH₂—CH₂— | 2,6-difluoro-4-methylphenyl | Cl | [(4-methyl-4H-1,2,4-triazol-3-yl)amino]carbonyl | |
| 727 | —CH₂—CH₂—O—CH₂—CH₂— | 2-chloro-5-fluorophenyl | Cl | CONHCONHCH₃ | |
| 728 | —CH₂—CH₂—O—CH₂—CH₂— | 2-chloro-5-fluorophenyl | Cl | CONHSO₂CF₃ | |
| 729 | —CH₂—CH₂—O—CH₂—CH₂— | 2-chloro-5-fluorophenyl | Cl | CONHSO₂CH₃ | |
| 730 | —CH₂—CH₂—O—CH₂—CH₂— | 2-chloro-5-fluorophenyl | Cl | CONHSO₂CH₂CH₃ | |
| 731 | —CH₂—CH₂—O—CH₂—CH₂— | 2-chloro-5-fluorophenyl | Cl | (isoxazol-3-ylamino)carbonyl | |
| 732 | —CH₂—CH₂—O—CH₂—CH₂— | 2-chloro-5-fluorophenyl | Cl | [(4-methyl-4H-1,2,4-triazol-3-yl)amino]carbonyl | |
| 733 | —CH₂—CH₂—O—CH₂—CH₂— | 3-chloro-2-thienyl | Cl | CONHCONHCH₃ | |
| 734 | —CH₂—CH₂—O—CH₂—CH₂— | 3-chloro-2-thienyl | Cl | CONHSO₂CF₃ | |
| 735 | —CH₂—CH₂—O—CH₂—CH₂— | 3-chloro-2-thienyl | Cl | CONHSO₂CH₃ | |
| 736 | —CH₂—CH₂—O—CH₂—CH₂— | 3-chloro-2-thienyl | Cl | CONHSO₂CH₂CH₃ | |
| 737 | —CH₂—CH₂—O—CH₂—CH₂— | 3-chloro-2-thienyl | Cl | (isoxazol-3-ylamino)carbonyl | |
| 738 | —CH₂—CH₂—O—CH₂—CH₂— | 3-chloro-2-thienyl | Cl | [(4-methyl-4H-1,2,4-triazol-3-yl)amino]carbonyl | |
| 739 | —CH₂—CH₂—O—CH₂—CH₂— | phenyl | Cl | CONHCONHCH₃ | |
| 740 | —CH₂—CH₂—O—CH₂—CH₂— | phenyl | Cl | CONHSO₂CF₃ | |
| 741 | —CH₂—CH₂—O—CH₂—CH₂— | phenyl | Cl | CONHSO₂CH₃ | |
| 742 | —CH₂—CH₂—O—CH₂—CH₂— | phenyl | Cl | CONHSO₂CH₂CH₃ | |
| 743 | —CH₂—CH₂—O—CH₂—CH₂— | phenyl | Cl | (isoxazol-3-ylamino)carbonyl | |
| 744 | —CH₂—CH₂—O—CH₂—CH₂— | phenyl | Cl | [(4-methyl-4H-1,2,4-triazol-3-yl)amino]carbonyl | |
| 745 | —CH₂—CH₂—O—CH₂—CH₂— | cyclopentyl | Cl | CONHCONHCH₃ | |
| 746 | —CH₂—CH₂—O—CH₂—CH₂— | cyclopentyl | Cl | CONHSO₂CF₃ | |
| 747 | —CH₂—CH₂—O—CH₂—CH₂— | cyclopentyl | Cl | CONHSO₂CH₃ | |
| 748 | —CH₂—CH₂—O—CH₂—CH₂— | cyclopentyl | Cl | CONHSO₂CH₂CH₃ | |
| 749 | —CH₂—CH₂—O—CH₂—CH₂— | cyclopentyl | Cl | (isoxazol-3-ylamino)carbonyl | |
| 750 | —CH₂—CH₂—O—CH₂—CH₂— | cyclopentyl | Cl | [(4-methyl-4H-1,2,4-triazol-3-yl)amino]carbonyl | |
| 751 | —CH₂—CH₂—O—CH₂—CH₂— | sec-butyl | Cl | CONHCONHCH₃ | |
| 752 | —CH₂—CH₂—O—CH₂—CH₂— | sec-butyl | Cl | CONHSO₂CF₃ | |
| 753 | —CH₂—CH₂—O—CH₂—CH₂— | sec-butyl | Cl | CONHSO₂CH₃ | |
| 754 | —CH₂—CH₂—O—CH₂—CH₂— | sec-butyl | Cl | CONHSO₂CH₂CH₃ | |
| 755 | —CH₂—CH₂—O—CH₂—CH₂— | sec-butyl | Cl | (isoxazol-3-ylamino)carbonyl | |
| 756 | —CH₂—CH₂—O—CH₂—CH₂— | sec-butyl | Cl | [(4-methyl-4H-1,2,4-triazol-3-yl)amino]carbonyl | |
| 757 | —CH₂—CH₂—CH₂—CH₂—NH— | 2-chloro-6-fluorophenyl | Cl | CONHCONHCH₃ | |
| 758 | —CH₂—CH₂—CH₂—CH₂—NH— | 2-chloro-6-fluorophenyl | Cl | CONHSO₂CF₃ | |
| 759 | —CH₂—CH₂—CH₂—CH₂—NH— | 2-chloro-6-fluorophenyl | Cl | CONHSO₂CH₃ | |
| 760 | —CH₂—CH₂—CH₂—CH₂—NH— | 2-chloro-6-fluorophenyl | Cl | CONHSO₂CH₂CH₃ | |
| 761 | —CH₂—CH₂—CH₂—CH₂—NH— | 2-chloro-6-fluorophenyl | Cl | (isoxazol-3-ylamino)carbonyl | |
| 762 | —CH₂—CH₂—CH₂—CH₂—NH— | 2-chloro-6-fluorophenyl | Cl | [(4-methyl-4H-1,2,4-triazol-3-yl)amino]carbonyl | |
| 763 | —CH₂—CH₂—CH₂—CH₂—NH— | 2,4,6-trifluorophenyl | Cl | CONHCONHCH₃ | |
| 764 | —CH₂—CH₂—CH₂—CH₂—NH— | 2,4,6-trifluorophenyl | Cl | CONHSO₂CF₃ | |
| 765 | —CH₂—CH₂—CH₂—CH₂—NH— | 2,4,6-trifluorophenyl | Cl | CONHSO₂CH₃ | |
| 766 | —CH₂—CH₂—CH₂—CH₂—NH— | 2,4,6-trifluorophenyl | Cl | CONHSO₂CH₂CH₃ | |
| 767 | —CH₂—CH₂—CH₂—CH₂—NH— | 2,4,6-trifluorophenyl | Cl | (isoxazol-3-ylamino)carbonyl | |
| 768 | —CH₂—CH₂—CH₂—CH₂—NH— | 2,4,6-trifluorophenyl | Cl | [(4-methyl-4H-1,2,4-triazol-3-yl)amino]carbonyl | |
| 769 | —CH₂—CH₂—CH₂—CH₂—NH— | 2-chloro-4-fluorophenyl | Cl | CONHCONHCH₃ | |
| 770 | —CH₂—CH₂—CH₂—CH₂—NH— | 2-chloro-4-fluorophenyl | Cl | CONHSO₂CF₃ | |
| 771 | —CH₂—CH₂—CH₂—CH₂—NH— | 2-chloro-4-fluorophenyl | Cl | CONHSO₂CH₃ | |
| 772 | —CH₂—CH₂—CH₂—CH₂—NH— | 2-chloro-4-fluorophenyl | Cl | CONHSO₂CH₂CH₃ | |
| 773 | —CH₂—CH₂—CH₂—CH₂—NH— | 2-chloro-4-fluorophenyl | Cl | (isoxazol-3-ylamino)carbonyl | |

TABLE 1-continued

| Ex. No. | R$^1$ or —R$^{1+}$R$^2$— | R3 | X | R4 | log p |
|---|---|---|---|---|---|
| 774 | —CH$_2$—CH$_2$—CH$_2$—CH$_2$—NH— | 2-chloro-4-fluorophenyl | Cl | [(4-methyl-4H-1,2,4-triazol-3-yl)amino]carbonyl | |
| 775 | —CH$_2$—CH$_2$—CH$_2$—CH$_2$—NH— | 2-chlorophenyl | Cl | CONHCONHCH$_3$ | |
| 776 | —CH$_2$—CH$_2$—CH$_2$—CH$_2$—NH— | 2-chlorophenyl | Cl | CONHSO$_2$CF$_3$ | |
| 777 | —CH$_2$—CH$_2$—CH$_2$—CH$_2$—NH— | 2-chlorophenyl | Cl | CONHSO$_2$CH$_3$ | |
| 778 | —CH$_2$—CH$_2$—CH$_2$—CH$_2$—NH— | 2-chlorophenyl | Cl | CONHSO$_2$CH$_2$CH$_3$ | |
| 779 | —CH$_2$—CH$_2$—CH$_2$—CH$_2$—NH— | 2-chlorophenyl | Cl | (isoxazol-3-ylamino)carbonyl | |
| 780 | —CH$_2$—CH$_2$—CH$_2$—CH$_2$—NH— | 2-chlorophenyl | Cl | [(4-methyl-4H-1,2,4-triazol-3-yl)amino]carbonyl | |
| 781 | —CH$_2$—CH$_2$—CH$_2$—CH$_2$—NH— | 5-Cl-pyrimidin-4-yl | Cl | CONHCONHCH$_3$ | |
| 782 | —CH$_2$—CH$_2$—CH$_2$—CH$_2$—NH— | 5-Cl-pyrimidin-4-yl | Cl | CONHSO$_2$CF$_3$ | |
| 783 | —CH$_2$—CH$_2$—CH$_2$—CH$_2$—NH— | 5-Cl-pyrimidin-4-yl | Cl | CONHSO$_2$CH$_3$ | |
| 784 | —CH$_2$—CH$_2$—CH$_2$—CH$_2$—NH— | 5-Cl-pyrimidin-4-yl | Cl | CONHSO$_2$CH$_2$CH$_3$ | |
| 785 | —CH$_2$—CH$_2$—CH$_2$—CH$_2$—NH— | 5-Cl-pyrimidin-4-yl | Cl | (isoxazol-3-ylamino)carbonyl | |
| 786 | —CH$_2$—CH$_2$—CH$_2$—CH$_2$—NH— | 5-Cl-pyrimidin-4-yl | Cl | [(4-methyl-4H-1,2,4-triazol-3-yl)amino]carbonyl | |
| 787 | —CH$_2$—CH$_2$—CH$_2$—CH$_2$—NH— | 2-chloro-4,6-difluorophenyl | Cl | CONHCONHCH$_3$ | |
| 788 | —CH$_2$—CH$_2$—CH$_2$—CH$_2$—NH— | 2-chloro-4,6-difluorophenyl | Cl | CONHSO$_2$CF$_3$ | |
| 789 | —CH$_2$—CH$_2$—CH$_2$—CH$_2$—NH— | 2-chloro-4,6-difluorophenyl | Cl | CONHSO$_2$CH$_3$ | |
| 790 | —CH$_2$—CH$_2$—CH$_2$—CH$_2$—NH— | 2-chloro-4,6-difluorophenyl | Cl | CONHSO$_2$CH$_2$CH$_3$ | |
| 791 | —CH$_2$—CH$_2$—CH$_2$—CH$_2$—NH— | 2-chloro-4,6-difluorophenyl | Cl | (isoxazol-3-ylamino)carbonyl | |
| 792 | —CH$_2$—CH$_2$—CH$_2$—CH$_2$—NH— | 2-chloro-4,6-difluorophenyl | Cl | [(4-methyl-4H-1,2,4-triazol-3-yl)amino]carbonyl | |
| 793 | —CH$_2$—CH$_2$—CH$_2$—CH$_2$—NH— | 2,4-dichlorophenyl | Cl | CONHCONHCH$_3$ | |
| 794 | —CH$_2$—CH$_2$—CH$_2$—CH$_2$—NH— | 2,4-dichlorophenyl | Cl | CONHSO$_2$CF$_3$ | |
| 795 | —CH$_2$—CH$_2$—CH$_2$—CH$_2$—NH— | 2,4-dichlorophenyl | Cl | CONHSO$_2$CH$_3$ | |
| 796 | —CH$_2$—CH$_2$—CH$_2$—CH$_2$—NH— | 2,4-dichlorophenyl | Cl | CONHSO$_2$CH$_2$CH$_3$ | |
| 797 | —CH$_2$—CH$_2$—CH$_2$—CH$_2$—NH— | 2,4-dichlorophenyl | Cl | (isoxazol-3-ylamino)carbonyl | |
| 798 | —CH$_2$—CH$_2$—CH$_2$—CH$_2$—NH— | 2,4-dichlorophenyl | Cl | [(4-methyl-4H-1,2,4-triazol-3-yl)amino]carbonyl | |
| 799 | —CH$_2$—CH$_2$—CH$_2$—CH$_2$—NH— | 4-chloro-2,6-difluorophenyl | Cl | CONHCONHCH$_3$ | |
| 800 | —CH$_2$—CH$_2$—CH$_2$—CH$_2$—NH— | 4-chloro-2,6-difluorophenyl | Cl | CONHSO$_2$CF$_3$ | |
| 801 | —CH$_2$—CH$_2$—CH$_2$—CH$_2$—NH— | 4-chloro-2,6-difluorophenyl | Cl | CONHSO$_2$CH$_3$ | |
| 802 | —CH$_2$—CH$_2$—CH$_2$—CH$_2$—NH— | 4-chloro-2,6-difluorophenyl | Cl | CONHSO$_2$CH$_2$CH$_3$ | |
| 803 | —CH$_2$—CH$_2$—CH$_2$—CH$_2$—NH— | 4-chloro-2,6-difluorophenyl | Cl | (isoxazol-3-ylamino)carbonyl | |
| 804 | —CH$_2$—CH$_2$—CH$_2$—CH$_2$—NH— | 4-chloro-2,6-difluorophenyl | Cl | [(4-methyl-4H-1,2,4-triazol-3-yl)amino]carbonyl | |
| 805 | —CH$_2$—CH$_2$—CH$_2$—CH$_2$—NH— | 2,6-difluoro-4-methylphenyl | Cl | CONHCONHCH$_3$ | |
| 806 | —CH$_2$—CH$_2$—CH$_2$—CH$_2$—NH— | 2,6-difluoro-4-methylphenyl | Cl | CONHSO$_2$CF$_3$ | |
| 807 | —CH$_2$—CH$_2$—CH$_2$—CH$_2$—NH— | 2,6-difluoro-4-methylphenyl | Cl | CONHSO$_2$CH$_3$ | |
| 808 | —CH$_2$—CH$_2$—CH$_2$—CH$_2$—NH— | 2,6-difluoro-4-methylphenyl | Cl | CONHSO$_2$CH$_2$CH$_3$ | |
| 809 | —CH$_2$—CH$_2$—CH$_2$—CH$_2$—NH— | 2,6-difluoro-4-methylphenyl | Cl | (isoxazol-3-ylamino)carbonyl | |
| 810 | —CH$_2$—CH$_2$—CH$_2$—CH$_2$—NH— | 2,6-difluoro-4-methylphenyl | Cl | [(4-methyl-4H-1,2,4-triazol-3-yl)amino]carbonyl | |
| 811 | —CH$_2$—CH$_2$—CH$_2$—CH$_2$—NH— | 2-chloro-5-fluorophenyl | Cl | CONHCONHCH$_3$ | |
| 812 | —CH$_2$—CH$_2$—CH$_2$—CH$_2$—NH— | 2-chloro-5-fluorophenyl | Cl | CONHSO$_2$CF$_3$ | |
| 813 | —CH$_2$—CH$_2$—CH$_2$—CH$_2$—NH— | 2-chloro-5-fluorophenyl | Cl | CONHSO$_2$CH$_3$ | |
| 814 | —CH$_2$—CH$_2$—CH$_2$—CH$_2$—NH— | 2-chloro-5-fluorophenyl | Cl | CONHSO$_2$CH$_2$CH$_3$ | |
| 815 | —CH$_2$—CH$_2$—CH$_2$—CH$_2$—NH— | 2-chloro-5-fluorophenyl | Cl | (isoxazol-3-ylamino)carbonyl | |

TABLE 1-continued

| Ex. No. | R¹ or —R¹⁺R²— | R² | R3 | X | R4 |
|---|---|---|---|---|---|
| 816 | —CH₂—CH₂—CH₂—CH₂—NH— | | 2-chloro-5-fluorophenyl | Cl | [(4-methyl-4H-1,2,4-triazol-3-yl)amino]carbonyl |
| 817 | —CH₂—CH₂—CH₂—CH₂—NH— | | 3-chloro-2-thienyl | Cl | CONHCONHCH₃ |
| 818 | —CH₂—CH₂—CH₂—CH₂—NH— | | 3-chloro-2-thienyl | Cl | CONHSO₂CF₃ |
| 819 | —CH₂—CH₂—CH₂—CH₂—NH— | | 3-chloro-2-thienyl | Cl | CONHSO₂CH₃ |
| 820 | —CH₂—CH₂—CH₂—CH₂—NH— | | 3-chloro-2-thienyl | Cl | CONHSO₂CH₂CH₃ |
| 821 | —CH₂—CH₂—CH₂—CH₂—NH— | | 3-chloro-2-thienyl | Cl | (isoxazol-3-ylamino)carbonyl |
| 822 | —CH₂—CH₂—CH₂—CH₂—NH— | | 3-chloro-2-thienyl | Cl | [(4-methyl-4H-1,2,4-triazol-3-yl)amino]carbonyl |
| 823 | —CH₂—CH₂—CH₂—CH₂—NH— | | phenyl | Cl | CONHCONHCH₃ |
| 824 | —CH₂—CH₂—CH₂—CH₂—NH— | | phenyl | Cl | CONHSO₂CF₃ |
| 825 | —CH₂—CH₂—CH₂—CH₂—NH— | | phenyl | Cl | CONHSO₂CH₃ |
| 826 | —CH₂—CH₂—CH₂—CH₂—NH— | | phenyl | Cl | CONHSO₂CH₂CH₃ |
| 827 | —CH₂—CH₂—CH₂—CH₂—NH— | | phenyl | Cl | (isoxazol-3-ylamino)carbonyl |
| 828 | —CH₂—CH₂—CH₂—CH₂—NH— | | phenyl | Cl | [(4-methyl-4H-1,2,4-triazol-3-yl)amino]carbonyl |
| 829 | —CH₂—CH₂—CH₂—CH₂—NH— | | cyclopentyl | Cl | CONHCONHCH₃ |
| 830 | —CH₂—CH₂—CH₂—CH₂—NH— | | cyclopentyl | Cl | CONHSO₂CF₃ |
| 831 | —CH₂—CH₂—CH₂—CH₂—NH— | | cyclopentyl | Cl | CONHSO₂CH₃ |
| 832 | —CH₂—CH₂—CH₂—CH₂—NH— | | cyclopentyl | Cl | CONHSO₂CH₂CH₃ |
| 833 | —CH₂—CH₂—CH₂—CH₂—NH— | | cyclopentyl | Cl | (isoxazol-3-ylamino)carbonyl |
| 834 | —CH₂—CH₂—CH₂—CH₂—NH— | | cyclopentyl | Cl | [(4-methyl-4H-1,2,4-triazol-3-yl)amino]carbonyl |
| 835 | —CH₂—CH₂—CH₂—CH₂—NH— | | sec-butyl | Cl | CONHCONHCH₃ |
| 836 | —CH₂—CH₂—CH₂—CH₂—NH— | | sec-butyl | Cl | CONHSO₂CF₃ |
| 837 | —CH₂—CH₂—CH₂—CH₂—NH— | | sec-butyl | Cl | CONHSO₂CH₃ |
| 838 | —CH₂—CH₂—CH₂—CH₂—NH— | | sec-butyl | Cl | CONHSO₂CH₂CH₃ |
| 839 | —CH₂—CH₂—CH₂—CH₂—NH— | | sec-butyl | Cl | (isoxazol-3-ylamino)carbonyl |
| 840 | —CH₂—CH₂—CH₂—CH₂—NH— | | sec-butyl | Cl | [(4-methyl-4H-1,2,4-triazol-3-yl)amino]carbonyl |
| 841 | —CH₂—CH₂—CH₂—CH₂—NH— | | 2-methyl-cyclopentyl | Cl | CONHSO₂CH₃ |
| 842 | CH(CH₃)—C(CH₃)₃ | H | 2-chloro-6-fluorophenyl | CH₃ | CONHCONHCH₃ |
| 843 | CH(CH₃)—C(CH₃)₃ | H | 2-chloro-6-fluorophenyl | CH₃ | CONHSO₂CF₃ |
| 844 | CH(CH₃)—C(CH₃)₃ | H | 2-chloro-6-fluorophenyl | CH₃ | CONHSO₂CH₃ |
| 845 | CH(CH₃)—C(CH₃)₃ | H | 2-chloro-6-fluorophenyl | CH₃ | CONHSO₂CH₂CH₃ |
| 846 | CH(CH₃)—C(CH₃)₃ | H | 2-chloro-6-fluorophenyl | CH₃ | (isoxazol-3-ylamino)carbonyl |
| 847 | CH(CH₃)—C(CH₃)₃ | H | 2-chloro-6-fluorophenyl | CH₃ | [(4-methyl-4H-1,2,4-triazol-3-yl)amino]carbonyl |
| 848 | CH(CH₃)—C(CH₃)₃ | H | 2,4,6-trifluorophenyl | CH₃ | CONHCONHCH₃ |
| 849 | CH(CH₃)—C(CH₃)₃ | H | 2,4,6-trifluorophenyl | CH₃ | CONHSO₂CF₃ |
| 850 | CH(CH₃)—C(CH₃)₃ | H | 2,4,6-trifluorophenyl | CH₃ | CONHSO₂CH₃ |
| 851 | CH(CH₃)—C(CH₃)₃ | H | 2,4,6-trifluorophenyl | CH₃ | CONHSO₂CH₂CH₃ |
| 852 | CH(CH₃)—C(CH₃)₃ | H | 2,4,6-trifluorophenyl | CH₃ | (isoxazol-3-ylamino)carbonyl |
| 853 | CH(CH₃)—C(CH₃)₃ | H | 2,4,6-trifluorophenyl | CH₃ | [(4-methyl-4H-1,2,4-triazol-3-yl)amino]carbonyl |
| 854 | CH(CH₃)—C(CH₃)₃ | H | 2-chloro-4-fluorophenyl | CH₃ | CONHCONHCH₃ |
| 855 | CH(CH₃)—C(CH₃)₃ | H | 2-chloro-4-fluorophenyl | CH₃ | CONHSO₂CF₃ |
| 856 | CH(CH₃)—C(CH₃)₃ | H | 2-chloro-4-fluorophenyl | CH₃ | CONHSO₂CH₃ |
| 857 | CH(CH₃)—C(CH₃)₃ | H | 2-chloro-4-fluorophenyl | CH₃ | CONHSO₂CH₂CH₃ |
| 858 | CH(CH₃)—C(CH₃)₃ | H | 2-chloro-4-fluorophenyl | CH₃ | (isoxazol-3-ylamino)carbonyl |
| 859 | CH(CH₃)—C(CH₃)₃ | H | 2-chloro-4-fluorophenyl | CH₃ | [(4-methyl-4H-1,2,4-triazol-3-yl)amino]carbonyl |
| 860 | CH(CH₃)—C(CH₃)₃ | H | 2-chlorophenyl | CH₃ | CONHCONHCH₃ |
| 861 | CH(CH₃)—C(CH₃)₃ | H | 2-chlorophenyl | CH₃ | CONHSO₂CF₃ |
| 862 | CH(CH₃)—C(CH₃)₃ | H | 2-chlorophenyl | CH₃ | CONHSO₂CH₃ |
| 863 | CH(CH₃)—C(CH₃)₃ | H | 2-chlorophenyl | CH₃ | CONHSO₂CH₂CH₃ |
| 864 | CH(CH₃)—C(CH₃)₃ | H | 2-chlorophenyl | CH₃ | (isoxazol-3-ylamino)carbonyl |
| 865 | CH(CH₃)—C(CH₃)₃ | H | 2-chlorophenyl | CH₃ | [(4-methyl-4H-1,2,4-triazol-3-yl)amino]carbonyl |
| 866 | CH(CH₃)—C(CH₃)₃ | H | 5-Cl-pyrimidin-4-yl | CH₃ | CONHCONHCH₃ |
| 867 | CH(CH₃)—C(CH₃)₃ | H | 5-Cl-pyrimidin-4-yl | CH₃ | CONHSO₂CF₃ |
| 868 | CH(CH₃)—C(CH₃)₃ | H | 5-Cl-pyrimidin-4-yl | CH₃ | CONHSO₂CH₃ |
| 869 | CH(CH₃)—C(CH₃)₃ | H | 5-Cl-pyrimidin-4-yl | CH₃ | CONHSO₂CH₂CH₃ |
| 870 | CH(CH₃)—C(CH₃)₃ | H | 5-Cl-pyrimidin-4-yl | CH₃ | (isoxazol-3-ylamino)carbonyl |

TABLE 1-continued

Structure: pyrazolo[1,5-a]pyrimidine with NR¹R² at 7-position, R³ at 6, X at 5, R⁴ at 3.

| Ex. No. | R¹ or —R¹⁺R²— | R² | R3 | X | R4 | log p |
|---|---|---|---|---|---|---|
| 871 | CH(CH₃)—C(CH₃)₃ | H | 5-Cl-pyrimidin-4-yl | CH₃ | [(4-methyl-4H-1,2,4-triazol-3-yl)amino]carbonyl | |
| 872 | CH(CH₃)—C(CH₃)₃ | H | 2-chloro-4,6-difluorophenyl | CH₃ | CONHCONHCH₃ | |
| 873 | CH(CH₃)—C(CH₃)₃ | H | 2-chloro-4,6-difluorophenyl | CH₃ | CONHSO₂CF₃ | |
| 874 | CH(CH₃)—C(CH₃)₃ | H | 2-chloro-4,6-difluorophenyl | CH₃ | CONHSO₂CH₃ | |
| 875 | CH(CH₃)—C(CH₃)₃ | H | 2-chloro-4,6-difluorophenyl | CH₃ | CONHSO₂CH₂CH₃ | |
| 876 | CH(CH₃)—C(CH₃)₃ | H | 2-chloro-4,6-difluorophenyl | CH₃ | (isoxazol-3-ylamino)carbonyl | |
| 877 | CH(CH₃)—C(CH₃)₃ | H | 2-chloro-4,6-difluorophenyl | CH₃ | [(4-methyl-4H-1,2,4-triazol-3-yl)amino]carbonyl | |
| 878 | CH(CH₃)—C(CH₃)₃ | H | 2,4-dichlorophenyl | CH₃ | CONHCONHCH₃ | |
| 879 | CH(CH₃)—C(CH₃)₃ | H | 2,4-dichlorophenyl | CH₃ | CONHSO₂CF₃ | |
| 880 | CH(CH₃)—C(CH₃)₃ | H | 2,4-dichlorophenyl | CH₃ | CONHSO₂CH₃ | |
| 881 | CH(CH₃)—C(CH₃)₃ | H | 2,4-dichlorophenyl | CH₃ | CONHSO₂CH₂CH₃ | |
| 882 | CH(CH₃)—C(CH₃)₃ | H | 2,4-dichlorophenyl | CH₃ | (isoxazol-3-ylamino)carbonyl | |
| 883 | CH(CH₃)—C(CH₃)₃ | H | 2,4-dichlorophenyl | CH₃ | [(4-methyl-4H-1,2,4-triazol-3-yl)amino]carbonyl | |
| 884 | CH(CH₃)—C(CH₃)₃ | H | 4-chloro-2,6-difluorophenyl | CH₃ | CONHCONHCH₃ | |
| 885 | CH(CH₃)—C(CH₃)₃ | H | 4-chloro-2,6-difluorophenyl | CH₃ | CONHSO₂CF₃ | |
| 886 | CH(CH₃)—C(CH₃)₃ | H | 4-chloro-2,6-difluorophenyl | CH₃ | CONHSO₂CH₃ | |
| 887 | CH(CH₃)—C(CH₃)₃ | H | 4-chloro-2,6-difluorophenyl | CH₃ | CONHSO₂CH₂CH₃ | |
| 888 | CH(CH₃)—C(CH₃)₃ | H | 4-chloro-2,6-difluorophenyl | CH₃ | (isoxazol-3-ylamino)carbonyl | |
| 889 | CH(CH₃)—C(CH₃)₃ | H | 4-chloro-2,6-difluorophenyl | CH₃ | [(4-methyl-4H-1,2,4-triazol-3-yl)amino]carbonyl | |
| 890 | CH(CH₃)—C(CH₃)₃ | H | 2,6-difluoro-4-methylphenyl | CH₃ | CONHCONHCH₃ | |
| 891 | CH(CH₃)—C(CH₃)₃ | H | 2,6-difluoro-4-methylphenyl | CH₃ | CONHSO₂CF₃ | |
| 892 | CH(CH₃)—C(CH₃)₃ | H | 2,6-difluoro-4-methylphenyl | CH₃ | CONHSO₂CH₃ | |
| 893 | CH(CH₃)—C(CH₃)₃ | H | 2,6-difluoro-4-methylphenyl | CH₃ | CONHSO₂CH₂CH₃ | |
| 894 | CH(CH₃)—C(CH₃)₃ | H | 2,6-difluoro-4-methylphenyl | CH₃ | (isoxazol-3-ylamino)carbonyl | |
| 895 | CH(CH₃)—C(CH₃)₃ | H | 2,6-difluoro-4-methylphenyl | CH₃ | [(4-methyl-4H-1,2,4-triazol-3-yl)amino]carbonyl | |
| 896 | CH(CH₃)—C(CH₃)₃ | H | 2-chloro-5-fluorophenyl | CH₃ | CONHCONHCH₃ | |
| 897 | CH(CH₃)—C(CH₃)₃ | H | 2-chloro-5-fluorophenyl | CH₃ | CONHSO₂CF₃ | |
| 898 | CH(CH₃)—C(CH₃)₃ | H | 2-chloro-5-fluorophenyl | CH₃ | CONHSO₂CH₃ | |
| 899 | CH(CH₃)—C(CH₃)₃ | H | 2-chloro-5-fluorophenyl | CH₃ | CONHSO₂CH₂CH₃ | |
| 900 | CH(CH₃)—C(CH₃)₃ | H | 2-chloro-5-fluorophenyl | CH₃ | (isoxazol-3-ylamino)carbonyl | |
| 901 | CH(CH₃)—C(CH₃)₃ | H | 2-chloro-5-fluorophenyl | CH₃ | [(4-methyl-4H-1,2,4-triazol-3-yl)amino]carbonyl | |
| 902 | CH(CH₃)—C(CH₃)₃ | H | 3-chloro-2-thienyl | CH₃ | CONHCONHCH₃ | |
| 903 | CH(CH₃)—C(CH₃)₃ | H | 3-chloro-2-thienyl | CH₃ | CONHSO₂CF₃ | |
| 904 | CH(CH₃)—C(CH₃)₃ | H | 3-chloro-2-thienyl | CH₃ | CONHSO₂CH₃ | |
| 905 | CH(CH₃)—C(CH₃)₃ | H | 3-chloro-2-thienyl | CH₃ | CONHSO₂CH₂CH₃ | |
| 906 | CH(CH₃)—C(CH₃)₃ | H | 3-chloro-2-thienyl | CH₃ | (isoxazol-3-ylamino)carbonyl | |
| 907 | CH(CH₃)—C(CH₃)₃ | H | 3-chloro-2-thienyl | CH₃ | [(4-methyl-4H-1,2,4-triazol-3-yl)amino]carbonyl | |
| 908 | CH(CH₃)—C(CH₃)₃ | H | phenyl | CH₃ | CONHCONHCH₃ | |
| 909 | CH(CH₃)—C(CH₃)₃ | H | phenyl | CH₃ | CONHSO₂CF₃ | |
| 910 | CH(CH₃)—C(CH₃)₃ | H | phenyl | CH₃ | CONHSO₂CH₃ | |
| 911 | CH(CH₃)—C(CH₃)₃ | H | phenyl | CH₃ | CONHSO₂CH₂CH₃ | |
| 912 | CH(CH₃)—C(CH₃)₃ | H | phenyl | CH₃ | (isoxazol-3-ylamino)carbonyl | |

TABLE 1-continued

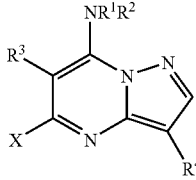

| Ex. No. | R$^1$ or —R$^{1+}$R$^2$— | R$^2$ | R3 | X | R4 | log p |
|---|---|---|---|---|---|---|
| 913 | CH(CH$_3$)—O(CH$_3$)$_3$ | H | phenyl | CH$_3$ | [(4-methyl-4H-1,2,4-triazol-3-yl)amino]carbonyl | |
| 914 | CH(CH$_3$)—C(CH$_3$)$_3$ | H | cyclopentyl | CH$_3$ | CONHCONHCH$_3$ | |
| 915 | CH(CH$_3$)—C(CH$_3$)$_3$ | H | cyclopentyl | CH$_3$ | CONHSO$_2$CF$_3$ | |
| 916 | CH(CH$_3$)—C(CH$_3$)$_3$ | H | cyclopentyl | CH$_3$ | CONHSO$_2$CH$_3$ | |
| 917 | CH(CH$_3$)—C(CH$_3$)$_3$ | H | cyclopentyl | CH$_3$ | CONHSO$_2$CH$_2$CH$_3$ | |
| 918 | CH(CH$_3$)—C(CH$_3$)$_3$ | H | cyclopentyl | CH$_3$ | (isoxazol-3-ylamino)carbonyl | |
| 919 | CH(CH$_3$)—C(CH$_3$)$_3$ | H | cyclopentyl | CH$_3$ | [(4-methyl-4H-1,2,4-triazol-3-yl)amino]carbonyl | |
| 920 | CH(CH$_3$)—C(CH$_3$)$_3$ | H | sec-butyl | CH$_3$ | CONHCONHCH$_3$ | |
| 921 | CH(CH$_3$)—C(CH$_3$)$_3$ | H | sec-butyl | CH$_3$ | CONHSO$_2$CF$_3$ | |
| 922 | CH(CH$_3$)—C(CH$_3$)$_3$ | H | sec-butyl | CH$_3$ | CONHSO$_2$CH$_3$ | |
| 923 | CH(CH$_3$)—C(CH$_3$)$_3$ | H | sec-butyl | CH$_3$ | CONHSO$_2$CH$_2$CH$_3$ | |
| 924 | CH(CH$_3$)—C(CH$_3$)$_3$ | H | sec-butyl | CH$_3$ | (isoxazol-3-ylamino)carbonyl | |
| 925 | CH(CH$_3$)—C(CH$_3$)$_3$ | H | sec-butyl | CH$_3$ | [(4-methyl-4H-1,2,4-triazol-3-yl)amino]carbonyl | |
| 926 | CH(CH$_3$)(CF$_3$) | H | 2-chloro-6-fluorophenyl | CH$_3$ | CONHCONHCH$_3$ | |
| 927 | CH(CH$_3$)(CF$_3$) | H | 2-chloro-6-fluorophenyl | CH$_3$ | CONHSO$_2$CF$_3$ | |
| 928 | CH(CH$_3$)(CF$_3$) | H | 2-chloro-6-fluorophenyl | CH$_3$ | CONHSO$_2$CH$_3$ | |
| 929 | CH(CH$_3$)(CF$_3$) | H | 2-chloro-6-fluorophenyl | CH$_3$ | CONHSO$_2$CH$_2$CH$_3$ | |
| 930 | CH(CH$_3$)(CF$_3$) | H | 2-chloro-6-fluorophenyl | CH$_3$ | (isoxazol-3-ylamino)carbonyl | |
| 931 | CH(CH$_3$)(CF$_3$) | H | 2-chloro-6-fluorophenyl | CH$_3$ | [(4-methyl-4H-1,2,4-triazol-3-yl)amino]carbonyl | |
| 932 | CH(CH$_3$)(CF$_3$) | H | 2,4,6-trifluorophenyl | CH$_3$ | CONHCONHCH$_3$ | |
| 933 | CH(CH$_3$)(CF$_3$) | H | 2,4,6-trifluorophenyl | CH$_3$ | CONHSO$_2$CF$_3$ | |
| 934 | CH(CH$_3$)(CF$_3$) | H | 2,4,6-trifluorophenyl | CH$_3$ | CONHSO$_2$CH$_3$ | |
| 935 | CH(CH$_3$)(CF$_3$) | H | 2,4,6-trifluorophenyl | CH$_3$ | CONHSO$_2$CH$_2$CH$_3$ | |
| 936 | CH(CH$_3$)(CF$_3$) | H | 2,4,6-trifluorophenyl | CH$_3$ | (isoxazol-3-ylamino)carbonyl | |
| 937 | CH(CH$_3$)(CF$_3$) | H | 2,4,6-trifluorophenyl | CH$_3$ | [(4-methyl-4H-1,2,4-triazol-3-yl)amino]carbonyl | |
| 938 | CH(CH$_3$)(CF$_3$) | H | 2-chloro-4-fluorophenyl | CH$_3$ | CONHCONHCH$_3$ | |
| 939 | CH(CH$_3$)(CF$_3$) | H | 2-chloro-4-fluorophenyl | CH$_3$ | CONHSO$_2$CF$_3$ | |
| 940 | CH(CH$_3$)(CF$_3$) | H | 2-chloro-4-fluorophenyl | CH$_3$ | CONHSO$_2$CH$_3$ | |
| 941 | CH(CH$_3$)(CF$_3$) | H | 2-chloro-4-fluorophenyl | CH$_3$ | CONHSO$_2$CH$_2$CH$_3$ | |
| 942 | CH(CH$_3$)(CF$_3$) | H | 2-chloro-4-fluorophenyl | CH$_3$ | (isoxazol-3-ylamino)carbonyl | |
| 943 | CH(CH$_3$)(CF$_3$) | H | 2-chloro-4-fluorophenyl | CH$_3$ | [(4-methyl-4H-1,2,4-triazol-3-yl)amino]carbonyl | |
| 944 | CH(CH$_3$)(CF$_3$) | H | 2-chlorophenyl | CH$_3$ | CONHCONHCH$_3$ | |
| 945 | CH(CH$_3$)(CF$_3$) | H | 2-chlorophenyl | CH$_3$ | CONHSO$_2$CF$_3$ | |
| 946 | CH(CH$_3$)(CF$_3$) | H | 2-chlorophenyl | CH$_3$ | CONHSO$_2$CH$_3$ | |
| 947 | CH(CH$_3$)(CF$_3$) | H | 2-chlorophenyl | CH$_3$ | CONHSO$_2$CH$_2$CH$_3$ | |
| 948 | CH(CH$_3$)(CF$_3$) | H | 2-chlorophenyl | CH$_3$ | (isoxazol-3-ylamino)carbonyl | |
| 949 | CH(CH$_3$)(CF$_3$) | H | 2-chlorophenyl | CH$_3$ | [(4-methyl-4H-1,2,4-triazol-3-yl)amino]carbonyl | |
| 950 | CH(CH$_3$)(CF$_3$) | H | 5-Cl-pyrimidin-4-yl | CH$_3$ | CONHCONHCH$_3$ | |
| 951 | CH(CH$_3$)(CF$_3$) | H | 5-Cl-pyrimidin-4-yl | CH$_3$ | CONHSO$_2$CF$_3$ | |
| 952 | CH(CH$_3$)(CF$_3$) | H | 5-Cl-pyrimidin-4-yl | CH$_3$ | CONHSO$_2$CH$_3$ | |
| 953 | CH(CH$_3$)(CF$_3$) | H | 5-Cl-pyrimidin-4-yl | CH$_3$ | CONHSO$_2$CH$_2$CH$_3$ | |
| 954 | CH(CH$_3$)(CF$_3$) | H | 5-Cl-pyrimidin-4-yl | CH$_3$ | (isoxazol-3-ylamino)carbonyl | |
| 955 | CH(CH$_3$)(CF$_3$) | H | 5-Cl-pyrimidin-4-yl | CH$_3$ | [(4-methyl-4H-1,2,4-triazol-3-yl)amino]carbonyl | |
| 956 | CH(CH$_3$)(CF$_3$) | H | 2-chloro-4,6-difluorophenyl | CH$_3$ | CONHCONHCH$_3$ | |
| 957 | CH(CH$_3$)(CF$_3$) | H | 2-chloro-4,6-difluorophenyl | CH$_3$ | CONHSO$_2$CF$_3$ | |
| 958 | CH(CH$_3$)(CF$_3$) | H | 2-chloro-4,6-difluorophenyl | CH$_3$ | CONHSO$_2$CH$_3$ | |
| 959 | CH(CH$_3$)(CF$_3$) | H | 2-chloro-4,6-difluorophenyl | CH$_3$ | CONHSO$_2$CH$_2$CH$_3$ | |
| 960 | CH(CH$_3$)(CF$_3$) | H | 2-chloro-4,6-difluorophenyl | CH$_3$ | (isoxazol-3-ylamino)carbonyl | |
| 961 | CH(CH$_3$)(CF$_3$) | H | 2-chloro-4,6-difluorophenyl | CH$_3$ | [(4-methyl-4H-1,2,4-triazol-3-yl)amino]carbonyl | |
| 962 | CH(CH$_3$)(CF$_3$) | H | 2,4-dichlorophenyl | CH$_3$ | CONHCONHCH$_3$ | |
| 963 | CH(CH$_3$)(CF$_3$) | H | 2,4-dichlorophenyl | CH$_3$ | CONHSO$_2$CF$_3$ | |

TABLE 1-continued

| Ex. No. | R¹ or —R¹⁺R²— | R² | R3 | X | R4 | log p |
|---|---|---|---|---|---|---|
| 964 | CH(CH₃)(CF₃) | H | 2,4-dichlorophenyl | CH₃ | CONHSO₂CH₃ | |
| 965 | CH(CH₃)(CF₃) | H | 2,4-dichlorophenyl | CH₃ | CONHSO₂CH₂CH₃ | |
| 966 | CH(CH₃)(CF₃) | H | 2,4-dichlorophenyl | CH₃ | (isoxazol-3-ylamino)carbonyl | |
| 967 | CH(CH₃)(CF₃) | H | 2,4-dichlorophenyl | CH₃ | [(4-methyl-4H-1,2,4-triazol-3-yl)amino]carbonyl | |
| 968 | CH(CH₃)(CF₃) | H | 4-chloro-2,6-difluorophenyl | CH₃ | CONHCONHCH₃ | |
| 969 | CH(CH₃)(CF₃) | H | 4-chloro-2,6-difluorophenyl | CH₃ | CONHSO₂CF₃ | |
| 970 | CH(CH₃)(CF₃) | H | 4-chloro-2,6-difluorophenyl | CH₃ | CONHSO₂CH₃ | |
| 971 | CH(CH₃)(CF₃) | H | 4-chloro-2,6-difluorophenyl | CH₃ | CONHSO₂CH₂CH₃ | |
| 972 | CH(CH₃)(CF₃) | H | 4-chloro-2,6-difluorophenyl | CH₃ | (isoxazol-3-ylamino)carbonyl | |
| 973 | CH(CH₃)(CF₃) | H | 4-chloro-2,6-difluorophenyl | CH₃ | [(4-methyl-4H-1,2,4-triazol-3-yl)amino]carbonyl | |
| 974 | CH(CH₃)(CF₃) | H | 2,6-difluoro-4-methylphenyl | CH₃ | CONHCONHCH₃ | |
| 975 | CH(CH₃)(CF₃) | H | 2,6-difluoro-4-methylphenyl | CH₃ | CONHSO₂CF₃ | |
| 976 | CH(CH₃)(CF₃) | H | 2,6-difluoro-4-methylphenyl | CH₃ | CONHSO₂CH₃ | |
| 977 | CH(CH₃)(CF₃) | H | 2,6-difluoro-4-methylphenyl | CH₃ | CONHSO₂CH₂CH₃ | |
| 978 | CH(CH₃)(CF₃) | H | 2,6-difluoro-4-methylphenyl | CH₃ | (isoxazol-3-ylamino)carbonyl | |
| 979 | CH(CH₃)(CF₃) | H | 2,6-difluoro-4-methylphenyl | CH₃ | [(4-methyl-4H-1,2,4-triazol-3-yl)amino]carbonyl | |
| 980 | CH(CH₃)(CF₃) | H | 2-chloro-5-fluorophenyl | CH₃ | CONHCONHCH₃ | |
| 981 | CH(CH₃)(CF₃) | H | 2-chloro-5-fluorophenyl | CH₃ | CONHSO₂CF₃ | |
| 982 | CH(CH₃)(CF₃) | H | 2-chloro-5-fluorophenyl | CH₃ | CONHSO₂CH₃ | |
| 983 | CH(CH₃)(CF₃) | H | 2-chloro-5-fluorophenyl | CH₃ | CONHSO₂CH₂CH₃ | |
| 984 | CH(CH₃)(CF₃) | H | 2-chloro-5-fluorophenyl | CH₃ | (isoxazol-3-ylamino)carbonyl | |
| 985 | CH(CH₃)(CF₃) | H | 2-chloro-5-fluorophenyl | CH₃ | [(4-methyl-4H-1,2,4-triazol-3-yl)amino]carbonyl | |
| 986 | CH(CH₃)(CF₃) | H | 3-chloro-2-thienyl | CH₃ | CONHCONHCH₃ | |
| 987 | CH(CH₃)(CF₃) | H | 3-chloro-2-thienyl | CH₃ | CONHSO₂CF₃ | |
| 988 | CH(CH₃)(CF₃) | H | 3-chloro-2-thienyl | CH₃ | CONHSO₂CH₃ | |
| 989 | CH(CH₃)(CF₃) | H | 3-chloro-2-thienyl | CH₃ | CONHSO₂CH₂CH₃ | |
| 990 | CH(CH₃)(CF₃) | H | 3-chloro-2-thienyl | CH₃ | (isoxazol-3-ylamino)carbonyl | |
| 991 | CH(CH₃)(CF₃) | H | 3-chloro-2-thienyl | CH₃ | [(4-methyl-4H-1,2,4-triazol-3-yl)amino]carbonyl | |
| 992 | CH(CH₃)(CF₃) | H | phenyl | CH₃ | CONHCONHCH₃ | |
| 993 | CH(CH₃)(CF₃) | H | phenyl | CH₃ | CONHSO₂CF₃ | |
| 994 | CH(CH₃)(CF₃) | H | phenyl | CH₃ | CONHSO₂CH₃ | |
| 995 | CH(CH₃)(CF₃) | H | phenyl | CH₃ | CONHSO₂CH₂CH₃ | |
| 996 | CH(CH₃)(CF₃) | H | phenyl | CH₃ | (isoxazol-3-ylamino)carbonyl | |
| 997 | CH(CH₃)(CF₃) | H | phenyl | CH₃ | [(4-methyl-4H-1,2,4-triazol-3-yl)amino]carbonyl | |
| 998 | CH(CH₃)(CF₃) | H | cyclopentyl | CH₃ | CONHCONHCH₃ | |
| 999 | CH(CH₃)(CF₃) | H | cyclopentyl | CH₃ | CONHSO₂CF₃ | |
| 1000 | CH(CH₃)(CF₃) | H | cyclopentyl | CH₃ | CONHSO₂CH₃ | |
| 1001 | CH(CH₃)(CF₃) | H | cyclopentyl | CH₃ | CONHSO₂CH₂CH₃ | |
| 1002 | CH(CH₃)(CF₃) | H | cyclopentyl | CH₃ | (isoxazol-3-ylamino)carbonyl | |
| 1003 | CH(CH₃)(CF₃) | H | cyclopentyl | CH₃ | [(4-methyl-4H-1,2,4-triazol-3-yl)amino]carbonyl | |
| 1004 | CH(CH₃)(CF₃) | H | sec-butyl | CH₃ | CONHCONHCH₃ | |
| 1005 | CH(CH₃)(CF₃) | H | sec-butyl | CH₃ | CONHSO₂CF₃ | |
| 1006 | CH(CH₃)(CF₃) | H | sec-butyl | CH₃ | CONHSO₂CH₃ | |
| 1007 | CH(CH₃)(CF₃) | H | sec-butyl | CH₃ | CONHSO₂CH₂CH₃ | |
| 1008 | CH(CH₃)(CF₃) | H | sec-butyl | CH₃ | (isoxazol-3-ylamino)carbonyl | |
| 1009 | CH(CH₃)(CF₃) | H | sec-butyl | CH₃ | [(4-methyl-4H-1,2,4-triazol-3-yl)amino]carbonyl | |
| 1010 | CH(CH₃)—CH(CH₃)₂ | H | 2-chloro-6-fluorophenyl | CH₃ | CONHCONHCH₃ | |

TABLE 1-continued

| Ex. No. | R¹ or —R¹⁺R²— | R² R3 | R3 | X | R4 | log p |
|---|---|---|---|---|---|---|
| 1011 | CH(CH₃)—CH(CH₃)₂ | H | 2-chloro-6-fluorophenyl | CH₃ | CONHSO₂CF₃ | |
| 1012 | CH(CH₃)—CH(CH₃)₂ | H | 2-chloro-6-fluorophenyl | CH₃ | CONHSO₂CH₃ | |
| 1013 | CH(CH₃)—CH(CH₃)₂ | H | 2-chloro-6-fluorophenyl | CH₃ | CONHSO₂CH₂CH₃ | |
| 1014 | CH(CH₃)—CH(CH₃)₂ | H | 2-chloro-6-fluorophenyl | CH₃ | (isoxazol-3-ylamino)carbonyl | |
| 1015 | CH(CH₃)—CH(CH₃)₂ | H | 2-chloro-6-fluorophenyl | CH₃ | [(4-methyl-4H-1,2,4-triazol-3-yl)amino]carbonyl | |
| 1016 | CH(CH₃)—CH(CH₃)₂ | H | 2,4,6-trifluorophenyl | CH₃ | CONHCONHCH₃ | |
| 1017 | CH(CH₃)—CH(CH₃)₂ | H | 2,4,6-trifluorophenyl | CH₃ | CONHSO₂CF₃ | |
| 1018 | CH(CH₃)—CH(CH₃)₂ | H | 2,4,6-trifluorophenyl | CH₃ | CONHSO₂CH₃ | |
| 1019 | CH(CH₃)—CH(CH₃)₂ | H | 2,4,6-trifluorophenyl | CH₃ | CONHSO₂CH₂CH₃ | |
| 1020 | CH(CH₃)—CH(CH₃)₂ | H | 2,4,6-trifluorophenyl | CH₃ | (isoxazol-3-ylamino)carbonyl | |
| 1021 | CH(CH₃)—CH(CH₃)₂ | H | 2,4,6-trifluorophenyl | CH₃ | [(4-methyl-4H-1,2,4-triazol-3-yl)amino]carbonyl | |
| 1022 | CH(CH₃)—CH(CH₃)₂ | H | 2-chloro-4-fluorophenyl | CH₃ | CONHCONHCH₃ | |
| 1023 | CH(CH₃)—CH(CH₃)₂ | H | 2-chloro-4-fluorophenyl | CH₃ | CONHSO₂CF₃ | |
| 1024 | CH(CH₃)—CH(CH₃)₂ | H | 2-chloro-4-fluorophenyl | CH₃ | CONHSO₂CH₃ | |
| 1025 | CH(CH₃)—CH(CH₃)₂ | H | 2-chloro-4-fluorophenyl | CH₃ | CONHSO₂CH₂CH₃ | |
| 1026 | CH(CH₃)—CH(CH₃)₂ | H | 2-chloro-4-fluorophenyl | CH₃ | (isoxazol-3-ylamino)carbonyl | |
| 1027 | CH(CH₃)—CH(CH₃)₂ | H | 2-chloro-4-fluorophenyl | CH₃ | [(4-methyl-4H-1,2,4-triazol-3-yl)amino]carbonyl | |
| 1028 | CH(CH₃)—CH(CH₃)₂ | H | 2-chlorophenyl | CH₃ | CONHCONHCH₃ | |
| 1029 | CH(CH₃)—CH(CH₃)₂ | H | 2-chlorophenyl | CH₃ | CONHSO₂CF₃ | |
| 1030 | CH(CH₃)—CH(CH₃)₂ | H | 2-chlorophenyl | CH₃ | CONHSO₂CH₃ | |
| 1031 | CH(CH₃)—CH(CH₃)₂ | H | 2-chlorophenyl | CH₃ | CONHSO₂CH₂CH₃ | |
| 1032 | CH(CH₃)—CH(CH₃)₂ | H | 2-chlorophenyl | CH₃ | (isoxazol-3-ylamino)carbonyl | |
| 1033 | CH(CH₃)—CH(CH₃)₂ | H | 2-chlorophenyl | CH₃ | [(4-methyl-4H-1,2,4-triazol-3-yl)amino]carbonyl | |
| 1034 | CH(CH₃)—CH(CH₃)₂ | H | 5-Cl-pyrimidin-4-yl | CH₃ | CONHCONHCH₃ | |
| 1035 | CH(CH₃)—CH(CH₃)₂ | H | 5-Cl-pyrimidin-4-yl | CH₃ | CONHSO₂CF₃ | |
| 1036 | CH(CH₃)—CH(CH₃)₂ | H | 5-Cl-pyrimidin-4-yl | CH₃ | CONHSO₂CH₃ | |
| 1037 | CH(CH₃)—CH(CH₃)₂ | H | 5-Cl-pyrimidin-4-yl | CH₃ | CONHSO₂CH₂CH₃ | |
| 1038 | CH(CH₃)—CH(CH₃)₂ | H | 5-Cl-pyrimidin-4-yl | CH₃ | (isoxazol-3-ylamino)carbonyl | |
| 1039 | CH(CH₃)—CH(CH₃)₂ | H | 5-Cl-pyrimidin-4-yl | CH₃ | [(4-methyl-4H-1,2,4-triazol-3-yl)amino]carbonyl | |
| 1040 | CH(CH₃)—CH(CH₃)₂ | H | 2-chloro-4,6-difluorophenyl | CH₃ | CONHCONHCH₃ | |
| 1041 | CH(CH₃)—CH(CH₃)₂ | H | 2-chloro-4,6-difluorophenyl | CH₃ | CONHSO₂CF₃ | |
| 1042 | CH(CH₃)—CH(CH₃)₂ | H | 2-chloro-4,6-difluorophenyl | CH₃ | CONHSO₂CH₃ | |
| 1043 | CH(CH₃)—CH(CH₃)₂ | H | 2-chloro-4,6-difluorophenyl | CH₃ | CONHSO₂CH₂CH₃ | |
| 1044 | CH(CH₃)—CH(CH₃)₂ | H | 2-chloro-4,6-difluorophenyl | CH₃ | (isoxazol-3-ylamino)carbonyl | |
| 1045 | CH(CH₃)—CH(CH₃)₂ | H | 2-chloro-4,6-difluorophenyl | CH₃ | [(4-methyl-4H-1,2,4-triazol-3-yl)amino]carbonyl | |
| 1046 | CH(CH₃)—CH(CH₃)₂ | H | 2,4-dichlorophenyl | CH₃ | CONHCONHCH₃ | |
| 1047 | CH(CH₃)—CH(CH₃)₂ | H | 2,4-dichlorophenyl | CH₃ | CONHSO₂CF₃ | |
| 1048 | CH(CH₃)—CH(CH₃)₂ | H | 2,4-dichlorophenyl | CH₃ | CONHSO₂CH₃ | |
| 1049 | CH(CH₃)—CH(CH₃)₂ | H | 2,4-dichlorophenyl | CH₃ | CONHSO₂CH₂CH₃ | |
| 1050 | CH(CH₃)—CH(CH₃)₂ | H | 2,4-dichlorophenyl | CH₃ | (isoxazol-3-ylamino)carbonyl | |
| 1051 | CH(CH₃)—CH(CH₃)₂ | H | 2,4-dichlorophenyl | CH₃ | [(4-methyl-4H-1,2,4-triazol-3-yl)amino]carbonyl | |
| 1052 | CH(CH₃)—CH(CH₃)₂ | H | 4-chloro-2,6-difluorophenyl | CH₃ | CONHCONHCH₃ | |
| 1053 | CH(CH₃)—CH(CH₃)₂ | H | 4-chloro-2,6-difluorophenyl | CH₃ | CONHSO₂CF₃ | |
| 1054 | CH(CH₃)—CH(CH₃)₂ | H | 4-chloro-2,6-difluorophenyl | CH₃ | CONHSO₂CH₃ | |
| 1055 | CH(CH₃)—CH(CH₃)₂ | H | 4-chloro-2,6-difluorophenyl | CH₃ | CONHSO₂CH₂CH₃ | |
| 1056 | CH(CH₃)—CH(CH₃)₂ | H | 4-chloro-2,6-difluorophenyl | CH₃ | (isoxazol-3-ylamino)carbonyl | |
| 1057 | CH(CH₃)—CH(CH₃)₂ | H | 4-chloro-2,6-difluorophenyl | CH₃ | [(4-methyl-4H-1,2,4-triazol-3-yl)amino]carbonyl | |

TABLE 1-continued

[Structure: pyrazolo-pyrimidine core with NR¹R² at top, R³, X, N, R⁴ substituents]

| Ex. No. | R¹ or —R¹⁺R²— | R² | R3 | X | R4 | log p |
|---|---|---|---|---|---|---|
| 1058 | CH(CH₃)—CH(CH₃)₂ | H | 2,6-difluoro-4-methylphenyl | CH₃ | CONHCONHCH₃ | |
| 1059 | CH(CH₃)—CH(CH₃)₂ | H | 2,6-difluoro-4-methylphenyl | CH₃ | CONHSO₂CF₃ | |
| 1060 | CH(CH₃)—CH(CH₃)₂ | H | 2,6-difluoro-4-methylphenyl | CH₃ | CONHSO₂CH₃ | |
| 1061 | CH(CH₃)—CH(CH₃)₂ | H | 2,6-difluoro-4-methylphenyl | CH₃ | CONHSO₂CH₂CH₃ | |
| 1062 | CH(CH₃)—CH(CH₃)₂ | H | 2,6-difluoro-4-methylphenyl | CH₃ | (isoxazol-3-ylamino)carbonyl | |
| 1063 | CH(CH₃)—CH(CH₃)₂ | H | 2,6-difluoro-4-methylphenyl | CH₃ | [(4-methyl-4H-1,2,4-triazol-3-yl)amino]carbonyl | |
| 1064 | CH(CH₃)—CH(CH₃)₂ | H | 2-chloro-5-fluorophenyl | CH₃ | CONHCONHCH₃ | |
| 1065 | CH(CH₃)—CH(CH₃)₂ | H | 2-chloro-5-fluorophenyl | CH₃ | CONHSO₂CF₃ | |
| 1066 | CH(CH₃)—CH(CH₃)₂ | H | 2-chloro-5-fluorophenyl | CH₃ | CONHSO₂CH₃ | |
| 1067 | CH(CH₃)—CH(CH₃)₂ | H | 2-chloro-5-fluorophenyl | CH₃ | CONHSO₂CH₂CH₃ | |
| 1068 | CH(CH₃)—CH(CH₃)₂ | H | 2-chloro-5-fluorophenyl | CH₃ | (isoxazol-3-ylamino)carbonyl | |
| 1069 | CH(CH₃)—CH(CH₃)₂ | H | 2-chloro-5-fluorophenyl | CH₃ | [(4-methyl-4H-1,2,4-triazol-3-yl)amino]carbonyl | |
| 1070 | CH(CH₃)—CH(CH₃)₂ | H | 3-chloro-2-thienyl | CH₃ | CONHCONHCH₃ | |
| 1071 | CH(CH₃)—CH(CH₃)₂ | H | 3-chloro-2-thienyl | CH₃ | CONHSO₂CF₃ | |
| 1072 | CH(CH₃)—CH(CH₃)₂ | H | 3-chloro-2-thienyl | CH₃ | CONHSO₂CH₃ | |
| 1073 | CH(CH₃)—CH(CH₃)₂ | H | 3-chloro-2-thienyl | CH₃ | CONHSO₂CH₂CH₃ | |
| 1074 | CH(CH₃)—CH(CH₃)₂ | H | 3-chloro-2-thienyl | CH₃ | (isoxazol-3-ylamino)carbonyl | |
| 1075 | CH(CH₃)—CH(CH₃)₂ | H | 3-chloro-2-thienyl | CH₃ | [(4-methyl-4H-1,2,4-triazol-3-yl)amino]carbonyl | |
| 1076 | CH(CH₃)—CH(CH₃)₂ | H | phenyl | CH₃ | CONHCONHCH₃ | |
| 1077 | CH(CH₃)—CH(CH₃)₂ | H | phenyl | CH₃ | CONHSO₂CF₃ | |
| 1078 | CH(CH₃)—CH(CH₃)₂ | H | phenyl | CH₃ | CONHSO₂CH₃ | |
| 1079 | CH(CH₃)—CH(CH₃)₂ | H | phenyl | CH₃ | CONHSO₂CH₂CH₃ | |
| 1080 | CH(CH₃)—CH(CH₃)₂ | H | phenyl | CH₃ | (isoxazol-3-ylamino)carbonyl | |
| 1081 | CH(CH₃)—CH(CH₃)₂ | H | phenyl | CH₃ | [(4-methyl-4H-1,2,4-triazol-3-yl)amino]carbonyl | |
| 1082 | CH(CH₃)—CH(CH₃)₂ | H | cyclopentyl | CH₃ | CONHCONHCH₃ | |
| 1083 | CH(CH₃)—CH(CH₃)₂ | H | cyclopentyl | CH₃ | CONHSO₂CF₃ | |
| 1084 | CH(CH₃)—CH(CH₃)₂ | H | cyclopentyl | CH₃ | CONHSO₂CH₃ | |
| 1085 | CH(CH₃)—CH(CH₃)₂ | H | cyclopentyl | CH₃ | CONHSO₂CH₂CH₃ | |
| 1086 | CH(CH₃)—CH(CH₃)₂ | H | cyclopentyl | CH₃ | (isoxazol-3-ylamino)carbonyl | |
| 1087 | CH(CH₃)—CH(CH₃)₂ | H | cyclopentyl | CH₃ | [(4-methyl-4H-1,2,4-triazol-3-yl)amino]carbonyl | |
| 1088 | CH(CH₃)—CH(CH₃)₂ | H | sec-butyl | CH₃ | CONHCONHCH₃ | |
| 1089 | CH(CH₃)—CH(CH₃)₂ | H | sec-butyl | CH₃ | CONHSO₂CF₃ | |
| 1090 | CH(CH₃)—CH(CH₃)₂ | H | sec-butyl | CH₃ | CONHSO₂CH₃ | |
| 1091 | CH(CH₃)—CH(CH₃)₂ | H | sec-butyl | CH₃ | CONHSO₂CH₂CH₃ | |
| 1092 | CH(CH₃)—CH(CH₃)₂ | H | sec-butyl | CH₃ | (isoxazol-3-ylamino)carbonyl | |
| 1093 | CH(CH₃)—CH(CH₃)₂ | H | sec-butyl | CH₃ | [(4-methyl-4H-1,2,4-triazol-3-yl)amino]carbonyl | |
| 1094 | —CH₂—CH₂—CH(CH₃)—CH₂—CH₂— | | 2-chloro-6-fluorophenyl | CH₃ | CONHCONHCH₃ | |
| 1095 | —CH₂—CH₂—CH(CH₃)—CH₂—CH₂— | | 2-chloro-6-fluorophenyl | CH₃ | CONHSO₂CF₃ | |
| 1096 | —CH₂—CH₂—CH(CH₃)—CH₂—CH₂— | | 2-chloro-6-fluorophenyl | CH₃ | CONHSO₂CH₃ | |
| 1097 | —CH₂—CH₂—CH(CH₃)—CH₂—CH₂— | | 2-chloro-6-fluorophenyl | CH₃ | CONHSO₂CH₂CH₃ | |
| 1098 | —CH₂—CH₂—CH(CH₃)—CH₂—CH₂— | | 2-chloro-6-fluorophenyl | CH₃ | (isoxazol-3-ylamino)carbonyl | |
| 1099 | —CH₂—CH₂—CH(CH₃)—CH₂—CH₂— | | 2-chloro-6-fluorophenyl | CH₃ | [(4-methyl-4H-1,2,4-triazol-3-yl)amino]carbonyl | |
| 1100 | —CH₂—CH₂—CH(CH₃)—CH₂—CH₂— | | 2,4,6-trifluorophenyl | CH₃ | CONHCONHCH₃ | |
| 1101 | —CH₂—CH₂—CH(CH₃)—CH₂—CH₂— | | 2,4,6-trifluorophenyl | CH₃ | CONHSO₂CF₃ | |
| 1102 | —CH₂—CH₂—CH(CH₃)—CH₂—CH₂— | | 2,4,6-trifluorophenyl | CH₃ | CONHSO₂CH₃ | |
| 1103 | —CH₂—CH₂—CH(CH₃)—CH₂—CH₂— | | 2,4,6-trifluorophenyl | CH₃ | CONHSO₂CH₂CH₃ | |
| 1104 | —CH₂—CH₂—CH(CH₃)—CH₂—CH₂— | | 2,4,6-trifluorophenyl | CH₃ | (isoxazol-3-ylamino)carbonyl | |
| 1105 | —CH₂—CH₂—CH(CH₃)—CH₂—CH₂— | | 2,4,6-trifluorophenyl | CH₃ | [(4-methyl-4H-1,2,4-triazol-3-yl)amino]carbonyl | |
| 1106 | —CH₂—CH₂—CH(CH₃)—CH₂—CH₂— | | 2-chloro-4-fluorophenyl | CH₃ | CONHCONHCH₃ | |
| 1107 | —CH₂—CH₂—CH(CH₃)—CH₂—CH₂— | | 2-chloro-4-fluorophenyl | CH₃ | CONHSO₂CF₃ | |
| 1108 | —CH₂—CH₂—CH(CH₃)—CH₂—CH₂— | | 2-chloro-4-fluorophenyl | CH₃ | CONHSO₂CH₃ | |
| 1109 | —CH₂—CH₂—CH(CH₃)—CH₂—CH₂— | | 2-chloro-4-fluorophenyl | CH₃ | CONHSO₂CH₂CH₃ | |

TABLE 1-continued

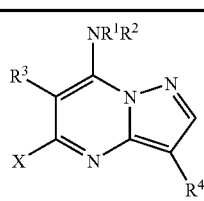

| Ex. No. | $R^1$ or $R^2$ —$R^{1+}R^2$— | R3 | X | R4 | log p |
|---|---|---|---|---|---|
| 1110 | —CH$_2$—CH$_2$—CH(CH$_3$)—CH$_2$—CH$_2$— | 2-chloro-4-fluorophenyl | CH$_3$ | (isoxazol-3-ylamino)carbonyl | |
| 1111 | —CH$_2$—CH$_2$—CH(CH$_3$)—CH$_2$—CH$_2$— | 2-chloro-4-fluorophenyl | CH$_3$ | [(4-methyl-4H-1,2,4-triazol-3-yl)amino]carbonyl | |
| 1112 | —CH$_2$—CH$_2$—CH(CH$_3$)—CH$_2$—CH$_2$— | 2-chlorophenyl | CH$_3$ | CONHCONHCH$_3$ | |
| 1113 | —CH$_2$—CH$_2$—CH(CH$_3$)—CH$_2$—CH$_2$— | 2-chlorophenyl | CH$_3$ | CONHSO$_2$CF$_3$ | |
| 1114 | —CH$_2$—CH$_2$—CH(CH$_3$)—CH$_2$—CH$_2$— | 2-chlorophenyl | CH$_3$ | CONHSO$_2$CH$_3$ | |
| 1115 | —CH$_2$—CH$_2$—CH(CH$_3$)—CH$_2$—CH$_2$— | 2-chlorophenyl | CH$_3$ | CONHSO$_2$CH$_2$CH$_3$ | |
| 1116 | —CH$_2$—CH$_2$—CH(CH$_3$)—CH$_2$—CH$_2$— | 2-chlorophenyl | CH$_3$ | (isoxazol-3-ylamino)carbonyl | |
| 1117 | —CH$_2$—CH$_2$—CH(CH$_3$)—CH$_2$—CH$_2$— | 2-chlorophenyl | CH$_3$ | [(4-methyl-4H-1,2,4-triazol-3-yl)amino]carbonyl | |
| 1118 | —CH$_2$—CH$_2$—CH(CH$_3$)—CH$_2$—CH$_2$— | 5-Cl-pyrimidin-4-yl | CH$_3$ | CONHCONHCH$_3$ | |
| 1119 | —CH$_2$—CH$_2$—CH(CH$_3$)—CH$_2$—CH$_2$— | 5-Cl-pyrimidin-4-yl | CH$_3$ | CONHSO$_2$CF$_3$ | |
| 1120 | —CH$_2$—CH$_2$—CH(CH$_3$)—CH$_2$—CH$_2$— | 5-Cl-pyrimidin-4-yl | CH$_3$ | CONHSO$_2$CH$_3$ | |
| 1121 | —CH$_2$—CH$_2$—CH(CH$_3$)—CH$_2$—CH$_2$— | 5-Cl-pyrimidin-4-yl | CH$_3$ | CONHSO$_2$CH$_2$CH$_3$ | |
| 1122 | —CH$_2$—CH$_2$—CH(CH$_3$)—CH$_2$—CH$_2$— | 5-Cl-pyrimidin-4-yl | CH$_3$ | (isoxazol-3-ylamino)carbonyl | |
| 1123 | —CH$_2$—CH$_2$—CH(CH$_3$)—CH$_2$—CH$_2$— | 5-Cl-pyrimidin-4-yl | CH$_3$ | [(4-methyl-4H-1,2,4-triazol-3-yl)amino]carbonyl | |
| 1124 | —CH$_2$—CH$_2$—CH(CH$_3$)—CH$_2$—CH$_2$— | 2-chloro-4,6-difluorophenyl | CH$_3$ | CONHCONHCH$_3$ | |
| 1125 | —CH$_2$—CH$_2$—CH(CH$_3$)—CH$_2$—CH$_2$— | 2-chloro-4,6-difluorophenyl | CH$_3$ | CONHSO$_2$CF$_3$ | |
| 1126 | —CH$_2$—CH$_2$—CH(CH$_3$)—CH$_2$—CH$_2$— | 2-chloro-4,6-difluorophenyl | CH$_3$ | CONHSO$_2$CH$_3$ | |
| 1127 | —CH$_2$—CH$_2$—CH(CH$_3$)—CH$_2$—CH$_2$— | 2-chloro-4,6-difluorophenyl | CH$_3$ | CONHSO$_2$CH$_2$CH$_3$ | |
| 1128 | —CH$_2$—CH$_2$—CH(CH$_3$)—CH$_2$—CH$_2$— | 2-chloro-4,6-difluorophenyl | CH$_3$ | (isoxazol-3-ylamino)carbonyl | |
| 1129 | —CH$_2$—CH$_2$—CH(CH$_3$)—CH$_2$—CH$_2$— | 2-chloro-4,6-difluorophenyl | CH$_3$ | [(4-methyl-4H-1,2,4-triazol-3-yl)amino]carbonyl | |
| 1130 | —CH$_2$—CH$_2$—CH(CH$_3$)—CH$_2$—CH$_2$— | 2,4-dichlorophenyl | CH$_3$ | CONHCONHCH$_3$ | |
| 1131 | —CH$_2$—CH$_2$—CH(CH$_3$)—CH$_2$—CH$_2$— | 2,4-dichlorophenyl | CH$_3$ | CONHSO$_2$CF$_3$ | |
| 1132 | —CH$_2$—CH$_2$—CH(CH$_3$)—CH$_2$—CH$_2$— | 2,4-dichlorophenyl | CH$_3$ | CONHSO$_2$CH$_3$ | |
| 1133 | —CH$_2$—CH$_2$—CH(CH$_3$)—CH$_2$—CH$_2$— | 2,4-dichlorophenyl | CH$_3$ | CONHSO$_2$CH$_2$CH$_3$ | |
| 1134 | —CH$_2$—CH$_2$—CH(CH$_3$)—CH$_2$—CH$_2$— | 2,4-dichlorophenyl | CH$_3$ | (isoxazol-3-ylamino)carbonyl | |
| 1135 | —CH$_2$—CH$_2$—CH(CH$_3$)—CH$_2$—CH$_2$— | 2,4-dichlorophenyl | CH$_3$ | [(4-methyl-4H-1,2,4-triazol-3-yl)amino]carbonyl | |
| 1136 | —CH$_2$—CH$_2$—CH(CH$_3$)—CH$_2$—CH$_2$— | 4-chloro-2,6-difluorophenyl | CH$_3$ | CONHCONHCH$_3$ | |
| 1137 | —CH$_2$—CH$_2$—CH(CH$_3$)—CH$_2$—CH$_2$— | 4-chloro-2,6-difluorophenyl | CH$_3$ | CONHSO$_2$CF$_3$ | |
| 1138 | —CH$_2$—CH$_2$—CH(CH$_3$)—CH$_2$—CH$_2$— | 4-chloro-2,6-difluorophenyl | CH$_3$ | CONHSO$_2$CH$_3$ | |
| 1139 | —CH$_2$—CH$_2$—CH(CH$_3$)—CH$_2$—CH$_2$— | 4-chloro-2,6-difluorophenyl | CH$_3$ | CONHSO$_2$CH$_2$CH$_3$ | |
| 1140 | —CH$_2$—CH$_2$—CH(CH$_3$)—CH$_2$—CH$_2$— | 4-chloro-2,6-difluorophenyl | CH$_3$ | (isoxazol-3-ylamino)carbonyl | |
| 1141 | —CH$_2$—CH$_2$—CH(CH$_3$)—CH$_2$—CH$_2$— | 4-chloro-2,6-difluorophenyl | CH$_3$ | [(4-methyl-4H-1,2,4-triazol-3-yl)amino]carbonyl | |
| 1142 | —CH$_2$—CH$_2$—CH(CH$_3$)—CH$_2$—CH$_2$— | 2,6-difluoro-4-methylphenyl | CH$_3$ | CONHCONHCH$_3$ | |
| 1143 | —CH$_2$—CH$_2$—CH(CH$_3$)—CH$_2$—CH$_2$— | 2,6-difluoro-4-methylphenyl | CH$_3$ | CONHSO$_2$CF$_3$ | |
| 1144 | —CH$_2$—CH$_2$—CH(CH$_3$)—CH$_2$—CH$_2$— | 2,6-difluoro-4-methylphenyl | CH$_3$ | CONHSO$_2$CH$_3$ | |
| 1145 | —CH$_2$—CH$_2$—CH(CH$_3$)—CH$_2$—CH$_2$— | 2,6-difluoro-4-methylphenyl | CH$_3$ | CONHSO$_2$CH$_2$CH$_3$ | |
| 1146 | —CH$_2$—CH$_2$—CH(CH$_3$)—CH$_2$—CH$_2$— | 2,6-difluoro-4-methylphenyl | CH$_3$ | (isoxazol-3-ylamino)carbonyl | |
| 1147 | —CH$_2$—CH$_2$—CH(CH$_3$)—CH$_2$—CH$_2$— | 2,6-difluoro-4-methylphenyl | CH$_3$ | [(4-methyl-4H-1,2,4-triazol-3-yl)amino]carbonyl | |
| 1148 | —CH$_2$—CH$_2$—CH(CH$_3$)—CH$_2$—CH$_2$— | 2-chloro-5-fluorophenyl | CH$_3$ | CONHCONHCH$_3$ | |
| 1149 | —CH$_2$—CH$_2$—CH(CH$_3$)—CH$_2$—CH$_2$— | 2-chloro-5-fluorophenyl | CH$_3$ | CONHSO$_2$CF$_3$ | |
| 1150 | —CH$_2$—CH$_2$—CH(CH$_3$)—CH$_2$—CH$_2$— | 2-chloro-5-fluorophenyl | CH$_3$ | CONHSO$_2$CH$_3$ | |
| 1151 | —CH$_2$—CH$_2$—CH(CH$_3$)—CH$_2$—CH$_2$— | 2-chloro-5-fluorophenyl | CH$_3$ | CONHSO$_2$CH$_2$CH$_3$ | |
| 1152 | —CH$_2$—CH$_2$—CH(CH$_3$)—CH$_2$—CH$_2$— | 2-chloro-5-fluorophenyl | CH$_3$ | (isoxazol-3-ylamino)carbonyl | |

TABLE 1-continued

Structure: pyrazolo[1,5-a]pyrimidine with NR¹R² at position 7, R³ at position 6, X at position 5, R⁴ at position 3.

| Ex. No. | R¹ or —R¹⁺R²— R² | | R3 | X | R4 | log p |
|---|---|---|---|---|---|---|
| 1153 | —CH₂—CH₂—CH(CH₃)—CH₂—CH₂— | | 2-chloro-5-fluorophenyl | CH₃ | [(4-methyl-4H-1,2,4-triazol-3-yl)amino]carbonyl | |
| 1154 | —CH₂—CH₂—CH(CH₃)—CH₂—CH₂— | | 3-chloro-2-thienyl | CH₃ | CONHCONHCH₃ | |
| 1155 | —CH₂—CH₂—CH(CH₃)—CH₂—CH₂— | | 3-chloro-2-thienyl | CH₃ | CONHSO₂CF₃ | |
| 1156 | —CH₂—CH₂—CH(CH₃)—CH₂—CH₂— | | 3-chloro-2-thienyl | CH₃ | CONHSO₂CH₃ | |
| 1157 | —CH₂—CH₂—CH(CH₃)—CH₂—CH₂— | | 3-chloro-2-thienyl | CH₃ | CONHSO₂CH₂CH₃ | |
| 1158 | —CH₂—CH₂—CH(CH₃)—CH₂—CH₂— | | 3-chloro-2-thienyl | CH₃ | (isoxazol-3-ylamino)carbonyl | |
| 1159 | —CH₂—CH₂—CH(CH₃)—CH₂—CH₂— | | 3-chloro-2-thienyl | CH₃ | [(4-methyl-4H-1,2,4-triazol-3-yl)amino]carbonyl | |
| 1160 | —CH₂—CH₂—CH(CH₃)—CH₂—CH₂— | | phenyl | CH₃ | CONHCONHCH₃ | |
| 1161 | —CH₂—CH₂—CH(CH₃)—CH₂—CH₂— | | phenyl | CH₃ | CONHSO₂CF₃ | |
| 1162 | —CH₂—CH₂—CH(CH₃)—CH₂—CH₂— | | phenyl | CH₃ | CONHSO₂CH₃ | |
| 1163 | —CH₂—CH₂—CH(CH₃)—CH₂—CH₂— | | phenyl | CH₃ | CONHSO₂CH₂CH₃ | |
| 1164 | —CH₂—CH₂—CH(CH₃)—CH₂—CH₂— | | phenyl | CH₃ | (isoxazol-3-ylamino)carbonyl | |
| 1165 | —CH₂—CH₂—CH(CH₃)—CH₂—CH₂— | | phenyl | CH₃ | [(4-methyl-4H-1,2,4-triazol-3-yl)amino]carbonyl | |
| 1166 | —CH₂—CH₂—CH(CH₃)—CH₂—CH₂— | | cyclopentyl | CH₃ | CONHCONHCH₃ | |
| 1167 | —CH₂—CH₂—CH(CH₃)—CH₂—CH₂— | | cyclopentyl | CH₃ | CONHSO₂CF₃ | |
| 1168 | —CH₂—CH₂—CH(CH₃)—CH₂—CH₂— | | cyclopentyl | CH₃ | CONHSO₂CH₃ | |
| 1169 | —CH₂—CH₂—CH(CH₃)—CH₂—CH₂— | | cyclopentyl | CH₃ | CONHSO₂CH₂CH₃ | |
| 1170 | —CH₂—CH₂—CH(CH₃)—CH₂—CH₂— | | cyclopentyl | CH₃ | (isoxazol-3-ylamino)carbonyl | |
| 1171 | —CH₂—CH₂—CH(CH₃)—CH₂—CH₂— | | cyclopentyl | CH₃ | [(4-methyl-4H-1,2,4-triazol-3-yl)amino]carbonyl | |
| 1172 | —CH₂—CH₂—CH(CH₃)—CH₂—CH₂— | | sec-butyl | CH₃ | CONHCONHCH₃ | |
| 1173 | —CH₂—CH₂—CH(CH₃)—CH₂—CH₂— | | sec-butyl | CH₃ | CONHSO₂CF₃ | |
| 1174 | —CH₂—CH₂—CH(CH₃)—CH₂—CH₂— | | sec-butyl | CH₃ | CONHSO₂CH₃ | |
| 1175 | —CH₂—CH₂—CH(CH₃)—CH₂—CH₂— | | sec-butyl | CH₃ | CONHSO₂CH₂CH₃ | |
| 1176 | —CH₂—CH₂—CH(CH₃)—CH₂—CH₂— | | sec-butyl | CH₃ | (isoxazol-3-ylamino)carbonyl | |
| 1177 | —CH₂—CH₂—CH(CH₃)—CH₂—CH₂— | | sec-butyl | CH₃ | [(4-methyl-4H-1,2,4-triazol-3-yl)amino]carbonyl | |
| 1178 | (R) CH(CH₃)—CH(CH₃)₂ | H | 4-fluoro-2-methylphenyl | Cl | CONHCONHCH₃ | 4.42 |
| 1179 | CH(CH3)—CH(CH3)2 | H | 4-fluoro-2-methylphenyl | Cl | pyrimidin-2-ylaminocarbonyl | 6.61 |
| 1180 | CH(CH3)—CH(CH3)2 | H | 2,4-difluorophenyl | Cl | morpholin-4-ylaminocarbonyl | 3.46 |
| 1181 | CH(CH3)—C(CH3)3 | H | 2-chloro-4-methylphenyl | Cl | morpholin-4-ylaminocarbonyl | 4.41 |
| 1182 | CH(CH3)—C(CH3)3 | H | 2,4-difluorophenyl | Cl | morpholin-4-ylaminocarbonyl | 3.76 |
| 1183 | CH(CH3)—CH(CH3)2 | H | 3-Me-thien-2-yl | Cl | morpholin-4-ylaminocarbonyl | 3.63 |
| 1184 | CH(CH3)—CH(CH3)2 | H | 2-chloro-4-fluorophenyl | Cl | 1-methylpyrazol-3-yl-aminocarbonyl | 4.35 |
| 1185 | CH(CH3)—C(CH3)3 | H | 2-chloro-4-fluorophenyl | Cl | 1-methylpyrazol-3-yl-aminocarbonyl | 4.69 |
| 1186 | CH(CH3)—CH(CH3)2 | H | 2-chloro-4-fluorophenyl | Cl | 1-methylpyrazol-5-yl-aminocarbonyl | 4.18 |
| 1187 | CH(CH3)—C(CH3)3 | H | 2-chloro-4-fluorophenyl | Cl | 1-methylpyrazol-4-yl-aminocarbonyl | 4.26 |
| 1188 | CH(CH3)—CH(CH3)2 | H | 2-chloro-4-fluorophenyl | Cl | 1-methyl-1,2,4-triazol-3-yl-aminocarbonyl | 3.62 |
| 1189 | CH(CH3)—CH(CH3)2 | H | 2-chloro-4-fluorophenyl | Cl | 1-methylpyrazol-4-yl-aminocarbonyl | 3.95 |
| 1190 | CH(CH3)—CH(CH3)2 | H | 2,4-difluorophenyl | Cl | CONHSO₂CH₃ | 3.87 |
| 1191 | CH(CH3)—C(CH3)3 | H | 2-chloro-4-fluorophenyl | Cl | 1-methyl-1,2,4-triazol-3-ylaminocarbonyl | 3.91 |
| 1192 | —CH2—CH2—CH(CH3)—CH2—CH2— | | 2-chloro-4-fluorophenyl | Cl | 1-methyl-1,2,4-triazol-3-ylaminocarbonyl | 3.89 |
| 1193 | —CH2—CH2—CH(CH3)—CH2—CH2— | | 2-chloro-4-fluorophenyl | Cl | 1-methylpyrazol-5-ylaminocarbonyl | 4.47 |
| 1194 | CH(CH3)—C(CH3)3 | H | 2-chloro-4-methylphenyl | Cl | CONHSO₂CH₃ | 4.76 |
| 1195 | —CH2—CH2—CH(CH3)—CH2—CH2— | | 2-chloro-4-fluorophenyl | Cl | 1-methylpyrazol-3-ylaminocarbonyl | 4.66 |
| 1196 | —CH2—CH2—CH(CH3)—CH2—CH2— | | 2-chloro-4-fluorophenyl | Cl | 1-methylpyrazol-4-ylaminocarbonyl | 4.31 |

TABLE 1-continued

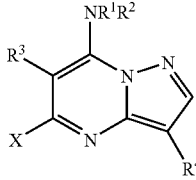

| Ex. No. | $R^1$ or $-R^{1+}R^2-$ | $R^2$ | R3 | X | R4 | log p |
|---|---|---|---|---|---|---|
| 1197 | —CH2—CH2—CH(CH3)—CH2—CH2— | | 2-chloro-4-fluorophenyl | Cl | 1,2,4-triazol-5-ylaminocarbonyl | 4.11 |
| 1198 | CH(CH3)—CH(CH3)2 | H | 2,6-dichloro-4-(trifluoromethoxy)-phenyl | Cl | CONHSO₂CH₃ | 4.85 |

The logP values were determined in accordance with EEC Directive 79/831 Annex V. A8 by HPLC (gradient method, acetonitrile/0.1% aqueous phosphoric acid).
**These logP values were determined in accordance with EEC Directive 79/831 Annex V.A8 by HPLC (gradient method, acetonitrile/0.1% aqueous formic acid).

Preparation of the Starting Materials:

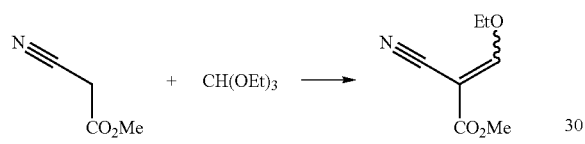

In an apparatus with Vigreux column, 198 g (1998 mmol) of methyl cyanoacetate, 296 g (1998 mmol) of triethyl orthoformate and 440 g (4310 mmol) of acetic anhydride were heated at reflux. Volatile components were distilled off until a head temperature of 120° C. had been reached. After cooling, the mixture was fractionated under reduced pressure. This gave 5 g of methyl (2E/Z)-2-cyano-3-ethoxyacrylate (fraction 1: 65-100° C., 0.2 mbar, 88% pure according to GCMS) and a further 209 g of methyl (2E/Z)-2-cyano-3-ethoxyacrylate (fraction 2: 105-108° C., 0.2 mbar, >99% pure according to GCMS).

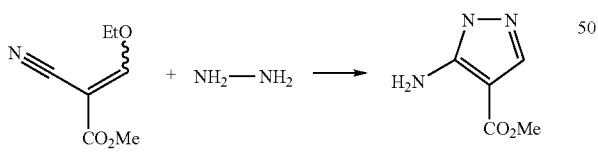

100 g (645 mmol) of methyl (2E/Z)-2-cyano-3-ethoxyacrylate were initially charged in 481 ml of ethanol. 31 ml (645 mmol) of an 85% strength hydrazine hydrate solution were then added dropwise at room temperature with cooling (exothermal temperature!) over a period of 45 minutes. The mixture was stirred at 75° C. for another 12 hours. The hot mixture was filtered and the organic phase was concentrated under reduced pressure. This gave 64 g of methyl 5-amino-1H-pyrazole-4-carboxylate (log P=−0.07; HPLC content: 86%).

Methyl 6-(2,4-dichlorophenyl)-5,7-dihydroxypyrazolo[1,5-a]pyrimidine-3-carboxylate

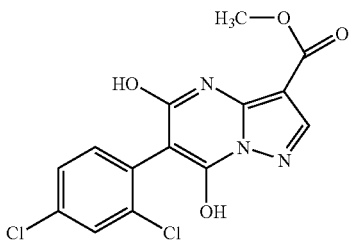

5.5 g of dimethyl 2-(2,4-dichlorophenyl)malonate and 2.8 g of methyl 3-aminopyrazole-4-carboxylate were mixed with 4 g of tri-n-butylamine and stirred at 185° C. for 3 h; the liberated methanol was distilled off during this operation. The mixture was then cooled and excess tri-n-butylamine was removed under reduced pressure. The resulting product was reacted crude, without further purification.

log P*: 1.21

Methyl 5,7-dichloro-6-(2,4-dichlorophenyl)pyrazolo[1,5-a]pyrimidine-3-carboxylate

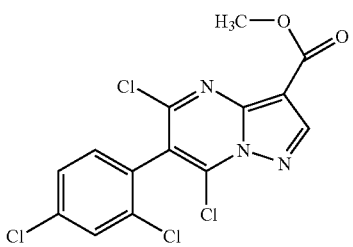

10 g of methyl 6-(2,4-dichlorophenyl)-5,7-dihydroxypyrazolo[1,5-a]pyrimidine-3-carboxylate were dissolved in 43.3 g of phosphoryl chloride and stirred at 120° C. for 3-4 h, until the evolution of gas had ceased. 2.94 g of phosphorus pentachloride were then added, and the mixture was stirred at 120° C. for another 2-3 h. After subsequent cooling, the mixture was concentrated on a rotary evaporator and taken up in water and dichloromethane. The organic phase was separated off and dried with sodium sulphate, and the solvent was removed under reduced pressure. The residue was purified chromatographically (silica gel, cyclohexane/ethyl acetate 9:1, 5:1, 3:1). This gave the title compound.

log P*: 3.86

Methyl 5-chloro-6-(2,4-dichlorophenyl)-7-isopropylaminopyrazolo[1,5-a]pyrimidine-3-carboxylate

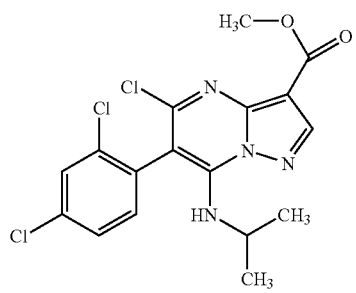

5 g of the dichloro compound obtained above were dissolved in 50 ml of acetonitrile, and 0.831 g of isopropylamine were added. With ice-cooling, 2.651 g of potassium carbonate were added and the mixture was stirred at room temperature for 15 h (monitored by TLC). The mixture was then neutralized with 1 N hydrochloric acid and filtered off with suction. Solid.

log P*: 4.07

5-Chloro-6-(2,4-dichlorophenyl)-7-isopropylaminopyrazolo[1,5-a]pyrimidine-3-carboxylic acid

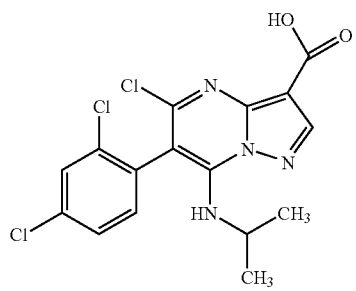

5 g of methyl 5-chloro-6-(2,4-dichlorophenyl)-7-isopropylaminopyrazolo[1,5-a]pyrimidine-3-carboxylate were dissolved in 75 ml of 1,4-dioxane, and 75 ml of 2 N aqueous potassium hydroxide solution were added. The mixture was stirred at room temperature for 15 h (monitored by TLC) and then introduced into 1 N hydrochloric acid. The precipitated solid was filtered off with suction.

log P*: 3.30

The following intermediates were prepared analogously:

| $R^1$ | $R^2$ | $R^3$ | log P |
|---|---|---|---|
| $CH(CH_3)-C(CH_3)_3$ | H | 5-F-pyrimidin-4-yl | 3.15 |
| $CH(CH_3)-CH(CH_3)_2$ | H | 2-Cl-6-F-phenyl | 4.12 |
| $(CH_2-CH_2-CHCH_3-CH_2-CH_2)$ | | 2-Cl-6-F-phenyl | 4.61 |
| $CH(CH_3)-C(CH_3)_3$ | H | 2-Cl-6-F-phenyl | 4.51 |
| $CH(CH_3)-C(CH_3)_3$ | H | 2,4,6-trifluorophenyl | 4.93 |
| $CH(CH_3)-CH(CH_3)_2$ | H | 2,4,6-trifluorophenyl | 4.05 |
| $CH(CH_3)(CF_3)$ | H | 2,4,6-trifluorophenyl | 3.53 |
| $CH(CH_3)(CF_3)$ | H | 2-Cl-4-F-phenyl | 3.75 |
| $CH(CH_3)-CH(CH_3)_2$ | H | 2-Cl-4-F-phenyl | 4.31 |
| $CH(CH_3)-C(CH_3)_3$ | H | 2-Cl-4-F-phenyl | 4.68 |
| $CH(CH_3)-CH(CH_3)_2$ | H | 2-Cl-phenyl | 4.21 |
| $CH(CH_3)-C(CH_3)_3$ | H | 2-Cl-phenyl | 4.61 |

Dimethyl 2-(3-methylthiophen-2-yl)malonate

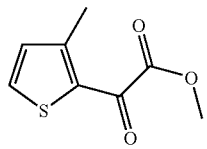

Aluminium trichloride (163 g, 1.222 mol) was initially charged in 540 ml of dichloromethane, the mixture was cooled to 0° C. and 112 ml (150 g, 1.222 mol) of methyl oxalyl chloride were added dropwise at this temperature. The mixture was then stirred at this temperature for another 10 min, also at 0° C., 3-methylthiophene was then added dropwise, and after warming to room temperature, the reaction mixture was stirred at this temperature overnight. The mixture was hydrolysed by pouring into 2 l of ice-water, and the organic phase was separated off, washed with sodium bicarbonate solution and dried over sodium sulphate giving, after removal of drying agent by filtration and concentration using a rotary evaporator, 119.5 g of methyl (3-methylthiophen-2-yl)oxoacetate. Yield: 57%. $^1$H-NMR (DMSO): δ=8.09 (d, 1H), 7.19 (d, 1H), 7.67 (dd, 1H), 3.90 (s, 3H), 2.49 (s, 3H).

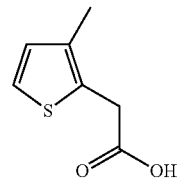

112.5 ml (116 g, 2.312 mol) of hydrazine hydrate were added slowly to a solution of 90 g (0.489 mol) of methyl (3-methylthiophen-2-yl)oxoacetate in 260 ml of diethylene glycol, and the mixture was heated at reflux for 30 min. After cooling to 30-40° C., 82 g (1.246 mol) of potassium hydroxide were added a little at a time, which was associated with a temperature increase to 70-80° C. with simultaneous evolution of nitrogen. The mixture was then slowly heated to reflux and stirred at this temperature for a total of 5 h. After cooling to room temperature, the mixture was poured into 2 l of water, adjusted to pH=1 using 250 ml of semiconcentrated hydrochloric acid and extracted with ethyl acetate. Drying of the organic phase over magnesium sulphate, filtration and removal of the solvent gave 50 g of (3-methylthiophen-2-yl) acetic acid. Yield: 66%. $^1$H-NMR (DMSO): δ=7.25 (d, 1H), 6.84 (d, 2H), 3.67 (s, 2H), 2.11 (s, 3H).

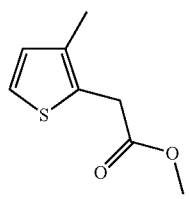

5 ml of concentrated sulphuric acid were added to a solution of 50 g (0.32 mol) of (3-methylthiophen-2-yl)acetic acid in 500 ml of methanol, and the mixture was heated at reflux for 8 h. The solvent was then removed using a rotary evaporator, and water and dichloromethane were added to the residue. Separation of the phases and re-extraction of the aqueous phase with dichloromethane gave, after drying of the organic phase over sodium sulphate, filtration and concentration using a rotary evaporator, 42.5 g of methyl (3-methylthiophen-2-yl)acetate. Yield: 70%. $^1$H-NMR (DMSO): δ=7.30 (d, 1H), 6.87 (d, 1H), 3.82 (s, 2H), 3.65 (s, 3H), 2.13 (s, 3H).

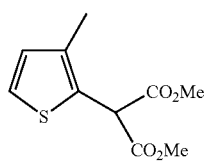

Under argon, 14.7 g of sodium hydride (60% in mineral oil) were added to 311 ml (332 g, 3.685 mol) of dimethyl carbonate, and the mixture was heated to 80° C. A solution of 41 g (0.217 mol) of methyl (3-methylthiophen-2-yl)acetate in 50 ml of toluene was slowly added dropwise at this temperature, and the mixture was stirred at reflux overnight. For work-up, the mixture was diluted with about 200 ml of methanol, poured into ice-water and acidified with dilute hydrochloric acid. Extraction with dichloromethane, drying of the organic phase over sodium sulphate, filtration and removal of the solvent gave 43.6 g of dimethyl 2-(3-methylthiophen-2-yl) malonate. Yield: 88%. $^1$H-NMR (DMSO): δ=7.42 (d, 1H), 6.89 (d, 1H), 5.27 (s, 1H), 3.69 (s, 6H), 2.15 (s, 3H).

Spectroscopic Data of the Analogously Prepared Intermediates:

| Structure | $^1$H-NMR (DMSO) |
|---|---|
| (3-chlorothiophen-2-yl methyl oxoacetate) | δ = 8.30 (d, 1H), 7.36 (d, 1H), 3.92 (s, 3H) |
| (3-chlorothiophen-2-yl acetic acid) | δ = 7.54 (d, 1H), 7.02 (d, 1H), 3.78 (s, 2H) |
| (methyl (3-chlorothiophen-2-yl)acetate) | δ = 7.57 (d, 1H), 7.04 (d, 1H), 3.90 (s, 2H), 3.66 (s, 3H) |
| (dimethyl 2-(3-chlorothiophen-2-yl)malonate) | δ = 7.71 (d, 1H), 7.08 (d, 1H), 5.25 (s, 1H), 3.73 (s, 6H) |
| (methyl (2-chlorothiophen-3-yl)acetate) | δ = 7.42 (d, 1H), 7.00 (d, 1H), 3.66 (s, 2H), 3.63 (s, 3H) |
| (dimethyl 2-(2-chlorothiophen-3-yl)malonate) | δ = 7.49 (d, 1H), 7.05 (d, 1H), 4.98 (s, 1H), 3.70 (s, 6H) |

USE EXAMPLES

Example A

*Podosphaera* Test (Apple)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

In this test, the compounds according to the invention of the example numbers below showed, at an active compound concentration of 100 ppm, an efficacy of 70% or more.

9, 15, 33, 38, 39, 45, 117, 123, 171, 183, 189, 207, 261, 285, 357, 441, 465, 519, 543, 549

Example B

*Venturia* Test (Apple)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

In this test, the compounds according to the invention of the example numbers below showed, at an active compound concentration of 100 ppm, an efficacy of 70% or more.

3, 9, 14, 15, 21, 33, 38, 39, 45, 117, 123, 171, 177, 183, 189, 201, 207, 213, 255, 261, 285, 345, 351, 357, 381, 435, 441, 459, 465, 507, 513, 519, 525, 543, 549, 1178

Example C

*Botrytis* Test (Bean)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized by *Botrytis cinerea* are placed onto each leaf. The inoculated plants are placed in a dark chamber at about 20° C. and 100% relative atmospheric humidity.

The size of the infected areas on the leaves is evaluated 2 days after the inoculation. 0% means an efficacy which corresponds to that of the control, whereas an efficacy of 100% means that no infection is observed.

In this test, the compounds according to the invention of the example numbers below showed, at an active compound concentration of 100 ppm, an efficacy of 70% or more.

3, 9, 14, 15, 21, 33, 38, 39, 45, 117, 123, 171, 177, 183, 189, 201, 207, 213, 255, 261, 285, 345, 351, 357, 381, 435, 441, 459, 465, 507, 513, 519, 525, 543, 549, 1178

Example D

*Sphaerotheca* Test (Cucumber)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young cucumber plants are sprayed with the preparation of active compound at the stated application rate. 1 day after the treatment, the plants are inoculated with a spore suspension of *Sphaerotheca fuliginea*. The plants are then placed in a greenhouse at 70% relative atmospheric humidity and a temperature of 23° C.

Evaluation is carried out 7 days after the inoculation. 0% means an efficacy which corresponds to that of the control, whereas an efficacy of 100% means that no infection is observed.

In this test, the compounds according to the invention of the formulae below show, at an active compound concentration of 500 ppm, an efficacy of 70% or more.

9, 14, 15, 33, 38, 123, 183, 351, 357, 429, 465

Example E

*Puccinia* Test (Wheat)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

In this test, the compounds according to the invention below show, at an active compound concentration of 1000 ppm, an efficacy of 70% or more.

3, 9, 15, 33, 45, 117, 123, 177, 201, 207, 255, 285, 345, 381, 435, 441, 465, 507, 513, 549

Example F

Compounds of the present invention were tested for a possible cytotoxic or proliferation-inhibiting activity on the human tumour cell lines HeLa, SW620 and A375 (all from ATCC, American Type Culture Collection). To this end, the cells were plated in microtitre plates from Greiner (manufacturer No. 781092) at a cell density of 1000 cells/microtitre plate well and cultivated in cell culture medium at 37° C. under a 5% carbon dioxide atmosphere. Cell culture media and additives were purchased from Invitrogen and the foetal calf serum from Biochrom. The cell culture media for HeLa and A375 cells were used as stated by ATCC (HeLa: MEM, order No. 10370-047, with 1% sodium bicarbonate, 1% nonessential amino acids, 1% sodium pyruvate, 10% foetal calf serum, 0.1% gentamycin; A375: DMEM, order No. 41965-039, 2% sodium bicarbonate, 1% L-Glutamax, 10% foetal calf serum, 0.1% gentamycin). The culture medium for the SW620 cells consisted of DMEM, order No. 41965-039, 1% non-essential amino acids, 10% foetal calf serum, 0.1% gentamycin.

24 hours after the cells had been plated in the microtitre plates, various concentrations of at most 100 μM down to a minimum concentration of 5 nM of the test compounds were added to the cells. Stock solutions of the test compounds (10 mM) were prepared in DMSO and stored at −20° C. For the cytotoxicity tests, the test compounds were diluted in the appropriate cell culture medium.

After a further 48 hours of incubation, the cells were washed with medium and analysed with the aid of a two-colour fluorescence cytotoxicity/viability test (LIVE/DEAD Viability/Cytotoxicity ASSAY Kit from Molecular Probes, order No. L-3224), according to the instructions of the manufacturer. To this end, the medium was aspirated and in each case 30 μl of LIVE/DEAD reagent per microtitre plate well were added to the cells, which were then incubated for 30 minutes. The cells were then washed with PBS (phosphate-buffered saline). The number of live cells was analysed by measuring the green fluorescence of the live dye calcein-AM as a component of the LIVE/DEAD reagent using a fluorescence plate reader (Flexstation, from Molecular Devices) at an excitation wavelength of 485 nM and an emission wavelength of 525 nM (Oral et al. 1998). Cells only with cell culture medium, without added test compounds, were treated in parallel and analysed as growth controls. The reference compounds used for anti-tumour agents having a cytotoxic or proliferation-inhibiting action were colchicine (from Merck/Calbiochem, order No 234115) and Taxol (baccatin III N-benzyl-b-phenylisoserine ester, from Merck/Calbiochem, order No. 580555) (Schiff and Horwitz 1980; Holmes et al., 1991). The cytotoxic effects of the test compounds were expressed as logarithmic $GI_{50}$ values ((growth)-inhibiting logarithmic concentration value at which a cell growth reduced by 50% compared to the control without test compounds was measured; Xia et al., 2001; Smith et al., 2005).

TABLE 2

Inhibition of the cell proliferation in the presence of test compounds according to the LIVE/DEAD cytotoxicity assay protocol on different human tumour cell lines, log $GI_{50}$ values (M)

| Example No. | | A375 cells | SW620 cells | HeLa cells |
|---|---|---|---|---|
| | colchicine | 7.7 | 7.5 | 7.8 |
| | Taxol | 6.7 | 6.9 | 7.8 |
| 177 | | 8.1 | 6.7 | >8 |
| 117 | | 6.6 | 6.6 | 6.8 |
| 345 | | 6.3 | 6.4 | 6.6 |

Alternatively to the cell growth analysis in microtitre plates, the different cells were also cultivated on slides and incubated analogously with the test compounds. As described, the cells were treated with the reagents from the LIVE/DEAD Assay Kit according to the instructions of the manufacturer and then studied using a fluorescence microscope.

The invention claimed is:

1. A compound of formula (I)

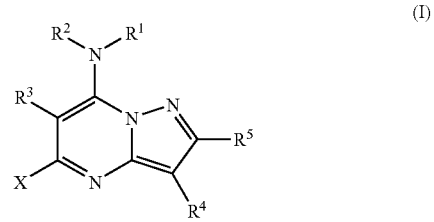

in which the symbols are as defined below $R^1$ represents hydrogen, alkyl having 1 to 10 carbon atoms which is unsubstituted or mono- to pentasubstituted by identical or different substituents selected from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, and mono- or dialkylamino having in each case 1 to 4 carbon atoms, or $R^1$ represents alkenyl having 2 to 10 carbon atoms which is unsubstituted or mono- to trisubstituted by identical or different substituents selected from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, and mono- or dialkylamino having in each case 1 to 4 carbon atoms, or $R^1$ represents alkynyl having 2 to 10 carbon atoms which is unsubstituted or mono- to trisubstituted by identical or different substituents selected from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, and mono- or dialkylamino having in each case 1 to 4 carbon atoms, or $R^1$ represents cycloalkyl having 3 to 10 carbon atoms which is unsubstituted or mono- to trisubstituted by identical or different substituents selected from the group consisting of halogen and alkyl having 1 to 4 carbon atoms, or $R^1$ represents saturated or unsaturated heterocyclyl having 3 to 10 ring members and 1 to 3 heteroatoms, such as nitrogen, oxygen or sulphur, where the heterocyclyl is unsubstituted or mono- or polysubstituted by halogen, alkyl having 1 to 4 carbon atoms, cyano, nitro, cycloalkyl having 3 to 6 carbon atoms, hydroxyl, alkoxy having 1 to 4 carbon atoms or mercapto;

$R^2$ represents hydrogen or alkyl having 1 to 6 carbon atoms;

$R^1$ and $R^2$ together with the nitrogen atom to which they are attached represent a saturated or unsaturated heterocyclic ring having 3 to 8 ring members, where the heterocycle optionally contains a further nitrogen, oxygen or sulphur atom as ring member and where the heterocycle may be unsubstituted or mono- to trisubstituted by fluorine, chlorine, bromine, alkyl having 1 to 4 carbon atoms, haloalkyl having 1 to 4 carbon atoms and 1 to 9 fluorine or chlorine atoms, hydroxyl, alkoxy having 1 to 4 carbon atoms, haloalkoxy having 1 to 4 carbon atoms and 1 to 9 fluorine or chlorine atoms, mercapto, thioalkyl having 1 to 4 carbon atoms or haloalkylthio having 1 to 4 carbon atoms and 1 to 9 fluorine or chlorine atoms;

$R^3$ represents $C_1$-$C_{10}$-alkyl, $C_2$-$C_{10}$-alkenyl, $C_2$-$C_{10}$-alkynyl, $C_3$-$C_8$-cycloalkyl, phenyl-$C_1$-$C_{10}$-alkyl, where $R^3$ is unsubstituted or partially or fully halogenated or optionally carries one to three radicals from the group $R^x$, or $C_1$-$C_{10}$-haloalkyl which optionally carries one to three radicals from the group $R^x$, and $R^x$ represents cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy, or $R^3$ represents phenyl which may be mono- to tetrasubstituted by identical or different substituents selected from the group consisting of halogen, cyano, nitro, amino, hydroxyl, formyl, carboxyl, carboxyalkyl, carbamoyl, and thiocarbamoyl;

in each case straight-chain or branched alkyl, alkoxy, alkylthio, alkyl-sulphinyl or alkylsulphonyl having in each case 1 to 6 carbon atoms;

in each case straight-chain or branched alkenyl or alkenyloxy having in each case 2 to 6 carbon atoms;

in each case straight-chain or branched haloalkyl, haloalkoxy, haloalkylthio, haloalkylsulphinyl or haloalkylsulphonyl having in each case 1 to 6 carbon atoms and 1 to 13 identical or different halogen atoms;

in each case straight-chain or branched haloalkenyl or haloalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;

cycloalkyl having 3 to 8 carbon atoms;

2,3-attached 1,3-propanediyl, 1,4-butanediyl, methylenedioxy (—O—CH$_2$—O—) or 1,2-ethylenedioxy (—O—CH$_2$—CH$_2$—O—), where these radicals may be mono- or polysubstituted by identical or different substituents selected from the group consisting of halogen, alkyl having 1 to 4 carbon atoms and haloalkyl having 1 to 4 carbon atoms and 1 to 9 identical or different halogen atoms;

or $R^3$ represents saturated or fully or partially unsaturated or aromatic heterocyclyl having 3 to 8 ring members and 1 to 3 heteroatoms selected from the group consisting of nitrogen, oxygen and sulphur, where the heterocyclyl may be mono- or disubstituted by halogen, alkyl having 1 to 4 carbon atoms, alkoxy having 1 to 4 carbon atoms, alkylthio having 1 to 4 carbon atoms, haloalkoxy having 1 to 4 carbon atoms, haloalkylthio having 1 to 4 carbon atoms, hydroxyl, mercapto, cyano, nitro or cycloalkyl having 3 to 6 carbon atoms or carboxyalkyl;

$R^3$ represents $C_1$-$C_8$-alkylamino, $C_2$-$C_8$alkenylamino, $C_2$-$C_8$alkynylamino, di-$C_1$-$C_8$-alkylamino, di-$C_2$-$C_8$-alkenylamino, di-$C_2$-$C_8$-alkynylamino, $C_2$-$C_8$-alkenyl-($C_2$-$C_8$)-alkynylamino, $C_2$-$C_6$-alkynyl-($C_1$-$C_8$)-alkylamino, $C_2$-$C_8$-alkenyl-($C_1$-$C_8$)-alkylamino, $C_6$-$C_{10}$-arylamino, $C_6$-$C_{10}$-aryl-($C_1$-$C_8$)-alkylamino, $C_6$-$C_{10}$-aryl-($C_1$-$C_4$)-alkyl-($C_1$-$C_8$)-alkylamino, heterocyclyl-($C_1$-$C_8$)-alkylamino or heterocyclyl-($C_1$-$C_4$)-alkyl-($C_1$-$C_8$)-alkylamino;

$R^4$ represents CONR$^6$R$^7$;

$R^5$ represents H, halogen, ($C_1$-$C_4$)-alkyl which is unsubstituted or substituted by one or more halogen atoms, cyclopropyl which is unsubstituted or substituted by one or more halogen atoms; SCH$_3$, SOCH$_3$, SO$_2$CH$_3$ or OCH$_3$;

X represents H, fluorine, chlorine, bromine, CN, hydroxyl, alkoxy having 1 to 4 carbon atoms or alkylthio having 1 to 4 carbon atoms;

$R^6$ represents H, an alkali metal or alkaline earth metal, copper, NH$_4$, mono-($C_1$-$C_{10}$)-alkylammonium, di-($C_1$-$C_{10}$)-alkylammonium, tri-($C_1$-$C_{10}$)-alkylammonium, tetra-($C_1$-$C_{10}$)-alkylammonium, where the alkyl radicals of the ammonium ions may be substituted by aryl or hydroxyl, cholinium, $C_1$-$C_{10}$-alkyl, $C_2$-$C_{10}$-alkenyl, $C_2$-$C_{10}$-alkynyl, $C_3$-$C_8$-cycloalkyl, $C_3$-$C_8$-cycloalkenyl, aryl, phenyl-$C_1$-$C_{10}$-alkyl, where $R^6$ is unsubstituted or partially or fully halogenated or optionally carries one to three radicals from the group $R^x$, or $C_1$-$C_{10}$-haloalkyl which optionally carries one to three radicals from the group $R^x$, and $R^x$ represents cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy or CONR$^6$R$^7$, CONR$^7$OR$^7$, COOR$^8$, carboxy-($C_1$-$C_4$)-alkyl;

$R^7$ represents COR$^S$, S(O)$_{1-2}$R$^8$, cyano, COOR$^8$, CON(R$^8$)$_2$, or

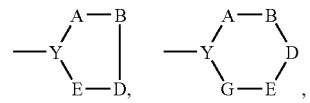

A, B, D, E, G are identical or different and are CR$^9$, CR$^9$R$^9$, N, NR$^9$, O or S, with the proviso that at least one symbol represents N, O or S and that the oxygen atoms are not adjacent to one another;

Y represents C, CR$^9$ or N;

$R^8$ represents H, $C_1$-$C_{10}$-alkyl, $C_2$-$C_{10}$-alkenyl, $C_2$-$C_{10}$-alkynyl, $C_3$-$C_8$-cycloalkyl, $C_3$-$C_8$-cycloalkenyl, aryl, phenyl-$C_1$-$C_{10}$-alkyl, where $R^8$ is unsubstituted or partially or fully halogenated or optionally carries one to three radicals selected from the group consisting of $R^x$, or $C_1$-$C_{10}$-haloalkyl which optionally carries one to three radicals from the group $R^x$, and $R^x$ represents cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy; or two radicals $R^8$ form a cycle having 3 to 6 carbon atoms which is saturated or partially unsaturated and optionally contains 1 or 2 further N, S or O atoms, where the oxygen atoms are not adjacent to one another;

or $R^6$ and $R^8$ together with the N—CO or N—S(O)$_{1-2}$ group to which they are attached form a 4- to 8-membered cycle which may contain one or more heteroatoms selected from the group consisting of sulphur, oxygen and nitrogen, where oxygen atoms are not adjacent to one another;

$R^9$ represents $R^7$, halogen, $NR^7{}_2$, OH, $SR^7$ or $OR^7$, or an agrochemically active salt thereof.

2. A compound of formula (I) according to claim 1, in which the symbols are as defined below

- $R^1$ represents hydrogen, alkyl having 1 to 10 carbon atoms which is unsubstituted or mono- to pentasubstituted by identical or different substituents selected from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, and mono- or dialkylamino having in each case 1 to 4 carbon atoms, or
- $R^1$ represents alkenyl having 2 to 10 carbon atoms which is unsubstituted or mono- to trisubstituted by identical or different substituents selected from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, and mono- or dialkylamino having in each case 1 to 4 carbon atoms, or
- $R^1$ represents alkynyl having 2 to 10 carbon atoms which is unsubstituted or mono- to trisubstituted by identical or different substituents selected from the group consisting of halogen, cyano, hydroxyl, alkoxy having 1 to 4 carbon atoms, cycloalkyl having 3 to 6 carbon atoms, mercapto, alkylthio having 1 to 4 carbon atoms, amino, and mono- or dialkylamino having in each case 1 to 4 carbon atoms, or
- $R^1$ represents cycloalkyl having 3 to 10 carbon atoms which is unsubstituted or mono- to trisubstituted by identical or different substituents selected from the group consisting of halogen and alkyl having 1 to 4 carbon atoms, or
- $R^1$ represents saturated or unsaturated heterocyclyl having 3 to 10 ring members and 1 to 3 heteroatoms, such as nitrogen, oxygen or sulphur, where the heterocyclyl is unsubstituted or mono- or polysubstituted by halogen, alkyl having 1 to 4 carbon atoms, cyano, nitro, cycloalkyl having 3 to 6 carbon atoms, hydroxyl, alkoxy having 1 to 4 carbon atoms or mercapto;
- $R^2$ represents hydrogen or alkyl having 1 to 6 carbon atoms;
- $R^1$ and $R^2$ together with the nitrogen atom to which they are attached represent a saturated or unsaturated heterocyclic ring having 3 to 8 ring members, where the heterocycle optionally contains a further nitrogen, oxygen or sulphur atom as ring member and where the heterocycle may be unsubstituted or mono- to trisubstituted by fluorine, chlorine, bromine, alkyl having 1 to 4 carbon atoms, haloalkyl having 1 to 4 carbon atoms and 1 to 9 fluorine or chlorine atoms, hydroxyl, alkoxy having 1 to 4 carbon atoms, haloalkoxy having 1 to 4 carbon atoms and 1 to 9 fluorine or chlorine atoms, mercapto, thioalkyl having 1 to 4 carbon atoms or haloalkylthio having 1 to 4 carbon atoms and 1 to 9 fluorine or chlorine atoms;
- $R^3$ represents $C_1$-$C_{10}$-alkyl, $C_2$-$C_{10}$-alkenyl, $C_2$-$C_{10}$-alkynyl, $C_3$-$C_8$-cycloalkyl, phenyl-$C_1$-$C_{10}$-alkyl, where $R^3$ is unsubstituted or partially or fully halogenated or optionally carries one to three radicals from the group $R^x$, or $C_1$-$C_{10}$-haloalkyl which optionally carries one to three radicals from the group $R^x$, and $R^x$ represents cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy, or
- $R^3$ represents phenyl which may be mono- to tetrasubstituted by identical or different substituents selected from the group consisting of
  - halogen, cyano, nitro, amino, hydroxyl, formyl, carboxyl, carboxyalkyl, carbamoyl, thiocarbamoyl;
  - in each case straight-chain or branched alkyl, alkoxy, alkylthio, alkyl-sulphinyl or alkylsulphonyl having in each case 1 to 6 carbon atoms;
  - in each case straight-chain or branched alkenyl or alkenyloxy having in each case 2 to 6 carbon atoms;
  - in each case straight-chain or branched haloalkyl, haloalkoxy, haloalkylthio, haloalkylsulphinyl or haloalkylsulphonyl having in each case 1 to 6 carbon atoms and 1 to 13 identical or different halogen atoms;
  - in each case straight-chain or branched haloalkenyl or haloalkenyloxy having in each case 2 to 6 carbon atoms and 1 to 11 identical or different halogen atoms;
  - in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;
  - cycloalkyl having 3 to 8 carbon atoms; and
  - 2,3-attached 1,3-propanediyl, 1,4-butanediyl, methylenedioxy (—O—CH$_2$—O—) or 1,2-ethylenedioxy (—O—CH$_2$—CH$_2$—O—), where these radicals are optionally mono- or polysubstituted by identical or different substituents selected from the group consisting of halogen, alkyl having 1 to 4 carbon atoms and haloalkyl having 1 to 4 carbon atoms and 1 to 9 identical or different halogen atoms;

or

- $R^3$ represents saturated or fully or partially unsaturated or aromatic heterocyclyl having 3 to 8 ring members and 1 to 3 heteroatoms selected from the group consisting of nitrogen, oxygen and sulphur, where the heterocyclyl may be mono- or disubstituted by halogen, alkyl having 1 to 4 carbon atoms, alkoxy having 1 to 4 carbon atoms, alkylthio having 1 to 4 carbon atoms, haloalkoxy having 1 to 4 carbon atoms, haloalkylthio having 1 to 4 carbon atoms, hydroxyl, mercapto, cyano, nitro or cycloalkyl having 3 to 6 carbon atoms or carboxyalkyl;
- $R^3$ represents $C_1$-$C_8$-alkylamino, $C_2$-$C_8$alkenylamino, $C_2$-$C_8$-alkynylamino, di-$C_1$-$C_8$-alkylamino, di-$C_2$-$C_8$-alkenylamino, di-$C_2$-$C_8$-alkynylamino, $C_2$-$C_8$-alkenyl-($C_2$-$C_8$)-alkynylamino, $C_2$-$C_6$-alkynyl-($C_1$-$C_8$)-alkylamino, $C_2$-$C_8$-alkenyl-($C_1$-$C_8$)-alkylamino, $C_6$-$C_{10}$-arylamino, $C_6$-$C_{10}$-aryl-($C_1$-$C_8$)-alkylamino, $C_6$-$C_{10}$-aryl-($C_1$-$C_4$)-alkyl-($C_1$-$C_8$)-alkylamino, heterocyclyl-($C_1$-$C_8$)-alkylamino or heterocyclyl-($C_1$-$C_4$)-alkyl-($C_1$-$C_8$)-alkylamino;
- $R^4$ represents $CONR^6R^7$;
- $R^5$ represents H, halogen, ($C_1$-$C_4$)-alkyl which is unsubstituted or substituted by one or more halogen atoms, cyclopropyl which is unsubstituted or substituted by one or more halogen atoms; $SCH_3$, $SOCH_3$, $SO_2CH_3$ or $OCH_3$;

X represents H, fluorine, chlorine, bromine, CN, hydroxyl, alkoxy having 1 to 4 carbon atoms, alkylthio having 1 to 4 carbon atoms or $(C_1$-$C_7)$-alkyl or $(C_1$-$C_3)$-haloalkyl;

$R^6$ represents H, an alkali metal or alkaline earth metal, copper, $NH_4$, mono-$(C_1$-$C_{10})$-alkylammonium, di-$(C_1$-$C_{10})$-alkylammonium, tri-$(C_1$-$C_{10})$-alkylammonium, tetra-$(C_1$-$C_{10})$-alkylammonium, where the alkyl radicals of the ammonium ions may be substituted by aryl or hydroxyl, cholinium, $C_1$-$C_{10}$-alkyl, $C_2$-$C_{10}$-alkenyl, $C_2$-$C_{10}$-alkynyl, $C_3$-$C_8$-cycloalkyl, $C_3$-$C_8$-cycloalkenyl, aryl, phenyl-$C_1$-$C_{10}$-alkyl, where $R^6$ is unsubstituted or partially or fully halogenated or optionally carries one to three radicals from the group $R^x$, or $C_1$-$C_{10}$-haloalkyl which optionally carries one to three radicals from the group $R^x$, and $R^x$ represents cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy or $CONR^6R^7$, $CONR^7OR^7$, $COOR^8$, carboxy-$(C_1$-$C_4)$-alkyl;

$R^7$ represents $COR^8$, $S(O)_{1-2}R^8$, cyano, $COOR^8$, $CON(R^8)_2$, where the radicals $R^8$ may be identical or different, or

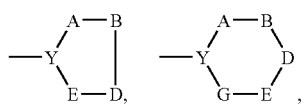

A, B, D, E, G are identical or different and are $CR^9$, $CR^9R^9$, N, $NR^9$, O or S, with the proviso that at least one symbol represents N, O or S and that the oxygen atoms are not adjacent to one another;

Y represents C, $CR^9$ or N;

$R^8$ independently of the other radicals represents H, $C_1$-$C_{10}$-alkyl, $C_2$-$C_{10}$-alkenyl, $C_2$-$C_{10}$-alkynyl, $C_3$-$C_8$-cycloalkyl, $C_3$-$C_8$-cycloalkenyl, aryl, phenyl-$C_1$-$C_{10}$-alkyl, where $R^8$ is unsubstituted or partially or fully halogenated or optionally carries one to three radicals from the group $R^x$, or $C_1$-$C_{10}$-haloalkyl which optionally carries one to three radicals selected from the group consisting of $R^x$, and $R^x$ represents cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and optionally halogenated oxy-$C_1$-$C_4$-alkyl-$C_1$-$C_4$-alkenoxy, oxy-$C_1$-$C_4$-alkenyl-$C_1$-$C_4$-alkoxy, oxy-$C_1$-$C_4$-alkyl-$C_1$-$C_4$-alkyloxy; or two radicals $R^8$ form a cycle having 3 to 6 carbon atoms which is saturated or partially unsaturated and optionally contains 1 or 2 further N, S or O atoms, where the oxygen atoms are not adjacent to one another;

or $R^6$ and $R^8$ together with the N—CO or N—$S(O)_{1-2}$ group to which they are attached form a 4- to 8-membered cycle which may contain one or more heteroatoms selected from the group consisting of sulphur, oxygen and nitrogen, where oxygen atoms are not adjacent to one another;

$R^9$ represents $R^7$, H, halogen, $NR^7_2$, OH, $SR^7$ or $OR^7$.

3. A compound of formula (I) according to claim 1 in which the symbols are as defined below $R^1$ represents hydrogen or a radical of the formula

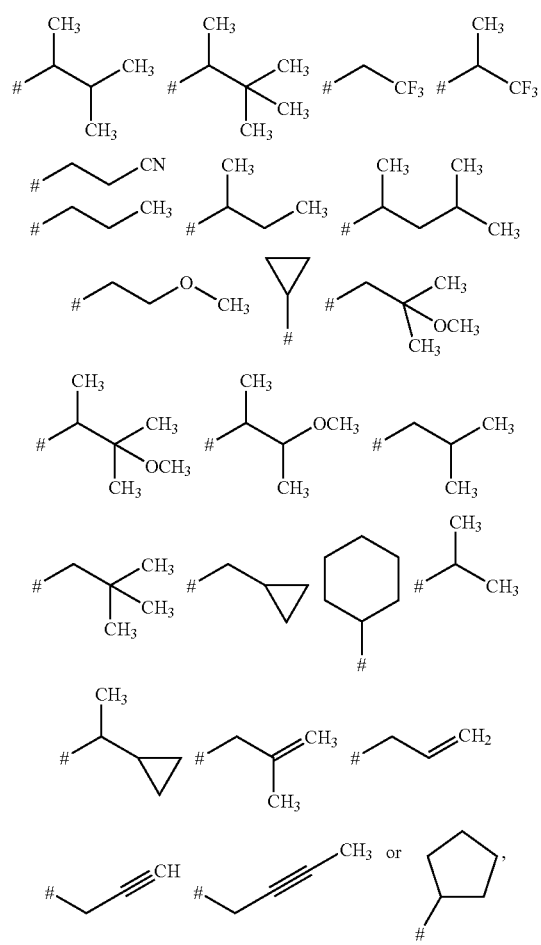

where # denotes the point of attachment and the radicals may be present in optically pure form or as isomer mixtures;

$R^2$ represents hydrogen, methyl, ethyl, propyl, or $R^1$ and $R^2$ together with the nitrogen atom to which they are attached represent pyrrolidinyl, piperidinyl, morpholinyl, thiomorpholinyl, piperazinyl, 3,6-dihydro-1(2H)-pyridinyl or tetrahydro-1(2H)-pyridazinyl, where these radicals are unsubstituted or substituted by 1 to 3 fluorine atoms, 1 to 3 methyl groups or trifluoromethyl, or $R^1$ and $R^2$ together with the nitrogen atom to which they are attached represent a radical of the formula

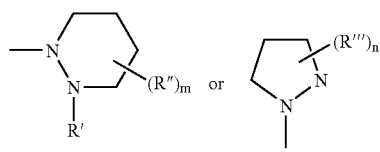

in which
R' represents hydrogen or methyl,
R'' represents methyl, ethyl, fluorine, chlorine or trifluoromethyl,
m represents the number 0, 1, 2 or 3, where R'' represents identical or different radicals if m represents 2 or 3,
R''' represents methyl, ethyl, fluorine, chlorine or trifluoromethyl
and
n represents the number 0, 1, 2 or 3, where R''' represents identical or different radicals if n represents 2 or 3,
$R^3$ represents $(C_1-C_8)$-alkyl, $(C_3-C_8)$-cycloalkyl, where $R^3$ is unsubstituted or substituted by one or more fluorine or chlorine atoms, benzyl or
$R^3$ represents phenyl which may be mono- to trisubstituted by identical or different substituents selected from the group consisting of
  fluorine, chlorine, bromine, cyano, nitro, formyl, methyl, ethyl, n- or i-propyl, n-, s- or t-butyl, vinyl, ethynyl, allyl, propargyl, methoxy, ethoxy, n- or i-propoxy, methylthio, ethylthio, n- or i-propylthio, methylsulphinyl, ethylsulphinyl, methylsulphonyl, ethylsulphonyl, allyloxy, propargyloxy, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, trichloroethynyloxy, trifluoroethynyloxy, chloro-allyloxy, iodopropargyloxy, methylamino, ethylamino, n- or i-propylamino, dimethylamino, diethylamino, acetyl, propionyl, acetyloxy, methoxycarbonyl, ethoxycarbonyl, hydroximinomethyl, hydroximinoethyl, methoximinomethyl, ethoximinomethyl, methoximinoethyl, ethoximinoethyl, cyclopropyl, cyclobutyl, cyclopentyl and cyclohexyl, or by
  2,3-attached 1,3-propanediyl, 1,4-butanediyl, methylenedioxy (—O—CH$_2$—O—) or 1,2-ethylenedioxy (—O—CH$_2$—CH$_2$—O—), where these radicals may be mono- or polysubstituted by identical or different substituents selected from the group consisting of fluorine, chlorine, methyl, ethyl, n-propyl, i-propyl, trifluoromethyl, carboxyl and carboxymethyl,
$R^3$ represents pyridyl which is attached in the 2- or 4-position and may be mono- to tetrasubstituted by identical or different substituents from the group consisting of fluorine, chlorine, bromine, cyano, hydroxyl, mercapto, nitro, methyl, ethyl, methoxy, methylthio, hydroximinomethyl, hydroximinoethyl, methoximinomethyl, methoximinoethyl, trifluoromethyl, carboxyl and carboxymethyl or
$R^3$ represents pyrimidyl which is attached in the 2- or 4-position and may be mono- to trisubstituted by identical or different substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or $R^3$ represents thienyl which is attached in the 2- or 3-position and may be mono- to trisubstituted by identical or different substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or $R^3$ represents $C_1-C_8$-alkylamino or di-$C_1-C_8$-alkylamino, or $R^3$ represents thiazolyl which is attached in the 2-, 4- or 5-position and may be mono- or disubstituted by identical or different substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or $R^3$ represents N-piperidinyl, N-tetrazolyl, N-pyrazolyl, N-imidazolyl, N-1,2,4-triazolyl, N-pyrrolyl or N-morpholinyl which are in each case unsubstituted or mono- or polysubstituted by identical or different substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl and trifluoromethyl, $R^4$ represents $CONR^6R^7$;

$R^5$ represents H, Cl, F, CH$_3$, —CH(CH$_3$)$_2$ or cyclopropyl; X represents H, F, Cl, CN, $C_1-C_4$-alkyl which is unsubstituted or substituted by one or more fluorine or chlorine atoms;

$R^6$ represents H, Na, K, ½Ca, ½Mg, Cu, NH$_4$, NH(CH$_3$)$_3$, N(CH$_3$)$_4$, HN(C$_2$H$_5$)$_3$, N(C$_2$H$_5$)$_4$, H$_2$N(iC$_3$H$_7$)$_2$, H$_3$NCH$_2$Ph, (H$_3$C)$_3$NCH$_2$Ph, cholinium, (C$_1$-C$_8$)-alkyl, (C$_3$-C$_6$)-alkenyl, (C$_3$-C$_8$)-cycloalkenyl, (C$_3$-C$_8$)-cycloalkyl, phenyl, benzyl;

$R^7$ represents $COR^8$, $S(O)_{1-2}R^8$, cyano, $COOR^8$, $CON(R^8)_2$, pyrrolyl, imidazolyl, pyrazolyl, 1,3,4-triazolyl, thiazolyl, isothiazolyl, 1,3,4-oxadiazolyl, 1,3,4-thiadiazolyl, oxazolyl, isoxazolyl, tetrazolyl, oxadiazinyl, 4H-[1,2,4]-oxadiazin-3-yl, dioxazinyl, 5,6-dihydro-[1,4,2]-dioxazin-3-yl, pyridyl, pyrimidinyl, pyrazinyl, pyridazinyl, where the heterocyclic radicals are optionally substituted by one or more radicals selected from the group consisting of $C_1-C_4$-alkyl, $C_1-C_4$-alkoxy and halogen;

$R^8$ represents H, $(C_1-C_8)$-alkyl, $(C_3-C_6)$-alkenyl, propargyl, $(C_3-C_8)$-cycloalkyl, benzyl; or two radicals $R^8$ form a cycle having 3 to 6 carbon atoms which is saturated or partially unsaturated and optionally contains 1 or 2 further N, S or O atoms, where the oxygen atoms are not adjacent;
or $R^6$ and $R^8$ together with the N—CO or N—S(O)$_{1-2}$ group to which they are attached form a 4- to 8-membered cycle which may contain one or more heteroatoms selected from the group consisting of sulphur, oxygen and nitrogen, where oxygen atoms are not adjacent.

4. A compound of formula (I) according to claim 1 in which the symbols are as defined below R¹ represents hydrogen or a radical of the formula

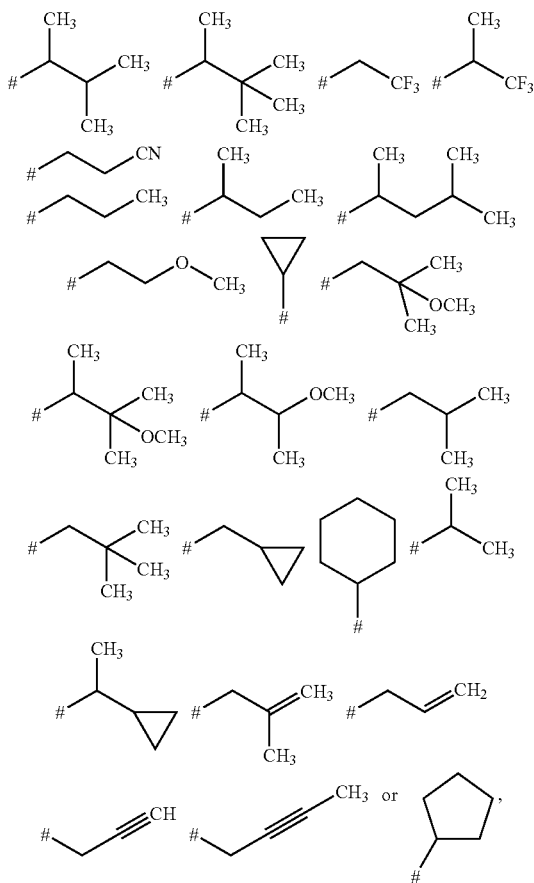

where # denotes the point of attachment where the radicals may be present in optically pure form or as isomer mixtures;

R² represents hydrogen, methyl, ethyl, propyl, or

R¹ and R² together with the nitrogen atom to which they are attached represent pyrrolidinyl, piperidinyl, morpholinyl, thiomorpholinyl, piperazinyl, 3,6-dihydro-1(2H)-pyridinyl or tetrahydro-1(2H)-pyridazinyl, where these radicals are unsubstituted or substituted by 1 to 3 fluorine atoms, 1 to 3 methyl groups or trifluoromethyl, or R¹ and R² together with the nitrogen atom to which they are attached represent a radical of the formula

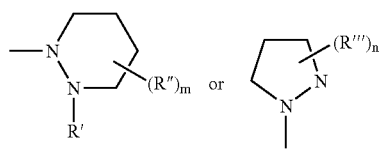

in which

R' represents hydrogen or methyl,

R″ represents methyl, ethyl, fluorine, chlorine or trifluoromethyl, m represents the number 0, 1, 2 or 3, where R″ represents identical or different radicals if m represents 2 or 3, R‴ represents methyl, ethyl, fluorine, chlorine or trifluoromethyl and n represents the number 0, 1, 2 or 3, where R‴ represents identical or different radicals if n represents 2 or 3, R³ represents ($C_1$-$C_6$)-alkyl, ($C_3$-$C_6$)-alkenyl, ($C_3$-$C_6$)-alkynyl, ($C_3$-$C_8$)-cycloalkyl or benzyl, where R³ is unsubstituted or substituted by one or more fluorine or chlorine atoms or alkyl, or R³ represents phenyl which may be mono- to trisubstituted by identical or different substituents selected from the group consisting of fluorine, chlorine, bromine, cyano, nitro, formyl, methyl, ethyl, n- or i-propyl, n-, i-, s- or t-butyl, vinyl, ethynyl, allyl, propargyl, methoxy, ethoxy, n- or i-propoxy, methylthio, ethylthio, n- or i-propylthio, methylsulphinyl, ethylsulphinyl, methylsulphonyl, ethylsulphonyl, allyloxy, propargyloxy, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, trichloroethynyloxy, trifluoroethynyloxy, chloro-allyloxy, iodopropargyloxy, methylamino, ethylamino, n- or i-propylamino, dimethylamino, diethylamino, acetyl, propionyl, acetyloxy, methoxycarbonyl, ethoxycarbonyl, hydroximinomethyl, hydroximinoethyl, methoximinomethyl, ethoximinomethyl, methoximinoethyl, ethoximinoethyl, cyclopropyl, cyclobutyl, cyclopentyl and cyclohexyl, or by 2,3-attached 1,3-propanediyl, 1,4-butanediyl, methylenedioxy (—O—$CH_2$—O—) or 1,2-ethylenedioxy (—O—$CH_2$—$CH_2$—O—), where these radicals may be mono- or polysubstituted by identical or different substituents selected from the group consisting of fluorine, chlorine, methyl, ethyl, n-propyl, i-propyl, trifluoromethyl, carboxyl and carboxymethyl, R³ represents pyridyl which is attached in the 2- or 4-position and may be mono- to tetrasubstituted by identical or different substituents selected from the group consisting of fluorine, chlorine, bromine, cyano, hydroxyl, mercapto, nitro, methyl, ethyl, methoxy, methylthio, hydroximinomethyl, hydroximinoethyl, methoximinomethyl, methoximinoethyl, trifluoromethyl, carboxyl and carboxymethyl or R³ represents pyrimidyl which is attached in the 2- or 4-position and may be mono- to trisubstituted by identical or different substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or R³ represents thienyl which is attached in the 2- or 3-position and may be mono- to trisubstituted by identical or different substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or R³ represents $C_1$-$C_8$-alkylamino or di-$C_1$-$C_8$-alkylamino, or R³ represents thiazolyl which is attached in the 2-, 4- or 5-position and may be mono- or disubstituted by identical or different substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or $R^3$ represents N-piperidinyl, N-tetrazolyl, N-pyrazolyl, N-imidazolyl, N-1,2,4-triazolyl, N-pyrrolyl or N-morpholinyl which are in each case unsubstituted or mono- or polysubstituted by identical or different substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl and trifluoromethyl, $R^4$ represents $CONR^6R^7$;

$R^5$ represents H, Cl, F, $CH_3$, —$CH(CH_3)_2$ or cyclopropyl; X represents H, F, Cl, CN, $C_1$-$C_4$-alkyl which is unsubstituted or substituted by one or more fluorine or chlorine atoms;

$R^6$ represents H, Na, K, ½Ca, ½Mg, Cu, $NH_4$, $NH(CH_3)_3$, $N(CH_3)_4$, $HN(C_2H_5)_3$, $N(C_2H_5)_4$, $H_2N(iC_3H_7)_2$, $H_3NCH_2Ph$, $(H_3C)_3NCH_2Ph$, cholinium, ($C_1$-$C_8$)-alkyl, ($C_3$-$C_6$)-alkenyl, ($C_3$-$C_8$)-cycloalkenyl, ($C_3$-$C_8$)-cycloalkyl, phenyl, benzyl;

$R^7$ represents $COR^8$, $S(O)_{1-2}R^8$, cyano, $COOR^8$, $CON(R^8)_2$, pyrrolyl, imidazolyl, pyrazolyl, 1,3,4-triazolyl, thiazolyl, isothiazolyl, 1,3,4-oxadiazolyl, 1,3,4-thiadiazolyl, oxazolyl, isoxazolyl, tetrazolyl, oxadiazinyl, 4H-[1,2,4]-oxadiazin-3-yl, dioxazinyl, 5,6-dihydro-[1,4,2]-dioxazin-3-yl, pyridyl, pyrimidinyl, pyrazinyl, pyridazinyl, where the heterocyclic radicals are optionally substituted by one or more radicals selected from the group consisting of $C_1$-$C_4$-alkyl, $C_1$-$C_4$-alkoxy and halogen;

$R^8$ represents H, ($C_1$-$C_8$)-alkyl, ($C_1$-$C_8$)-haloalkyl, ($C_3$-$C_6$)-alkenyl, propargyl, ($C_3$-$C_8$)-cycloalkyl, benzyl; or two radicals $R^8$ form a cycle having 3 to 6 carbon atoms which is saturated or partially unsaturated and optionally contains 1 or 2 further N, S or O atoms, where oxygen atoms are not adjacent to one another;

Or $R^6$ and $R^8$ together with the N—CO or N—$S(O)_{1-2}$ group to which they are attached form a 4- to 8-membered cycle which may contain one or more heteroatoms selected from the group consisting of sulphur, oxygen and nitrogen, where oxygen atoms are not adjacent to one another.

5. A compound of formula (I) according to claim 1, where the symbols are as defined below $R^3$ represents ($C_1$-$C_6$)-alkyl, ($C_3$-$C_6$)-alkenyl, ($C_3$-$C_6$)-alkynyl, ($C_3$-$C_8$)-cycloalkyl, where $R^3$ is unsubstituted or substituted by one or more fluorine or chlorine atoms or alkyl, or $R^3$ represents 2,4-, 2,5- or 2,6-disubstituted phenyl, or 2-substituted phenyl or represents 2,4,6- or 2,4,5-trisubstituted phenyl having substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, carboxyl and carboxymethyl or $R^3$ represents pyridyl which is attached in the 2- or 4-position and may be mono- to tetrasubstituted by identical or different substituents selected from the group consisting of fluorine, chlorine, bromine, cyano, hydroxyl, mercapto, methyl, ethyl, methoxy, methylthio, hydroximinomethyl, hydroximino ethyl, methoximinomethyl, methoximinoethyl, trifluoromethyl, and carboxymethyl or $R^3$ represents pyrimidyl which is attached in the 4-position and may be mono- to trisubstituted by identical or different substituents selected from the group consisting of fluorine, chlorine, bromine, cyano, hydroxyl, mercapto, methyl, ethyl, methoxy, methylthio, hydroximinomethyl, hydroximinoethyl, methoximinomethyl, methoximinoethyl, trifluoromethyl, and carboxymethyl or $R^3$ represents thienyl which is attached in the 2- or 3-position and may be mono- to trisubstituted by identical or different substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or $R^4$ represents $CONR^6R^7$;

$R^5$ represents H, —$CH_3$, —$CH(CH_3)_2$, Cl or cyclopropyl; and

X represents fluorine, chlorine, ($C_1$-$C_7$)-alkyl or ($C_1$-$C_3$)-haloalkyl;

$R^6$ represents H, Na, K, $NH_4$, $HN(Et)_2$, $H_2N(iPr)_2$, $H_3NCH_2Ph$, $(H_3C)_3NCH_2Ph$, benzyl, ($C_3$-$C_8$)-cycloalkyl, propargyl, ($C_3$-$C_6$)-alkenyl, ($C_1$-$C_8$)-alkyl, fully or partially substituted by F or Cl or carboxy-($C_1$-$C_4$)-alkyl, $CONR^6R^7$, $CONR^7OR^7$, $COOR^8$;

$R^7$ represents $COR^8$, $S(O)_{1-2}R^8$, cyano, $COOR^8$, $CON(R^8)_2$, 1H-pyrrolyl, 1H-imidazolyl, 1H-pyrazolyl, isoxazolyl, oxazolyl, 1,3,4-oxadiazolyl, 1,3,4-thiadiazolyl, thiazolyl, isothiazolyl, 1H-1,3,4-triazolyl, tetrazolyl, oxadiazinyl, 4H-[1,2,4]-oxadiazin-3-yl, dioxazinyl, 5,6-dihydro-[1,4,2]-dioxazin-3-yl, pyridyl, where the heterocyclic radicals are optionally substituted by one or more radicals from the group consisting of $C_1$-$C_4$-alkyl and halogen;

$R^8$ represents H, ($C_1$-$C_8$)-alkyl, ($C_3$-$C_6$)-alkenyl, propargyl, ($C_3$-$C_8$)-cycloalkyl, benzyl; or two radicals $R^8$ form a cycle having 3 to 6 carbon atoms which is saturated or partially unsaturated and optionally contains 1 or 2 further N, S or O atoms, where oxygen atoms are not adjacent to one another;

or $R^6$ and $R^8$ together with the N—CO or N—$S(O)_{1-2}$ group to which they are attached form a 4- to 8-membered cycle which may contain one or more heteroatoms selected from the group consisting of sulphur, oxygen and nitrogen, where oxygen atoms are not adjacent to one another.

6. A compound of formula (I) according to claim 1 in which the symbols are as defined below $R^1$ represents hydrogen or a radical of the formula

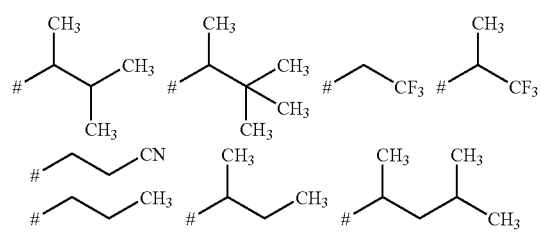

-continued

[chemical structures with # denoting points of attachment]

where # denotes the point of attachment where the radicals may be present in optically pure form or as isomer mixtures;

$R^2$ represents hydrogen, methyl, ethyl, propyl, or $R^1$ and $R^2$ together with the nitrogen atom to which they are attached represent pyrrolidinyl, piperidinyl, morpholinyl, thiomorpholinyl, piperazinyl, 3,6-dihydro-1(2H)-pyridinyl or tetrahydro-1(2H)-pyridazinyl, where these radicals are unsubstituted or substituted by 1 to 3 fluorine atoms, 1 to 3 methyl groups or trifluoromethyl, or $R^1$ and $R^2$ together with the nitrogen atom to which they are attached represent a radical of the formula

[chemical structures]

in which

R' represents hydrogen or methyl,

R" represents methyl, ethyl, fluorine, chlorine or trifluoromethyl, m represents the number 0, 1, 2 or 3, where R" represents identical or different radicals if m represents 2 or 3, R'" represents methyl, ethyl, fluorine, chlorine or trifluoromethyl and n represents the number 0, 1, 2 or 3, where R'" represents identical or different radicals if n represents 2 or 3, $R^3$ represents 2,4-, 2,5- or 2,6-disubstituted phenyl, or 2-substituted phenyl or represents 2,4,6- or 2,4,5-trisubstituted phenyl having substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, carboxyl and carboxymethyl or $R^3$ represents thienyl which is attached in the 2- or 3-position and may be mono- to trisubstituted by identical or different substituents selected from the group consisting of fluorine, chlorine, bromine, cyano, nitro, hydroxyl, mercapto, methyl, ethyl, methoxy, methylthio, hydroximinomethyl, hydroximinoethyl, methoximinomethyl, methoximinoethyl, trifluoromethyl, carboxyl and carboxymethyl or $R^4$ represents $CONR^6R^7$;

$R^5$ represents H, —$CH_3$;

X represents fluorine, chlorine, methyl or trifluoromethyl;

$R^6$ represents H, Na, K, $NH_4$, $HN(Et)_2$, $H_2N(iPr)_2$, $H_3NCH_2Ph$, $(H_3C)_3NCH_2Ph$, benzyl, $(C_3-C_8)$-cycloalkyl, propargyl, $(C_3-C_6)$-alkenyl, $(C_1-C_8)$-alkyl, fully or partially substituted by F or Cl or carboxy-$(C_1-C_4)$-alkyl, $CONR^6R^7$, $CONR^7OR^7$, $COOR^8$;

$R^7$ represents $COR^8$, $S(O)R^8$, $COOR^8$, 1H-pyrrolyl, 1H-imidazolyl, 1H-pyrazolyl, isoxazolyl, oxazolyl, 1,3,4-oxadiazolyl, 1,3,4-thiadiazolyl, thiazolyl, isothiazolyl, 1H-1,3,4-triazolyl, tetrazolyl, oxadiazinyl, 4H-[1,2,4]-oxadiazin-3-yl, dioxazinyl, 5,6-dihydro-[1,4,2]-dioxazin-3-yl, pyridyl, where the heterocyclic radicals are optionally substituted by one or more radicals selected from the group consisting of $C_1-C_4$-alkyl and halogen;

$R^8$ independently of the other radicals represents H, methyl, ethyl, propyl, i-propyl, butyl, i-butyl, sec-butyl, t-butyl, pentyl, hexyl, $(C_1-C_3)$-haloalkyl, $(C_2-C_6)$-alkenyl, propargyl, $(C_3-C_6)$-cycloalkyl, benzyl;

or $R^6$ and $R^8$ together with the N—CO or N—$S(O)_{1-2}$ group to which they are attached form a 4- to 8-membered cycle which may contain one or more heteroatoms selected from the group consisting of sulphur, oxygen and nitrogen, where oxygen atoms are not adjacent to one another.

7. A composition for controlling unwanted microorganisms, comprising at least one compound of the formula (I) according to claim 1, and an extender or a surfactant or a combination thereof.

8. A composition according to claim 7, further comprising at least one additional compound selected from the group consisting of fungicides, bactericides, acaricides, nematicides, and insecticides.

9. A process for preparing a compound of the formula (I) according to claim 1 in which X represents chlorine and $R^4$ represents $CONR^6R^7$, comprising a) reacting a substituted 3-aminopyrazole derivative of the formula II,

[chemical structure] (II)

with a malonic ester of the formula IIa

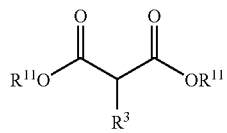
(5)

where $R^{10}$ represents $C_1$-$C_4$-alkyl and $R^{11}$ represents $C_1$-$C_8$-alkyl or aryl to give a dihydroxypyrazolopyrimidine III

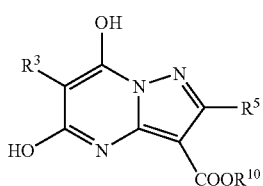
(III)

b) halogenation of a compound of formula III to give a halopyrazolopyrimidine IV

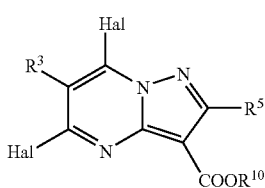
(IV)

c) reaction of a compound of formula IV with an amine to give a 7-aminopyrazolopyrimidine V

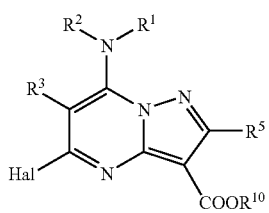
(V)

d) hydrolysis of a compound of formula (V) to give a pyrazolopyrimidinecarboxylic acid VI

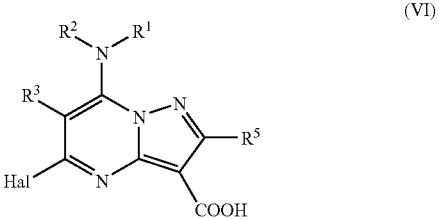
(VI)

e) reaction of a compound of formula (VI) with a chlorinating agent to give a pyrazolopyrimidine acid chloride VII

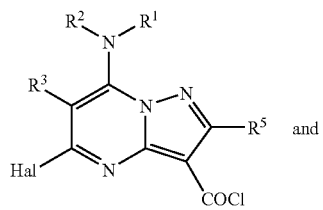
(VII)

and f) reaction of a compound of formula VII with $HNR^6R^7$ to give a compound of the formula (Ia)

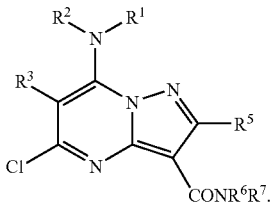
Ia

* * * * *